(12) United States Patent
Miura et al.

(10) Patent No.: US 8,263,025 B2
(45) Date of Patent: Sep. 11, 2012

(54) FLOW CELL

(75) Inventors: Toru Miura, Kanagawa (JP); Tsutomu Horiuchi, Kanagawa (JP); Yuzuru Iwasaki, Kanagawa (JP); Michiko Seyama, Kanagawa (JP); Serge Camou, Kanagawa (JP); Tsuyoshi Hayashi, Kanagawa (JP); Jun-ichi Takahashi, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 32 days.

(21) Appl. No.: 12/864,854

(22) PCT Filed: Jan. 30, 2009

(86) PCT No.: PCT/JP2009/051592
§ 371 (c)(1),
(2), (4) Date: Jul. 27, 2010

(87) PCT Pub. No.: WO2009/096529
PCT Pub. Date: Aug. 6, 2009

(65) Prior Publication Data
US 2010/0307617 A1 Dec. 9, 2010

(30) Foreign Application Priority Data

| Feb. 1, 2008 | (JP) | 2008-022572 |
|---|---|---|
| Feb. 1, 2008 | (JP) | 2008-022574 |
| Feb. 1, 2008 | (JP) | 2008-022580 |
| Feb. 1, 2008 | (JP) | 2008-022585 |
| Feb. 1, 2008 | (JP) | 2008-022591 |
| Jul. 4, 2008 | (JP) | 2008-176246 |
| Jul. 4, 2008 | (JP) | 2008-176247 |

(51) Int. Cl.
*G01N 15/06* (2006.01)
*G01N 33/00* (2006.01)
*G01N 33/48* (2006.01)

(52) U.S. Cl. ......... 422/503; 422/50; 422/68.1; 422/502; 422/504; 422/505; 422/506; 422/507

(58) Field of Classification Search .................... 422/50, 422/68.1, 502, 503, 504, 505, 506, 507
See application file for complete search history.

(56) References Cited

U.S. PATENT DOCUMENTS 4,233,029 A * 11/1980 Columbus .................... 436/174
(Continued)

FOREIGN PATENT DOCUMENTS

EP 0 430 248 A2 6/1991
(Continued)

OTHER PUBLICATIONS

Analytical Chemistry, vol. 77, No. 24, Dec. 15, 2005, pp. 7901-7907.
(Continued)

*Primary Examiner* — Brian J Sines
(74) *Attorney, Agent, or Firm* — Blakely, Sokoloff, Taylor & Zafman

(57) ABSTRACT

Ends (134*a*-1) of projections (134*a*) do not contact a first substrate (11), forming a gap between the ends (134*a*-1) and the first substrate (11). The internal capacity of a suction pump (17) can be increased by an amount by which the projections (134*a*) are shortened, compared to a conventional structure in which pillars are formed to connect the ceiling and bottom of the cavity of a capillary pump. The capacity of the suction pump (17) can be increased without enlarging the planar shape. Further, the ends (134*a*-1) of the projections (134*a*) do not contact the first substrate (11), forming a gap between them. An impurity can pass through the gap, and clogging of the inside of the suction pump (17) with the impurity can be prevented, realizing a stable operation.

8 Claims, 48 Drawing Sheets

U.S. PATENT DOCUMENTS

| | | | |
|---|---|---|---|
| 6,599,475 B1 * | 7/2003 | Berndt et al. | 422/401 |
| 2002/0086436 A1 | 7/2002 | Buechler | |
| 2003/0124029 A1 * | 7/2003 | Webb et al. | 422/102 |
| 2004/0265171 A1 | 12/2004 | Pugia et al. | |
| 2005/0169778 A1 * | 8/2005 | Blankenstein et al. | 417/410.1 |
| 2007/0269893 A1 | 11/2007 | Blankenstein et al. | |

FOREIGN PATENT DOCUMENTS

| | | |
|---|---|---|
| JP | H07-036017 B | 4/1995 |
| JP | 2000-329766 A | 11/2000 |
| JP | 2004-077305 A | 3/2004 |
| JP | 2006-225197 A | 8/2006 |
| JP | 2007-530938 A | 11/2007 |
| WO | WO 03/103835 A1 | 12/2003 |
| WO | WO 2004/051228 A1 | 6/2004 |
| WO | WO 2007/149042 A1 | 12/2007 |

OTHER PUBLICATIONS

Zimmermann et al., "Capillary pumps for autonomous capillary systems", The Royal Society of Chemistry 2007, Lab Chip, pp. 119-125.

Horiuchi et al., "Passive-fluidic device using integrated capillary tubes for SPR measurement without external pump", Extended Abstracts (The 55th Spring Meeting, 2008); The Japan Society of Applied Physics and Related Societies, No. 3, Mar. 27, 2008, p. 1353.

* cited by examiner

FIG.5A
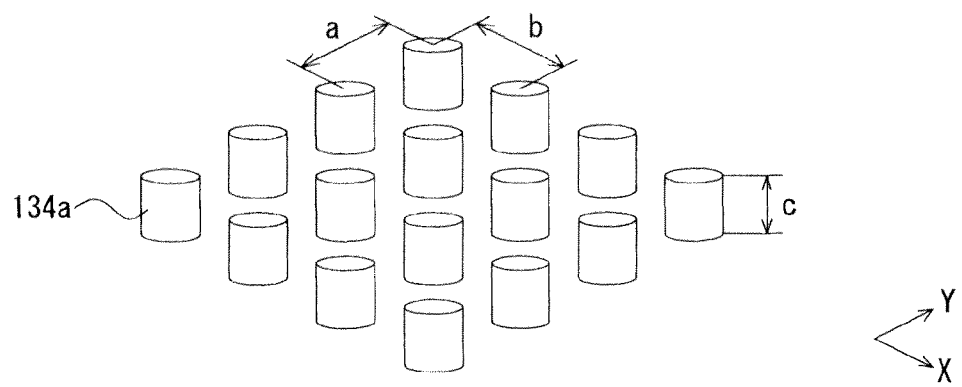
FIG.5B
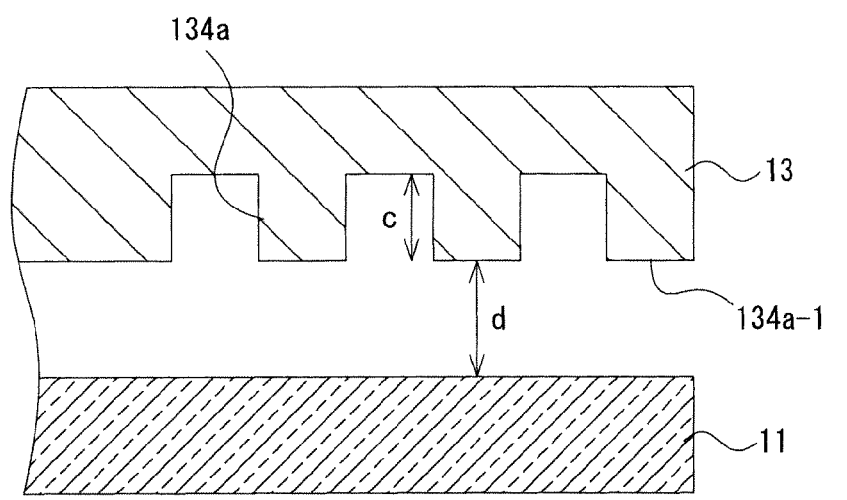
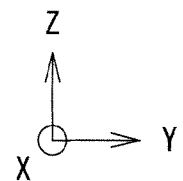

FIG.27
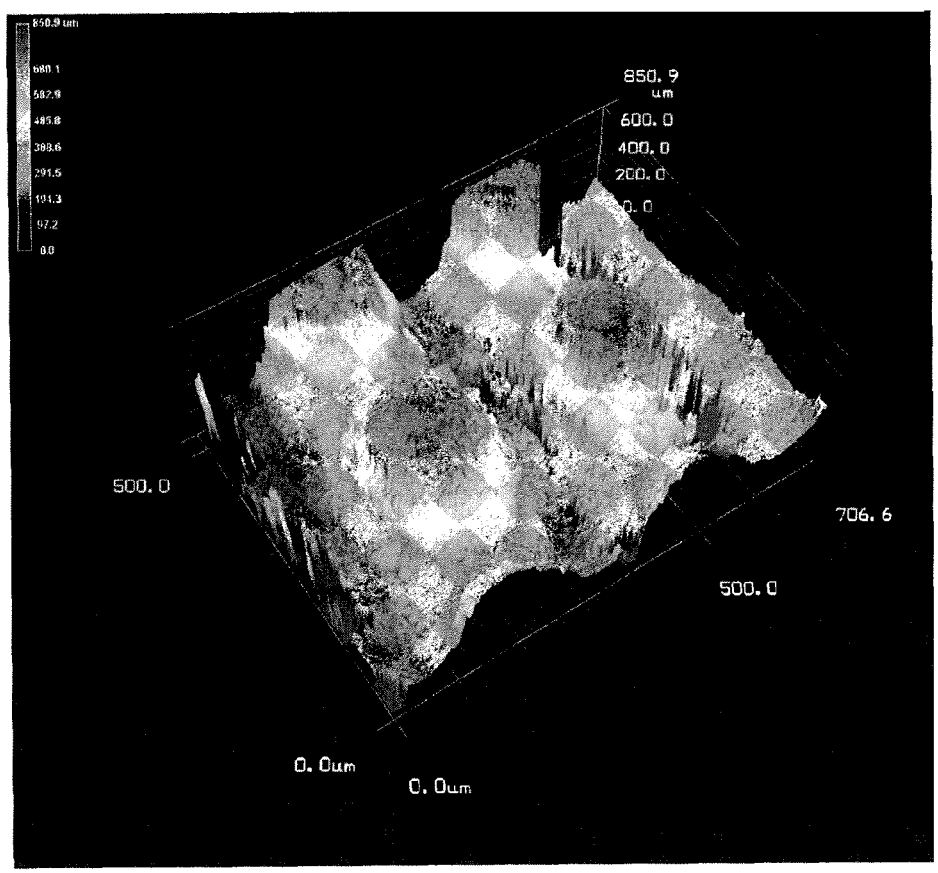
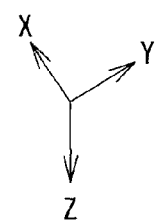

FIG.28
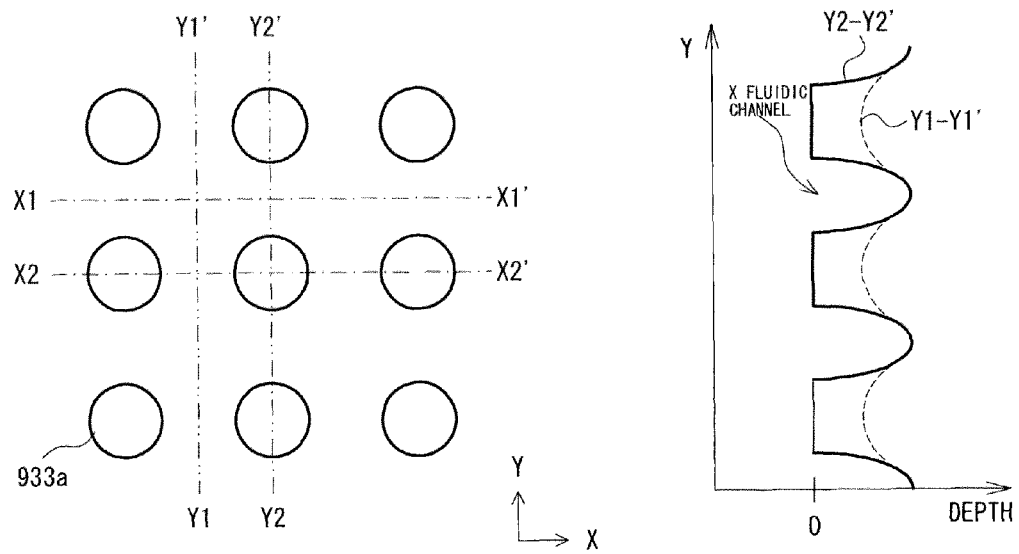
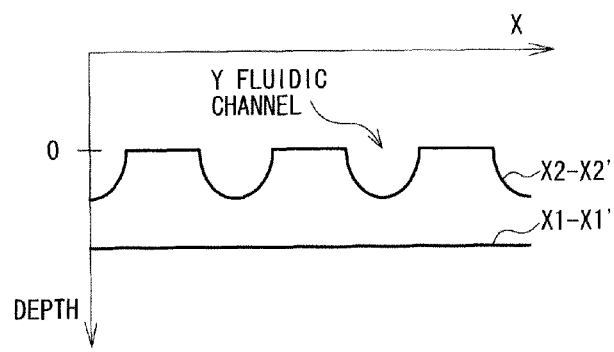
FIG.29
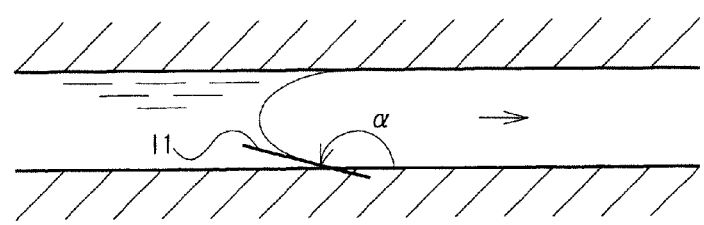

US 8,263,025 B2

FLOW CELL

This is a non-provisional application claiming the benefit of International application number PCT/JP2009/051592 filed Jan. 30, 2009.

TECHNICAL FIELD

The present invention relates to a flow cell having a predetermined fluidic channel used for measurement by a measurement apparatus, and a pump for supplying a sample solution to the fluidic channel.

BACKGROUND ART

Measurement using a sophisticated biomolecule identification function such as an antigen-antibody reaction and binding of a DNA fragment (DNA probe) to DNA is becoming an important technique in clinical testing, measurement in the field of biochemistry, and measurement for environmental pollutants. Examples of the measurement are micro-TAS (Total Analysis Systems), micro combinatorial chemistry, chemical IC, chemical sensor, biosensor, microanalysis, electrochemical analysis, QCM measurement, SPR measurement, and ATR measurement. In the field of measurement, the amount of sample solution to be measured is often very small.

In this measurement, a small amount of sample solution is directly transferred to a detecting portion to measure it with high sensitivity and high efficiency without decreasing the concentration of the analyte. As a technique for transferring a small amount of sample solution, a several hundred μm-wide fluidic channel is formed on a substrate, and a solution is transferred by an external pressure by a syringe pump or the like. Alternatively, a solution is transferred by electrostatic force, by electrowetting, by changing the volume or generating bubbles upon heating, or by using an electroosmotic flow.

To transfer a small amount of sample solution by these methods, it is necessary to form a microchannel as a fluidic channel on a substrate (chip), and arrange other components on this substrate. It is not easy to fabricate this structure. Transferring a sample solution by an external pressure requires components such as a pump and tube in addition to a chip which forms a fluidic channel. A sample solution is wasted on the transfer path including the tube, which exerts a limitation on decreasing the amount of sample solution.

As a method of analyzing a small amount of sample solution, paper chromatography analysis using filter paper has conventionally been known. For example, improved immunochromatography and immunoconcentration have been proposed as simple, low-cost means for measurement of biological substances (reference 1: Japanese Patent Publication No. 7-036017, and reference 2: Japanese Patent Laid-Open No. 2000-329766). There is also proposed a measurement chip in which filter paper is arranged in a fluidic channel formed in a plastic structure (reference 3: Amal. Chem. 2005, 77. 7901-7907). However, these paper chromatography methods have limitations in the shape of the fluidic channel and the like, and cannot perform complicated chemical analysis.

Under the circumstance, it is recently proposed to form, on or in a substrate by a microfabrication technique, regions serving as a fluidic channel and pump for transferring a sample solution by capillary action (reference 4: Martin Zimmermann, Heinz Schmid, Patrick Hunziker and Emmanuel Delamarche, "Capillary pumps for autonomous capillary systems", The Royal Society of Chemistry 2007, Lab Chip, 2007, 7, 119-125, First published as an Advance Article on the web 17 Oct. 2006). A measurement chip fabricated by this technique has an inlet port for introducing a sample solution, a capillary pump for sucking it, and a measurement fluidic channel formed between the inlet port and the capillary pump. The capillary pump is formed from a cavity containing a plurality of pillars which connect the ceiling and bottom. The pillars have an interval enough to cause capillary action. In this measurement chip, when a sample solution is introduced from the inlet port, it sequentially flows from the inlet port to the measurement fluidic channel and pump. When the sample solution reaches the capillary pump, it is sucked by the capillary action of the capillary pump. The sample solution which stays at the inlet port flows to the pump through the measurement fluidic channel by the suction force of the capillary pump.

DISCLOSURE OF INVENTION

Problems to be Solved by the Invention

Such a measurement chip desirably has a large-capacity capillary pump to perform long-time measurement or measure many sample solutions. However, in the conventional capillary pump, components are formed between a substrate and a member which covers it. Increasing the interval between the substrate and the member is limited in terms of the generation of capillary action. This means the substrate and member must be enlarged two-dimensionally to increase the capacity. Then, the planar shape of the measurement chip becomes large, obstructing downsizing of not only the measurement chip itself but also a measurement apparatus in which the measurement chip is mounted.

A sample solution such as food and drink or a body fluid sometimes contains an impurity depending on its type. If the inside of the capillary pump is too narrow, it is clogged with the impurity, failing a stable operation. Realization of a stable operation requires pre-processing such as removal of the impurity.

The present invention has been made to solve the above problems, and has as the first object to provide a flow cell capable of increasing the pump capacity without enlarging the planar shape.

It is the second object to provide a flow cell capable of realizing a stable operation.

Means of Solution to the Problems

A flow cell according to the present invention comprises a first substrate in which light is transmissive, a second substrate which is disposed on the first substrate, an opening which is formed in the second substrate, a fluidic channel which is formed between the first substrate and the second substrate and has one end connected to the opening, and a pump which is formed between the first substrate and the second substrate, is connected to the other end of the fluidic channel, and sucks, by a surface tension generated by the first substrate and the second substrate, a liquid that has reached the fluidic channel from the opening, wherein the pump includes a recess formed in at least one of the first substrate and the second substrate, and a plurality of pillars which stand upright in the recess, and the pillars do not contact either of the first substrate and the second substrate.

A flow cell according to the present invention comprises a first substrate in which light is transmissive, a second substrate which is disposed on the first substrate, a third substrate which is disposed on the second substrate, an opening which is formed in the second substrate and the third substrate, a fluidic channel which is formed between the first substrate and the second substrate and has one end connected to the opening, and a pump which is formed between the first substrate and the second substrate and between the second substrate and the third substrate, is connected to the other end of the fluidic channel, and sucks, by a surface tension generated by the first substrate and the second substrate or by the second substrate and the third substrate, a liquid that has reached the fluidic channel from the opening.

Effects of the Invention

According to the present invention, pillars in a recess which forms a pump are formed not to contact the first substrate or second substrate. The pump capacity can be increased without enlarging the planar shape.

Also, as pillars are formed not to contact the first substrate or second substrate, a gap is formed between the pillars and the first substrate or second substrate. An impurity can pass through the gap, and clogging of the inside of the suction pump with the impurity can be prevented.

According to the present invention, pumps are formed between the first and second substrates and between the second and third substrates. The pump capacity can therefore be increased without enlarging the planar shape.

BRIEF DESCRIPTION OF DRAWINGS

FIG. 5A is a view for schematically explaining the array of projections;

FIG. 5B is a sectional view of the main part of a suction pump;

FIG. 27 is a view exemplifying the arrangement of projections in a suction pump;

FIG. 28 is a view showing the planar and sectional shapes of the projections in the suction pump;

FIG. 29 is a view showing the state of a sample solution which flows through a straight fluidic channel;

BEST MODE FOR CARRYING OUT THE INVENTION

Figure 1:
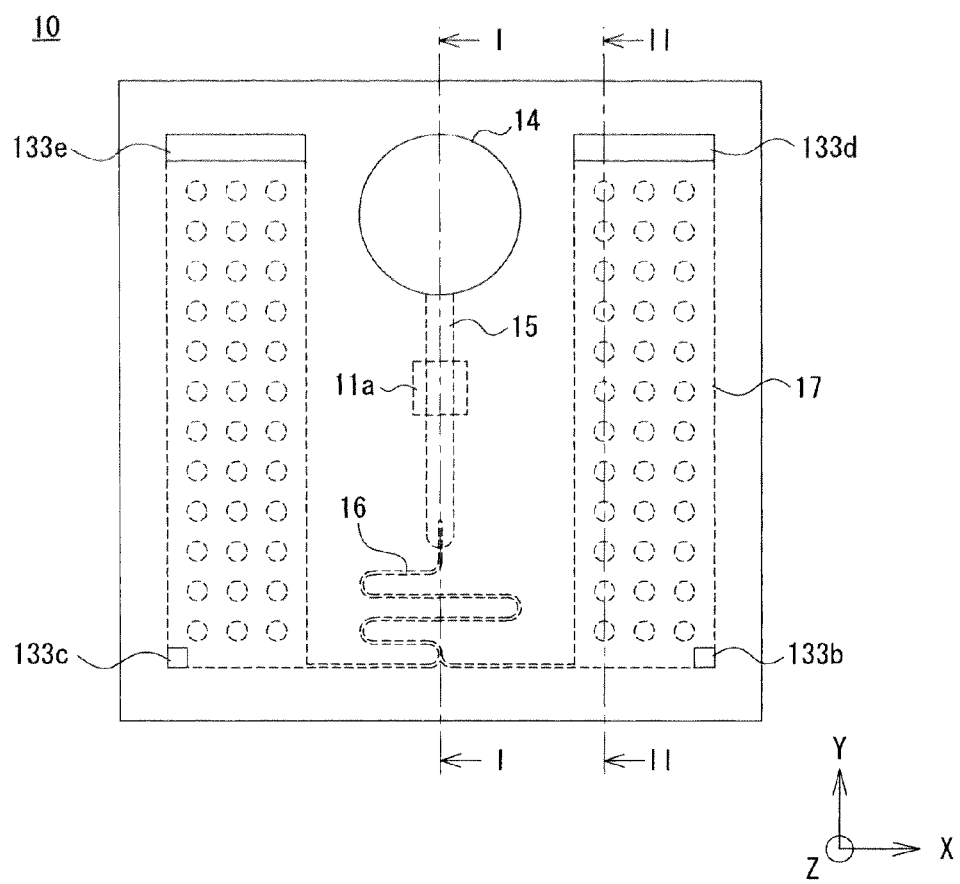
FIG. 1 is a plan view exemplifying the structure of a flow cell according to the first embodiment of the present invention.
Figure 2:
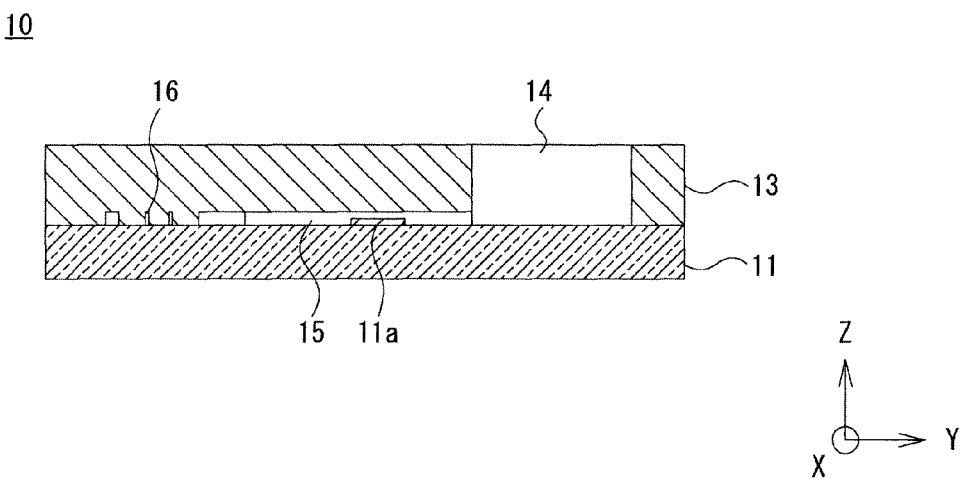
FIG. 2 is a sectional view taken along the line I-I in FIG. 1.

Preferred embodiments of the present invention will be described below with reference to the accompanying drawings.

First Embodiment

The first embodiment according to the present invention will be described in detail.

<Structure of Flow Cell>

As shown in FIGS. 1 to 4, a flow cell 10 according to the first embodiment is formed from a first substrate 11 which has an almost rectangular shape when viewed from the top, and a second substrate 13 which is arranged on the first substrate 11. The flow cell 10 configured by stacking these substrates includes an inlet port 14 which passes through the second substrate 13 and allows introducing a sample solution, two suction pumps 17 which are formed between the first substrate 11 and the second substrate 13, and a fluidic channel which connects the suction pumps 17 and the inlet port 14. The fluidic channel is made up of a measurement fluidic channel 15 which has one end connected to the inlet port 14 and is formed between the first substrate 11 and the second substrate 13, and a resistance fluidic channel 16 which has one end connected to the other end of the measurement fluidic channel 15 and is formed between the first substrate 11 and the second substrate 13.

<<First Substrate>>

The first substrate 11 is made of optical glass such as BK7, is about 1 mm in thickness, and has an almost rectangular shape about 16 mm on a side when viewed from the top. An Au layer 11a is formed by vapor deposition, sputtering, plating, or the like on the upper surface of the first substrate 11, i.e., a surface of the first substrate 11 on the side of the second substrate 13. The Au layer 11a may be formed only at a portion corresponding to the measurement fluidic channel 15.

<<Structure of Second Substrate>>

The second substrate 13 is formed from, e.g., an acrylic substrate about 0.5 to 5 mm in thickness, and has a planar shape corresponding to the first substrate 11. A through hole 131 is formed near the center of the second substrate 13 on its one side. The lower surface of the second substrate 13 has a channel 132 which has one end connected to the through hole 131, extends toward the other side opposite to the one side, and has an almost rectangular shape when viewed from the top, a meandering channel 133 which is connected to the other end of the channel 132 and is formed to the vicinity of the other side, and two recesses 134 which are formed on the two sides of the meandering channel 133.

The through hole 131 forms the inlet port 14 which is an almost columnar space with the upper surface of the first substrate defining its bottom.

Together with the upper surface of the first substrate 11, the channel 132 forms the measurement fluidic channel 15 which is an almost rectangular parallelepiped space. A section of the measurement fluidic channel 15 that is perpendicular to the longitudinal direction has dimensions enough to cause capillary action with respect to an aqueous solution.

The meandering channel 133 has a crank-like planar shape with a plurality of bent portions. The bent portion is smoothly bent into an almost arcuate shape, i.e., curved shape. The other end of the meandering channel 133 branches near the other side of the second substrate 13. The branches extend in opposite directions in the perpendicular direction and are connected to the adjacent recesses 134, respectively. When the first substrate 11 and second substrate 13 are brought into contact with each other, the meandering channel 133 forms the meandering resistance fluidic channel 16. The resistance fluidic channel 16 has sectional dimensions enough to cause capillary action with respect to an aqueous solution.

The recesses 134 are two cavities which are formed from the lower surface toward the upper surface of the second substrate 13 and have an almost rectangular shape when viewed from the top. A plurality of almost columnar projections 134a are formed in each cavity and project downward from its ceiling. By setting the projections 134a to have an interval enough to cause capillary action, the recess 134 functions as the suction pump. The recess 134 is formed into an almost rectangular shape when viewed from the top. Vents 133d and 133e are formed at ends of the recesses 134 near the one side. Vents 133b and 133c are formed at corners of the recesses 134 near the other side that are opposite to corners connected to the branches of the other end of the meandering channel 133. The vents 133b to 133e pass through the second substrate 13.

Figure 3:
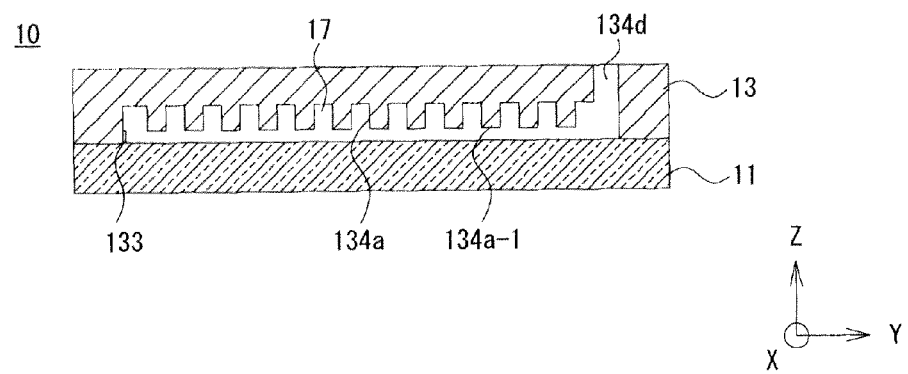
FIG. 3 is a sectional view taken along the line II-II in FIG. 1.
Figure 4:
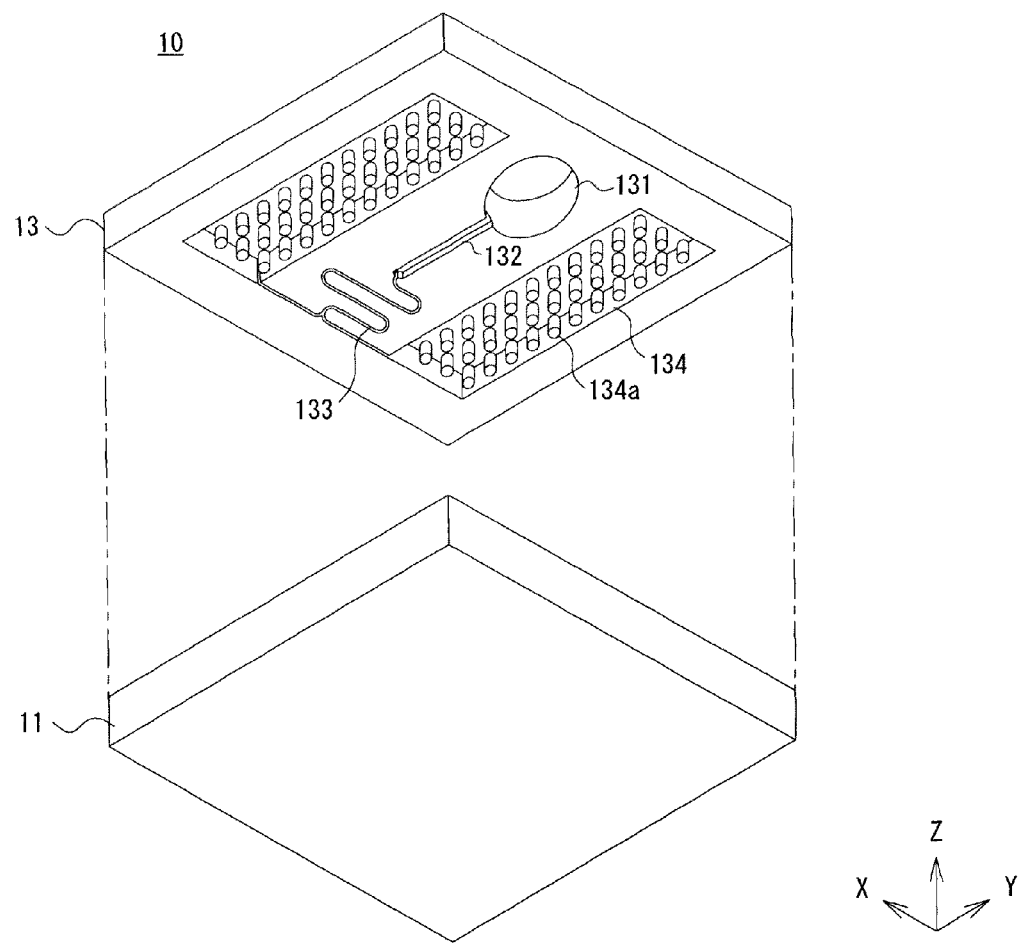
FIG. 4 is an exploded perspective view of the flow cell in FIG. 1 when viewed from the bottom.

The projections 134a are regularly juxtaposed in the X and Y directions at predetermined intervals. In the first embodiment, when the second substrate 13 is disposed on the first substrate 11, ends 134a-1 of the projections 134a on the side of the first substrate 11 are spaced apart from the first substrate 11, as shown in FIG. 3. The distance between the end 134a-1 and the substrate 11 is set to cause capillary action.

The second substrate 13 can be fabricated by injection molding using a mold having a predetermined pattern, laser processing, cutting using an end mill, or the like.

<Method of Manufacturing Flow Cell>

A method of manufacturing the flow cell 10 according to the first embodiment will be exemplified. First, the second substrate 13 is placed on the first substrate 11. When the Au layer 11a is formed only at part of the first substrate 11, the second substrate 13 is placed on the first substrate 11 so that the channel 132 for forming the measurement fluidic channel 15 is located on the Au layer 11a.

After the second substrate 13 is placed on the first substrate 11, they are fixed. As a fixing method, an adhesive may be applied to the edges of the first substrate 11 and second substrate 13 that are in contact. Alternatively, engaging means may be arranged at the sides of the first substrate 11 and second substrate 13 to engage with each other, or an adhesive tape or the like may be attached to the sides of the first substrate 11 and second substrate 13. As a result, the first substrate 11 and second substrate 13 are fixed to each other, completing the flow cell 10 having the inlet port 14, measurement fluidic channel 15, resistance fluidic channel 16, and suction pumps 17.

<Operation of Flow Cell>

The operation of the flow cell 10 according to the first embodiment will be explained.

When a sample solution is injected from the inlet port 14, it proceeds sequentially through the measurement fluidic channel 15 and resistance fluidic channel 16 by capillary action, and flows into the suction pumps 17. In the suction pumps 17, a plurality of projections 134a are formed to increase the surface area per unit volume, compared to a structure in which no projection 134a is formed. The inside of the suction pump 17 has dimensions enough to cause capillary action. The sample solution which has flowed into the suction pumps 17 proceeds through their insides. Note that the flow rate changes depending on the shape of the recess 134 such as the outer shape and interval of the projection 134a, the resistance acting on the sample solution, and the like.

The sample solution injected from the inlet port 14 passes through the measurement fluidic channel 15 and resistance fluidic channel 16, flows into the suction pumps 17, and proceeds through their insides.

In the first embodiment, the ends 134a-1 of the projections 134a do not contact the first substrate 11, and a gap is formed between them, as shown in FIG. 3. The internal capacity of the suction pump 17 is increased by an amount by which the projections 134a are shortened, compared to a conventional structure in which pillars are formed to connect the ceiling and bottom of the cavity of a capillary pump. The capacity of the suction pump 17 can be increased without enlarging the planar shape. Since the ends 134a-1 of the projections 134a, and portions of the first substrate 11 that abut against the ends 134a-1 in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 17 may be clogged with the impurity in a conventional structure. However, since the ends 134a-1 of the projections 134a do not contact the first substrate 11, a gap is formed between them, as described above, allowing the impurity to pass through the gap. Clogging of the inside of the suction pump 17 with the impurity can be prevented, realizing a stable operation.

The interval between the projections 134a and the distance between the end 134a-1 and the first substrate 11 can be freely set as long as the capillary force acts on a liquid which has entered the suction pump 17. More specifically, as shown in FIGS. 5A and 5B, a and b are the intervals between the projections 134a, c is the Z length of the projection 134a, and d is the distance between the end 134a-1 and the first substrate 11. These values can be freely set as long as the capillary force acts on a liquid in the suction pump 17. If the liquid contains an impurity, the values a to d are appropriately set in accordance with the size of the impurity. If the liquid flows through only the gap between the projections 134a and d=0, when the liquid contains a substance (impurity) larger than the intervals a and b between the projections 134a, the inside of the suction pump 17 is clogged, and the flow cell 10 cannot be used. In this case, the value of the distance d is set to be larger than the impurity, preventing clogging.

For example, when milk immediately after milking (unhomogenized) is used as a liquid, the fat globule aggregate, which is the largest impurity contained in milk, has a size of about 40 μm. By setting d=100 μm, the flow cell 10 can suck milk without clogging even when a=b=25 μm. For blood, erythrocyte, which is the largest cell contained in blood, has a size of about 7 to 8 μm. By setting d=20 μm, the flow cell 10 can suck blood without clogging even when a=b=5 μm.

In the first embodiment, the channel 132 has an almost rectangular shape when viewed from the top, and is formed at almost the center of the second substrate 13. However, the shape and formation position of the channel 132 are not limited to them and can be freely set as long as the channel 132 passes above the Au layer 11a. Even the shape and position of the measurement fluidic channel 15 defined by the channel 132 can be freely set.

In the first embodiment, the through hole 131 has an almost circular shape when viewed from the top. However, the shape of the through hole 131 is not limited to this and can be freely set.

In the first embodiment, the recess 134 has an almost rectangular shape when viewed from the top. However, the planar shape of the recess 134 is not limited to this and can be freely set. Similarly, even the shape of the projection 134a formed in the recess 134 is not limited to an almost columnar shape and can be freely set as long as the surface area in the recess 134 increases.

Note that the recess 134 is formed in the second substrate 13 in the embodiment, but may be formed in the first substrate 11. In this case, it suffices to form the recess in the upper surface of the first substrate 11. Even with this structure, one can obtain the same operation effects as those described above.

In the first embodiment, the resistance fluidic channel 16 is arranged, but may be omitted.

Second Embodiment

The second embodiment according to the present invention will be described in detail. In the second embodiment, a sheet-like member is interposed between the first and second substrates in the first embodiment. In the second embodiment, the same reference numerals as those in the first embodiment denote the same parts, and a description thereof will be properly omitted.

<Structure of Flow Cell>

Figure 6:
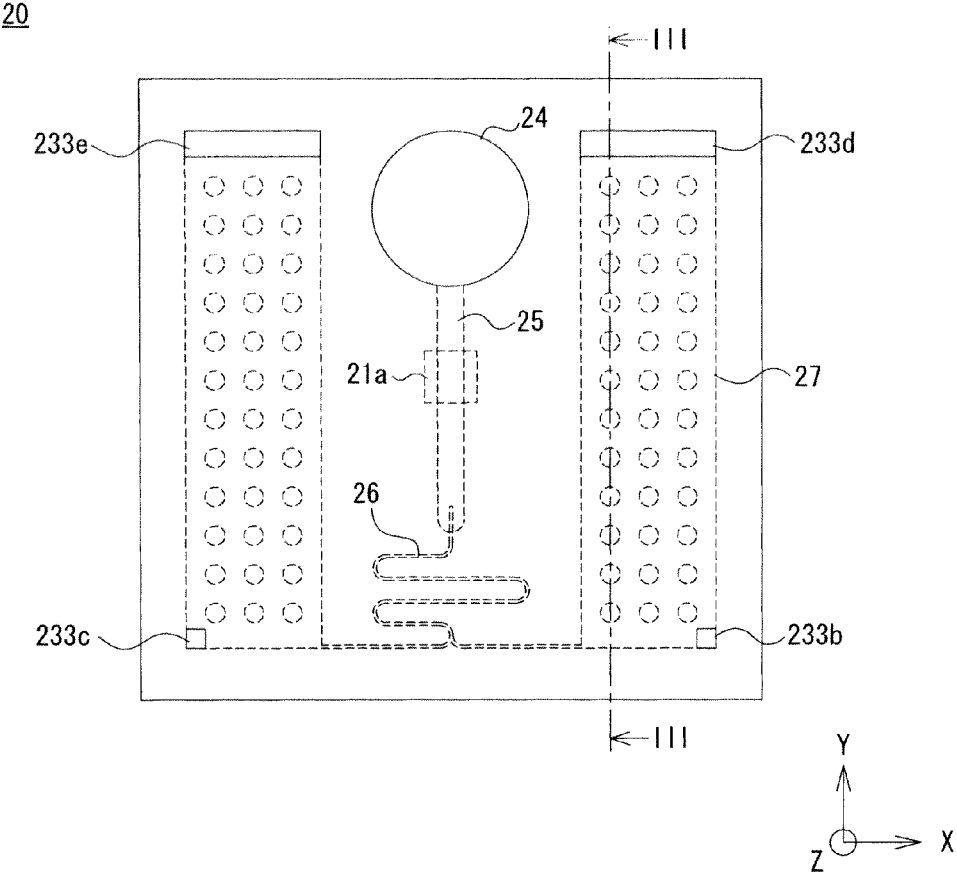
FIG. 6 is a plan view exemplifying the structure of a flow cell according to the second embodiment of the present invention.
Figure 7:
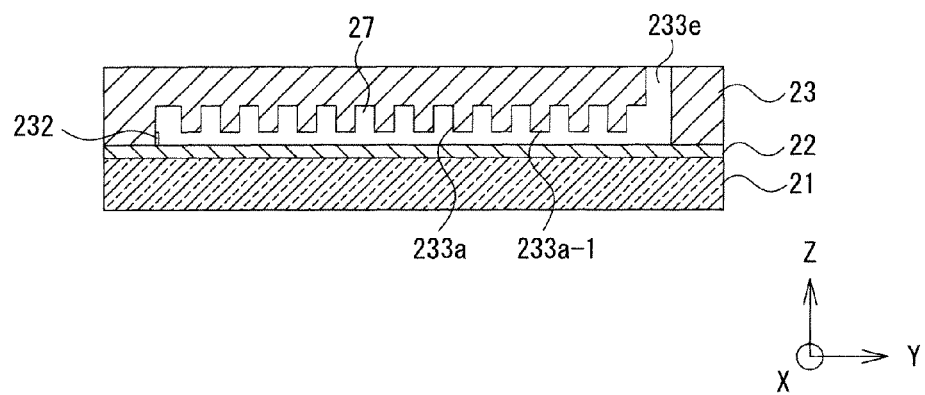
FIG. 7 is a sectional view taken along the line III-III in FIG. 6.
Figure 8:
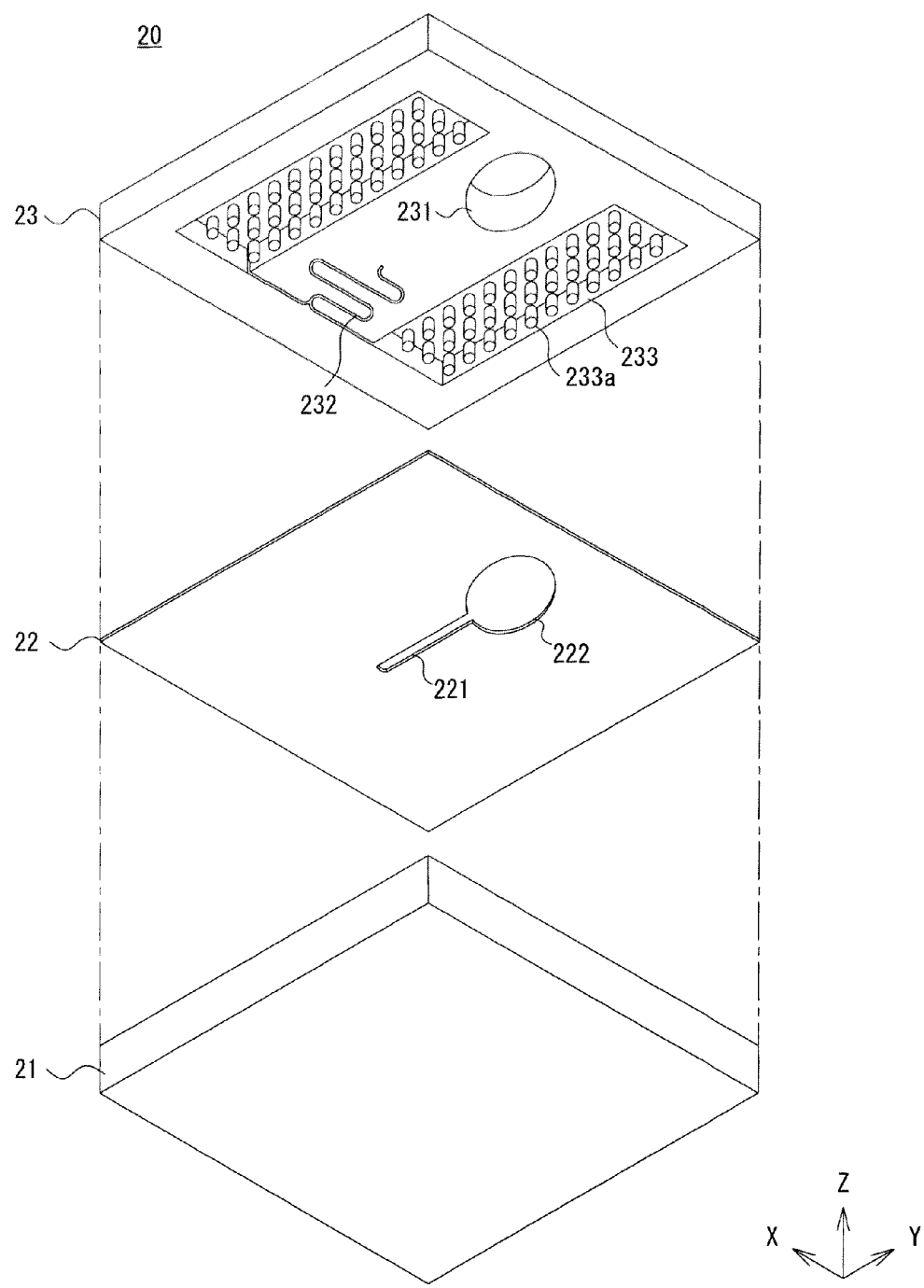
FIG. 8 is an exploded perspective view of the flow cell in FIG. 6 when viewed from the bottom.

As shown in FIGS. 6 to 8, a flow cell 20 according to the second embodiment is formed from a first substrate 21 which has an almost rectangular shape when viewed from the top, a sheet-like member 22 which is disposed on the first substrate 21, and a second substrate 23 which is disposed on the sheet-like member 22. The flow cell 20 configured by stacking the substrates and sheet-like member includes an inlet port 24 which passes through the second substrate 23 and allows introducing a sample solution, two suction pumps 27 which are formed between the sheet-like member 22 and the second substrate 23, and a fluidic channel which connects the suction pumps 27 and the inlet port 24. The fluidic channel is made up of a measurement fluidic channel 25 which has one end connected to the inlet port 24 and is formed in the sheet-like member 22 interposed between the first substrate 21 and the second substrate 23, and a resistance fluidic channel 26 which has one end connected to the other end of the measurement fluidic channel 25 and is formed between the sheet-like member 22 and the second substrate 23.

<<First Substrate>>

The first substrate 21 has the same shape and structure as those of the first substrate 11 in the first embodiment. An Au layer 21a is selectively formed on the upper surface of the first substrate 21.

<<Sheet-Like Member>>

The sheet-like member 22 is formed from, e.g., a well-known adhesive tape about 10 μm to 150 μm in thickness, and has a planar shape corresponding to the first substrate 21. The sheet-like member 22 has a slit 221 which is formed at almost the center and has an almost rectangular shape when viewed from the top, and an opening 222 which is connected to one end of the slit 221 and has an almost circular shape when viewed from the top. The slit 221 is formed so that its longitudinal direction becomes almost parallel to any one side of the sheet-like member 22.

Together with the upper surface of the first substrate 21 and the lower surface of the second substrate 23, the slit 221 forms the measurement fluidic channel 25 which is an almost rectangular parallelepiped space. A section of the measurement fluidic channel 25 that is perpendicular to the longitudinal direction has dimensions enough to cause capillary action with respect to an aqueous solution.

The sheet-like member 22 can be fabricated by, for example, processing an adhesive tape into a desired shape by a cutter, laser, or the like.

<<Structure of Second Substrate>>

The second substrate 23 has a structure in which the channel 132 is omitted from the second substrate 13 in the first embodiment. A through hole 231 is formed near the center of the second substrate 23 on its one side. The lower surface of the second substrate 23 has a meandering channel 232 which is formed from almost the center to the vicinity of the other side opposite to the one side, and two recesses 233 which are formed on the two sides of the meandering channel 232.

The through hole 231 has the same planar shape as that of the opening 222.

The meandering channel 232 has a crank-like planar shape which has a plurality of bent portions and is bent repetitively in a direction perpendicular to the direction of distance between the one side and the other side. The bent portion is smoothly bent into an almost arcuate shape, i.e., curved shape. The other end of the meandering channel 232 branches near the other side of the second substrate 23. The branches extend in opposite directions in the perpendicular direction and are connected to the adjacent recesses 233, respectively.

The recesses 233 are formed from the lower surface toward the upper surface of the second substrate 23. A plurality of almost columnar projections 233a are formed in each cavity and project downward from its ceiling. By setting the projections 233a to have an interval enough to cause capillary action, the recess 233 functions as the suction pump. The recess 233 is formed into an almost rectangular shape when viewed from the top. Vents 233d and 233e are formed at ends of the recesses 233 near the one side. Vents 233b and 233c are formed at corners of the recesses 233 near the other side that are opposite to corners connected to the branches of the other end of the meandering channel 232. The vents 233b to 233e pass through the second substrate 23.

Together with the opening 222 and the upper surface of the first substrate 21, the through hole 231 forms the inlet port 24 which is an almost columnar space with the upper surface of the first substrate 21 defining its bottom.

When the second substrate 23 and sheet-like member 22 are brought into contact with each other, the meandering channel 232 forms the meandering resistance fluidic channel 26. The resistance fluidic channel 26 has sectional dimensions enough to cause capillary action with respect to an aqueous solution.

The projections 233a in the recess 233 are regularly juxtaposed in the X and Y directions at predetermined intervals. In the second embodiment, when the second substrate 23 is disposed on the sheet-like member 22, ends 233a-1 of the projections 233a on the side of the first substrate 21 are spaced apart from the sheet-like member 22, as shown in FIG. 7. The distance between the end 233a-1 and the sheet-like member 22 is set to cause capillary action.

<Method of Manufacturing Flow Cell>

A method of manufacturing the flow cell 20 according to the second embodiment will be exemplified. First, the sheet-like member 22 is placed on the first substrate 21. When the Au layer 21a is formed only at part of the first substrate 21, the sheet-like member 22 is placed on the first substrate 21 so that the slit 221 for forming the measurement fluidic channel 25 is positioned on the Au layer 21a.

Then, the second substrate 23 is placed on the sheet-like member 22 so that the through hole 231 and opening 222 are connected to each other and one end of the meandering channel 232 is positioned in the other end of the slit 221.

After the first substrate 21, sheet-like member 22, and second substrate 23 are stacked in this way, they are pressed from the lower surface of the first substrate 21 and the upper surface of the second substrate 23. The first substrate 21 and second substrate 23 are fixed to each other via the sheet-like member 22 formed from a double-faced adhesive tape or the like, completing the flow cell 20 having the inlet port 24, measurement fluidic channel 25, resistance fluidic channel 26, and suction pumps 27.

<Operation of Flow Cell>

The operation of the flow cell 20 according to the second embodiment will be explained.

Also in the second embodiment, similar to the first embodiment, a plurality of projections 233a are formed in the suction pump 27. A sample solution injected from the inlet port 24 is sucked by the suction pump 27, passes through the measurement fluidic channel 25 and resistance fluidic channel 26, and reaches the suction pump 27.

Also in the second embodiment, the ends 233a-1 of the projections 233a do not contact the sheet-like member 22, and a gap is formed between the ends 233a-1 and the sheet-like member 22, as shown in FIG. 7. The internal capacity of the suction pump 27 is increased by an amount by which the projections 233a are shortened, compared to a conventional structure in which pillars are formed to connect the ceiling and bottom of the cavity of a capillary pump. The capacity of the suction pump 27 can thus be increased without enlarging the planar shape. Since the ends 233a-1 of the projections 233a, and portions of the first substrate 21 that abut against the ends 233a-1 in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 27 may be clogged with the impurity in a conventional structure. However, since the ends 233a-1 of the projections 233a do not contact the first substrate 21, a gap is formed between them, as described above, allowing the impurity to pass through the gap. Clogging of the inside of the suction pump 27 with the impurity can be prevented, realizing a stable operation.

In the second embodiment, a gap is formed between the ends 233a-1 and the sheet-like member 22 by forming the short projections 233a on the second substrate 23. However, the structure for forming the gap is not limited to this and can be freely set. For example, an opening 223 corresponding to the planar shape of the recess 233 may be formed in the sheet-like member 22, like a flow cell 30 shown in FIGS. 9 and 10. In this case, a gap is formed between the ends 233a-1 and the first substrate 21 without forming the short projections 233a on the second substrate 23. Even this structure can obtain the same operation effects as those of the flow cell 20 shown in FIGS. 6 and 7.

Figure 9:
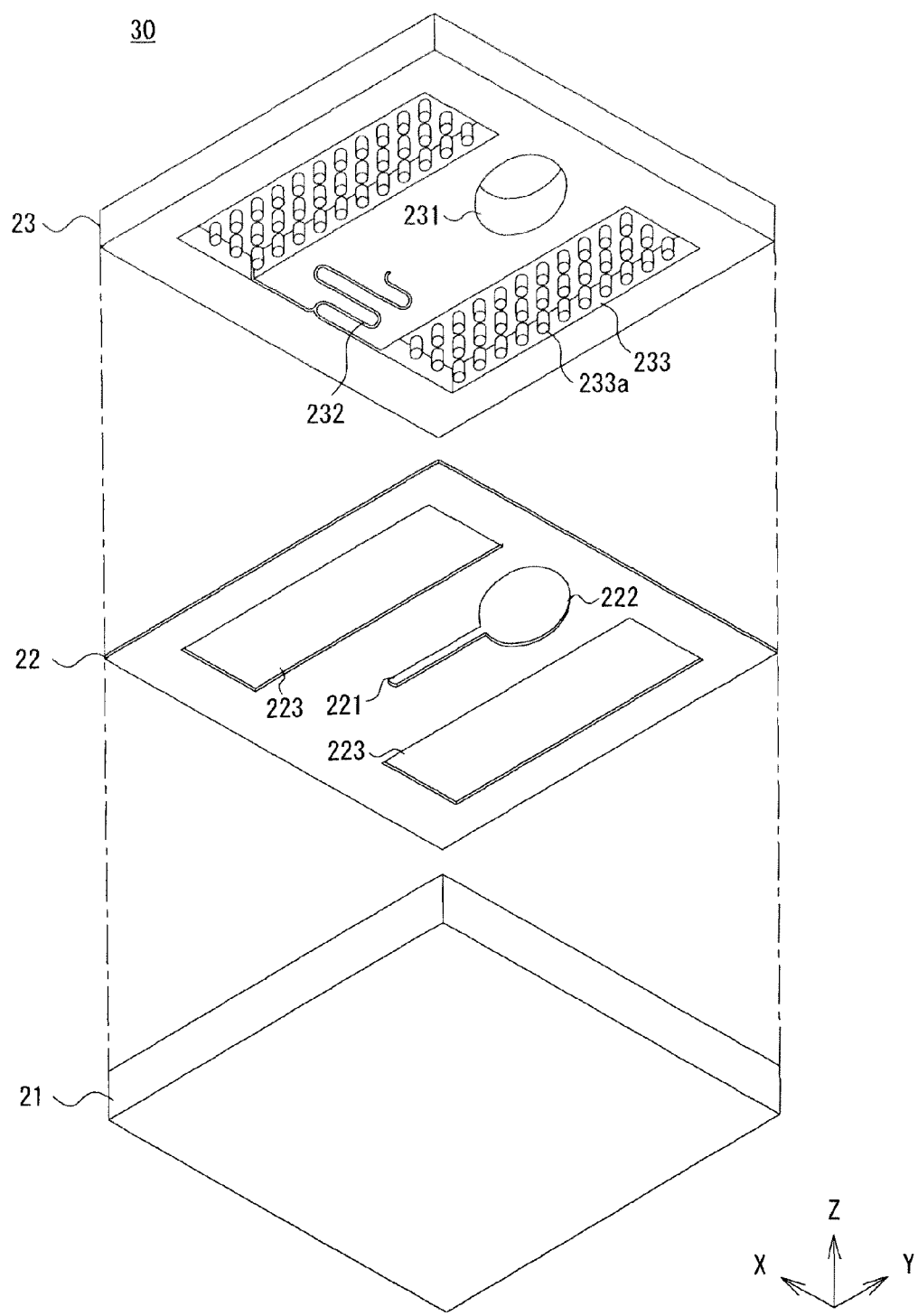
FIG. 9 is an exploded perspective view of a flow cell according to another embodiment of the present invention when viewed from the bottom.
Figure 10:
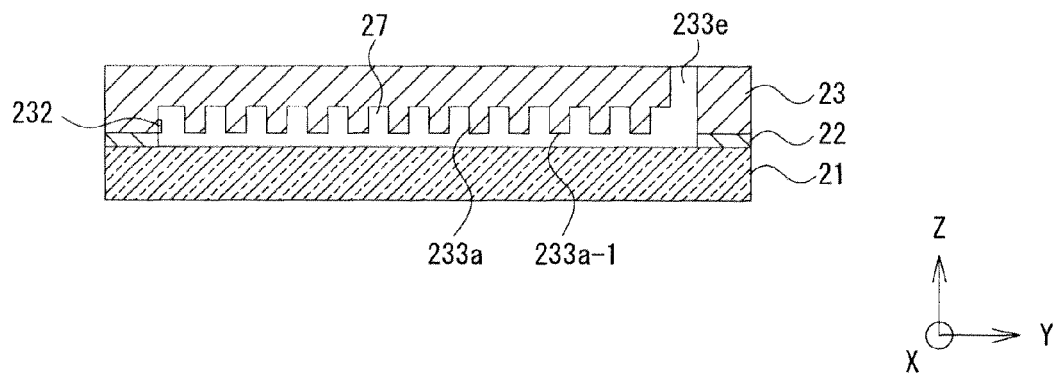
FIG. 10 is a sectional view of the main part of the flow cell in FIG. 9.

In the flow cell 30 shown in FIGS. 9 and 10, the slit 221 may be formed not in the sheet-like member 22 but in the second substrate 23. The depth of the measurement fluidic channel 25 is determined by a depth to which the slit 221 is formed in the second substrate 23. The distance between the end 233a-1 of the projection 233a of the suction pump 27 and the first substrate 21 is determined by the thickness of the sheet-like member 22. The depth of the measurement fluidic channel 25 and the distance between the end 233a-1 and the first substrate 21 can be set independently, and can be set more easily to desired sizes.

In the second embodiment, the slit 221 has an almost rectangular shape when viewed from the top, and is formed at almost the center of the sheet-like member 22. However, the shape and formation position of the slit 221 are not limited to them and can be freely set as long as the slit 221 passes above the Au layer 21a. Even the shape and position of the measurement fluidic channel 25 defined by the slit 221 can be freely set.

In the second embodiment, the opening 222 has an almost circular shape when viewed from the top. However, the shape of the opening 222 is not limited to this and can be freely set as long as the opening 222 exists at a position where it is connected to the through hole 231 of the second substrate 23.

In the second embodiment, the resistance fluidic channel 26 is arranged, but may be omitted.

<Application Example of Flow Cell>

An application example of the flow cell exemplified in each of the first and second embodiments will be described briefly. The flow cell is applied to measurement using a well-known surface plasmon resonance phenomenon (reference 5: Japanese Patent Laid-Open No. 2001-194298, and reference 6: Japanese Patent Laid-Open No. 2002-214131). Measurement using the surface plasmon resonance phenomenon utilizes resonance of an evanescent wave and surface plasmon wave on a metal surface in contact with an analyte to be measured.

Figure 11:
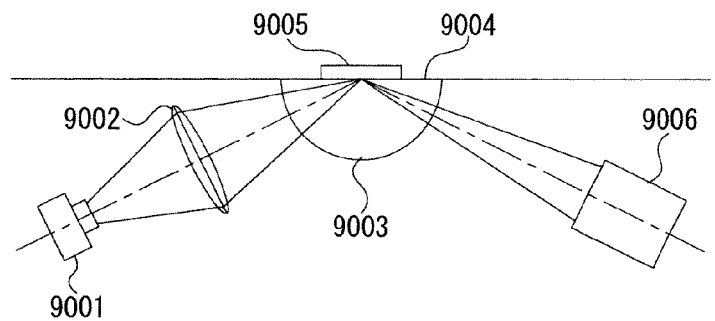
FIG. 11 is a view exemplifying the arrangement of an SPR measurement apparatus.
Figure 12:
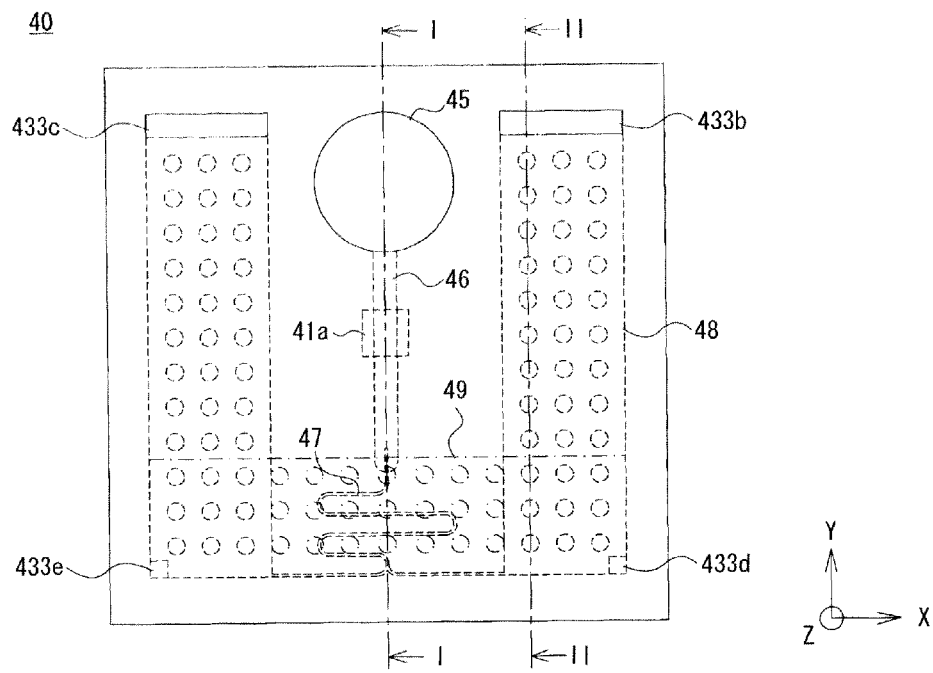
FIG. 12 is a plan view exemplifying the structure of a flow cell according to the third embodiment of the present invention.
Figure 13:
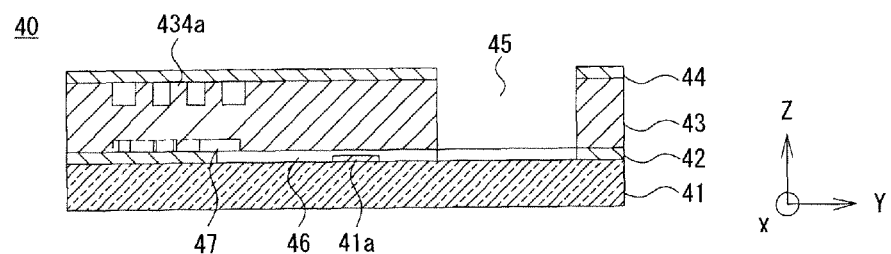
FIG. 13 is a sectional view taken along the line I-I in FIG. 12.
Figure 14:
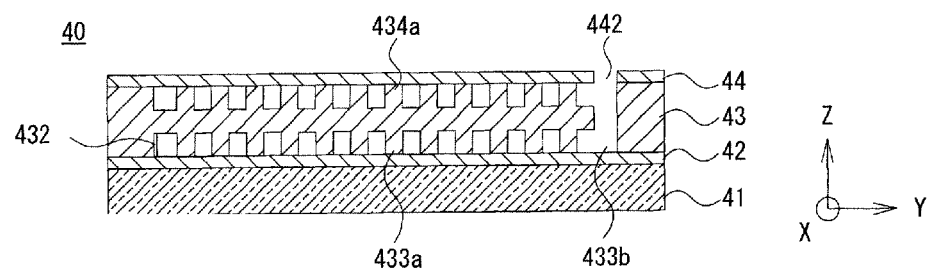
FIG. 14 is a sectional view taken along the line II-II in FIG. 12.
Figure 15:
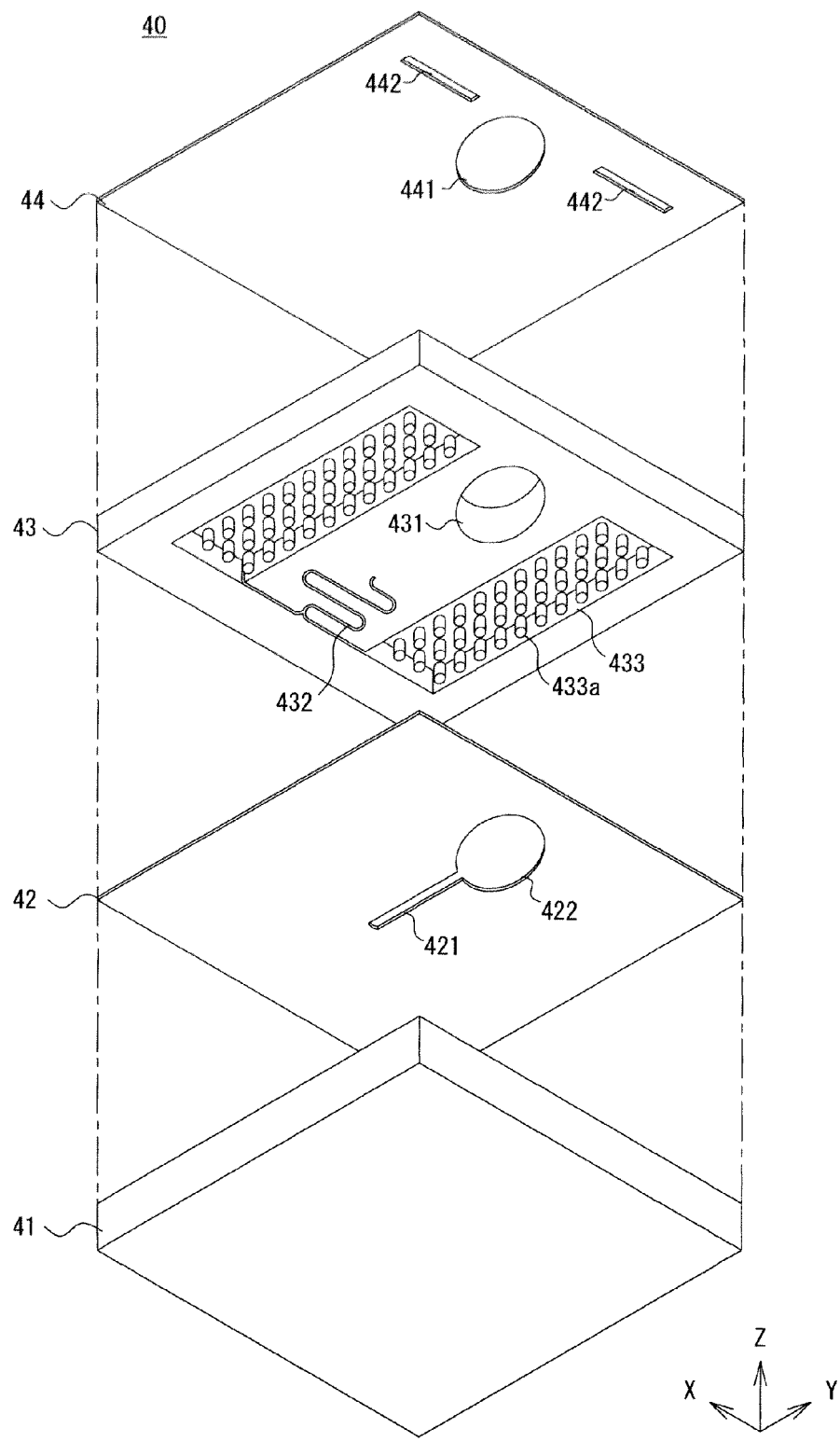
FIG. 15 is an exploded perspective view of the flow cell in FIG. 13 when viewed from the bottom.

In this measurement, as shown in FIG. 11, light emitted by a light source 9001 is focused by an entrance lens 9002 and enters a prism 9003. The light irradiates the Au film of a flow cell 9005 in tight contact with a measuring portion 9004 of the prism 9003. An analyte is set in contact with the surface of the Au thin film. The focused light which passed through the flow cell 9005 irradiates the lower surface of the Au thin film. The irradiated and focused light is reflected by the lower surface of the Au thin film. A photodetector 9006 formed from an image sensing element such as a CCD image sensor measures the intensity (light intensity). Then, a dip exhibiting a decrease in reflectance is observed at an angle at which the resonance occurs.

This measurement detects the presence/absence of an analyte which selectively binds to an antibody or DNA fragment immobilized on the surface (on the side of a detecting portion) of the Au film. In a state in which a sample solution is set at the detecting portion, a change caused by a reaction between the target analyte and the antibody and a change caused by a foreign substance settled and deposited at the detecting portion cannot be discriminated. Considering this, the sample solution is kept flowing at the detecting portion, suppressing sedimentation of a foreign substance. The change caused by a reaction can be selectively detected.

Third Embodiment

The third embodiment according to the present invention will be described in detail.

<Structure of Flow Cell>

As shown in FIGS. 12 to 16, a flow cell 40 according to the third embodiment is formed from a first substrate 41 which has an almost rectangular shape when viewed from the top, a first sheet-like member 42 which is disposed on the first substrate 41, a second substrate 43 which is disposed on the first sheet-like member 42, and a second sheet-like member 44 which is disposed on the second substrate 43. The flow cell 40 configured by stacking the substrates and sheet-like members includes an inlet port 45 which passes through the first sheet-like member 42, second substrate 43, and second sheet-like member 44 and allows introducing a sample solution, first suction pumps 48 which are formed between the first sheet-like member 42 and the second substrate 43, a second suction pump 49 which is formed between the second substrate 43 and the second sheet-like member 44, and a fluidic channel which connects the first suction pumps 48 and the inlet port 45. The fluidic channel is made up of a measurement fluidic channel 46 which has one end connected to the inlet port 45, is formed in the first sheet-like member 42, and irradiated with measurement light or the like by an external device, and a resistance fluidic channel 47 which has one end connected to the measurement fluidic channel 46 and the other end connected to the first suction pumps 48, and is formed between the first sheet-like member 42 and the second substrate 43.

<<First Substrate>>

The first substrate 41 is made of optical glass such as BK7, is about 1 mm in thickness, and has an almost rectangular shape about 16 mm on a side when viewed from the top. An Au layer 41*a* is formed by vapor deposition, sputtering, plating, or the like on the upper surface of the first substrate 41, i.e., a surface of the first substrate 41 on the side of the first sheet-like member 42. The Au layer 41*a* may be formed only at a portion corresponding to the measurement fluidic channel 46.

<<First Sheet-Like Member>>

The first sheet-like member 42 is formed from, e.g., a well-known adhesive tape about 10 μm to 150 μm in thickness, and has a planar shape corresponding to the first substrate 41. The first sheet-like member 42 has a slit 421 which is formed at almost the center and has an almost rectangular shape when viewed from the top, and an opening 422 which is connected to one end of the slit 421 and has an almost circular shape when viewed from the top. The slit 421 is formed so that its longitudinal direction becomes almost parallel to any one side of the first sheet-like member 42.

Together with the upper surface of the first substrate 41 and the lower surface of the second substrate 43, the slit 421 forms the measurement fluidic channel 46 which is an almost rectangular parallelepiped space. A section of the measurement fluidic channel 46 that is perpendicular to the longitudinal direction has dimensions enough to cause capillary actions with respect to an aqueous solution.

The first sheet-like member 42 can be fabricated by, for example, processing an adhesive tape into a desired shape by a cutter, laser, or the like.

<<Structure of Second Substrate>>

Figure 16:
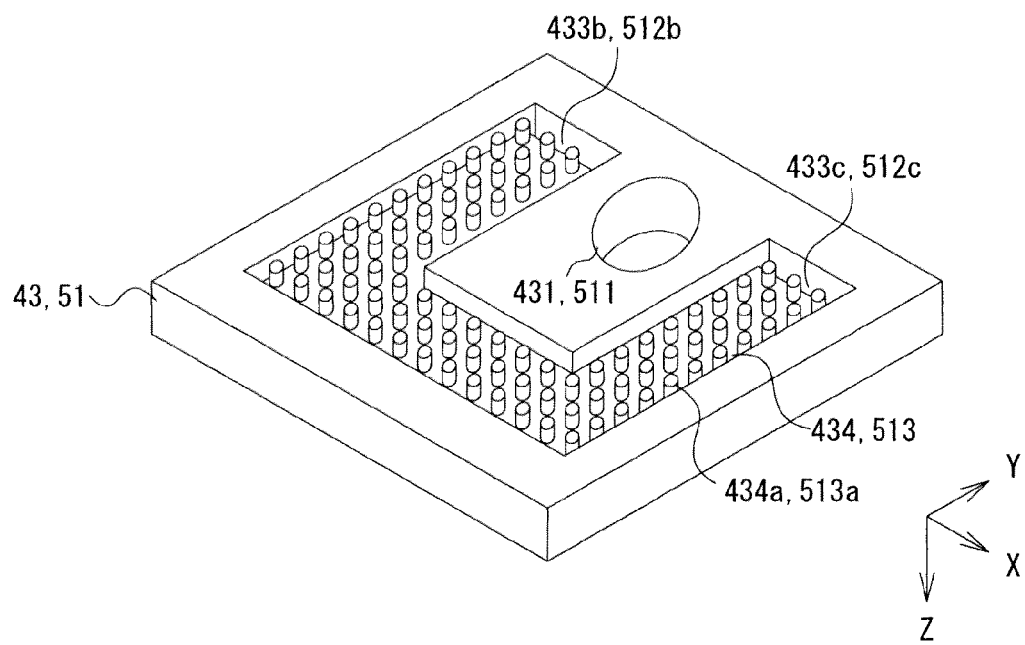
FIG. 16 is a perspective view of the second substrate when viewed from the top.

The second substrate 43 is formed from, e.g., an acrylic substrate about 0.5 to 5 mm in thickness, and has a planar shape corresponding to the first substrate 41 and first sheet-like member 42. A through hole 431 is formed near the center of the second substrate 43 on its one side. The lower surface of the second substrate 43 has a meandering channel 432 which is formed from almost the center to the vicinity of the other side opposite to the one side, and two first cavities 433 which are formed on the two sides of the meandering channel 432. As shown in FIG. 16, the upper surface of the second substrate 43 has a second cavity 434 formed around the through hole 431.

The through hole 431 has the same planar shape as that of the opening 422.

The meandering channel 432 has a crank-like planar shape with a plurality of bent portions. The bent portion is smoothly bent into an almost arcuate shape, i.e., curved shape. The other end of the meandering channel 432 branches near the other side of the second substrate 43. The branches extend in opposite directions in the perpendicular direction and are connected to the adjacent first cavities 433, respectively.

The two first cavities 433 are formed from the lower surface toward the upper surface of the second substrate 43. A plurality of almost columnar projections 433*a* are formed in each cavity and project downward from its ceiling. By setting the projections 433*a* to have an interval enough to cause capillary action, the first cavity 433 functions as the first suction pump 48. In the first cavities 433, vents 433*b* and 433*c* are formed at ends near the one side to connect the first cavities 433 and second cavity 434 to each other. Connection holes 433*d* and 433*e* are formed at corners near the other side that are opposite to those connected to the branches of the other end of the meandering channel 432.

The second cavity 434 is formed from the upper surface toward the lower surface of the second substrate 43 and has an almost "U" shape when viewed from the top. A plurality of almost columnar projections 434*a* are formed in the cavity and project upward from its bottom. By setting the projections 434*a* to have an interval enough to cause capillary action, the second cavity 434 functions as the second suction pump 49. The second cavity 434 is formed into an almost "U" shape when viewed from the top, so as to surround the center portion of the second substrate 43. One end of each of the vents 433*b* and 433*c* is connected to a corresponding one of two ends of the second cavity 434 near one side. One end of each of the connection holes 433*d* and 433*e* is connected to a corner near the other side.

Together with the upper surface of the first substrate 41, the opening 422, and an opening 441 (to be described later) of the second sheet-like member 44, the through hole 431 forms the inlet port 45 which is an almost columnar space with the upper surface of the first substrate defining its bottom.

When the second substrate 43 and first sheet-like member 42 are brought into contact with each other, the meandering channel 432 forms the meandering resistance fluidic channel 47. The resistance fluidic channel 47 has sectional dimensions enough to cause capillary action with respect to an aqueous solution.

The connection holes 433*d* and 433*e* have sectional dimensions enough to cause capillary action. The vents 433*b* and 433*c* have sectional dimensions larger than those of the connection holes 433*d* and 433*e*. Since the capillary force acting on a sample solution becomes small in the vents 433*b* and 433*c*, a sample solution preferentially flows through the connection holes 433*d* and 433*e*.

The second substrate 43 can be fabricated by injection molding using a mold having a predetermined pattern, laser processing, cutting using an end mill, or the like.

<<Second Sheet-Like Member>>

The second sheet-like member 44 is formed from, e.g., a well-known adhesive tape about 10 μm to 150 μm in thickness, and has a planar shape corresponding to the first substrate 41, first sheet-like member 42, and second substrate 43. The second sheet-like member 44 has the opening 441 which is formed near the one side and has an almost circular shape when viewed from the top, and two holes 442 which are formed on the two sides of the opening 441 and near the one side. The holes 442 are formed so that their longitudinal directions coincide with a direction in which the one side extends. The holes 442 have the same planar shape as that of the vents 433*b* and 433*c*.

The second sheet-like member 44 can be fabricated by, for example, processing an adhesive tape into a desired shape by a cutter, laser, or the like.

<Method of Manufacturing Flow Cell>

A method of manufacturing the flow cell 40 according to the third embodiment will be exemplified. First, the first sheet-like member 42 is placed on the first substrate 41. When the Au layer 41a is formed only at part of the first substrate 41, the first sheet-like member 42 is placed on the first substrate 41 so that the slit 421 for forming the measurement fluidic channel 46 is located on the Au layer 41a.

Then, the second substrate 43 is placed on the first sheet-like member 42 so that the through hole 431 and opening 422 are connected to each other and one end of the meandering channel 432 is positioned in the other end of the slit 421.

The second sheet-like member 44 is placed on the second substrate 43 so that the opening 441 and through hole 431 are connected to each other and the holes 442 are connected to the holes 433b and 433c.

After the first substrate 41, first sheet-like member 42, second substrate 43, and second sheet-like member 44 are stacked in this way, they are pressed from the lower surface of the first substrate 41 and the upper surface of the second sheet-like member 44. This fixes the first substrate 41 and second substrate 43 to each other via the first sheet-like member 42 formed from a double-faced adhesive tape or the like. At the same time, the second sheet-like member 44 covers the upper surface of the second substrate 43, completing the flow cell 40 having the inlet port 45, measurement fluidic channel 46, resistance fluidic channel 47, first suction pumps 48, and second suction pump 49.

<Operation of Flow Cell>

The operation of the flow cell 40 according to the third embodiment will be explained.

When a sample solution is injected from the inlet port 45, it proceeds sequentially through the measurement fluidic channel 46 and resistance fluidic channel 47 by capillary action, and flows into the first suction pumps 48. In the first suction pumps 48, a plurality of projections 433a are formed to increase the surface area per unit volume, compared to a structure in which no projection 433a is formed. The inside of the first suction pump 48 has dimensions enough to cause capillary action. The sample solution which has flowed into the first suction pumps 48 proceeds through their insides. Note that the flow rate changes depending on the shape of the first cavity 433 such as the outer shape and interval of the projection 433a, the resistance acting on the sample solution, and the like.

By capillary action, the sample solution which has reached the first suction pumps 48 proceeds through the insides of the first cavities 433 from the other end of the meandering channel 432 toward the vents 433b and 433c, in other words, from the other side to one side (positive direction in the Y direction) of the second substrate 43. Then, the sample solution reaches the connection holes 433d and 433e. The connection holes 433d and 433e are formed to have dimensions enough to cause capillary action. After the sample solution reaches the connection holes 433d and 433e, it passes through them and enters the second suction pump 49 configured by the second cavity 434 formed in the upper surface of the second substrate 43. After the sample solution enters the second suction pump 49, it proceeds toward the vents 433b and 433c, in other words, from the other side to one side (positive direction in the Y direction) of the second substrate 43, similar to that in the first suction pump 48. Hence, the sample solution proceeds through the insides of the first suction pumps 48 and second suction pump 49 in the positive direction in the Y direction.

The sample solution proceeds in the positive direction in the Y direction and reaches the vents 433b and 433c. The vents 433b and 433c are formed to be larger in sectional area than the connection holes 433d and 433e, and the capillary force hardly acts on a liquid present inside the vents 433b and 433c. When the sample solution reaches the vents 433b and 433c, it stops proceeding or proceeds only slightly inside them. As a result, the suction operation of the sample solution by the first suction pumps 48 and second suction pump 49 ends. At this time, air which has remained in the first suction pumps 48 and second suction pump 49 is released outside from the vents 433b and 433c because the sample solution uniformly proceeds in the positive direction in the Y direction, as described above. This can prevent air from remaining in the first suction pumps 48 and second suction pump 49.

As described above, according to the third embodiment, pumps are formed between the first and second substrates and between the second and third substrates, thereby increasing the pump capacity without enlarging the planar shape. More specifically, the first cavities 433 and second cavity 434 are formed in the lower and upper surfaces of the second substrate 43. The first suction pumps 48 are formed between the first sheet-like member 42 and the second substrate 43. The second suction pump 49 is formed between the second substrate 43 and the second sheet-like member 44. The suction pump capacity in the flow cell 40 can be increased in the direction of thickness of the second substrate 43. The pump capacity can be increased without enlarging the planar shape of the flow cell 40.

In the third embodiment, the slit 421 has an almost rectangular shape when viewed from the top, and is formed at almost the center of the sheet-like member 42. However, the shape and formation position of the slit 421 are not limited to them and can be freely set as long as the slit 421 extends on the Au layer 41a. Even the shape and position of the measurement fluidic channel 46 defined by the slit 421 can be freely set.

In the third embodiment, the opening 422 has an almost circular shape when viewed from the top. However, the shape of the opening 422 is not limited to this and can be freely set as long as the opening 422 exists at a position where it is connected to the through hole 431 of the second substrate 43. Similarly, the planar shapes of the through hole 431 and opening 441 are not limited to an almost circular shape and can be freely set.

In the third embodiment, the first cavity 433 has an almost rectangular shape when viewed from the top, and the second cavity 434 has an almost "U" shape when viewed from the top. However, the planar shapes of the first and second cavities 433 and 434 are not limited to them and can be freely set. Similarly, the shapes of the projections 433a and 434a formed in the first and second cavities 433 and 434 are not limited to an almost columnar shape and can be freely set as long as the surface areas in the first and second cavities 433 and 434 are increased.

In the third embodiment, the resistance fluidic channel 47 is arranged, but the measurement fluidic channel 46 and first suction pump 48 may be directly connected without arranging the resistance fluidic channel 47. Also, the shape of the resistance fluidic channel 47, i.e., that of the meandering channel 432 is not limited to the above-mentioned crank shape and can be freely set.

In the third embodiment, the first sheet-like member 42 is arranged but may be omitted. In this case, the slit formed in the first sheet-like member 42 is formed in the first substrate 41 or second substrate 43. A member to engage with the sides of the first substrate 41 and second substrate 43 is attached to join them. Alternatively, the first substrate 41 and second substrate 43 are bonded to each other using an adhesive or the like.

Fourth Embodiment

The fourth embodiment according to the present invention will be described in detail. In the fourth embodiment, the flow cell described in the third embodiment further includes the third substrate and third sheet-like member. In the fourth embodiment, the same reference numerals as those in the third embodiment denote the same parts, and a description thereof will be properly omitted.

<Structure of Flow Cell>

Figure 17:
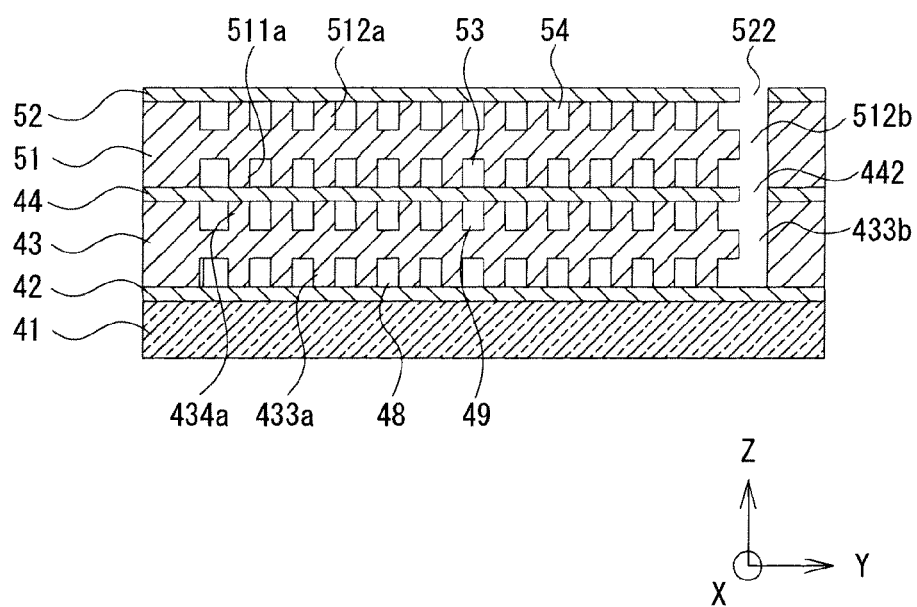
FIG. 17 is a sectional view exemplifying the structure of the main part of a flow cell according to the fourth embodiment of the present invention.
Figure 18:
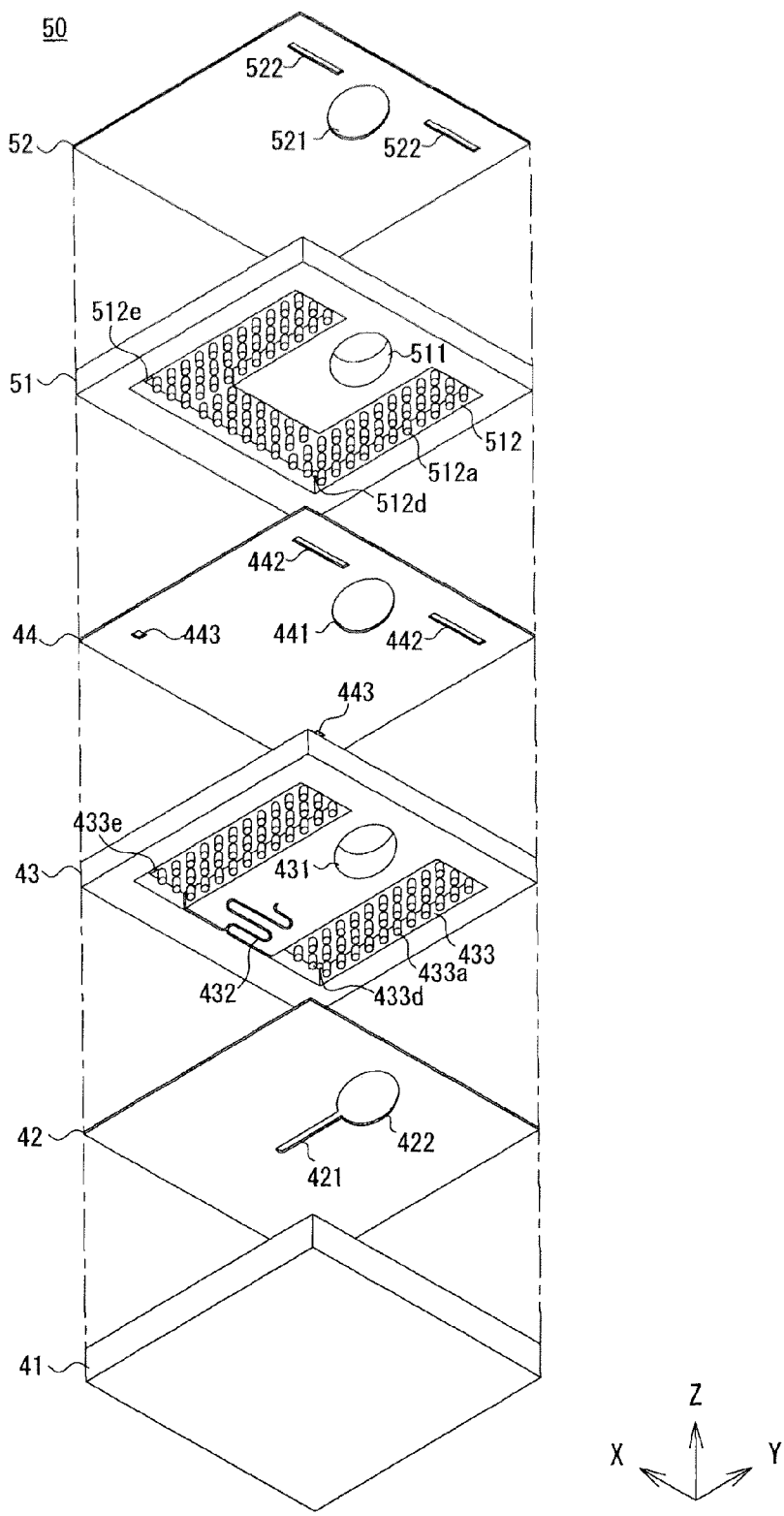
FIG. 18 is an exploded perspective view of the flow cell in FIG. 17 when viewed from the bottom.

As shown in FIGS. 16 to 18, a flow cell 50 according to the fourth embodiment is formed from a first substrate 41 which has an almost rectangular shape when viewed from the top, a first sheet-like member 42 which is disposed on the first substrate 41, a second substrate 43 which is disposed on the first sheet-like member 42, a second sheet-like member 44 which is disposed on the second substrate 43, a third substrate 51 which is disposed on the second sheet-like member 44, and a third sheet-like member 52 which is disposed on the third substrate 51. The flow cell 50 configured by stacking the substrates and sheet-like members includes an inlet port 45 which passes through the first sheet-like member 42, second substrate 43, second sheet-like member 44, third substrate 51, and third sheet-like member 52 and allows introducing a sample solution, first suction pumps 48 which are formed between the first sheet-like member 42 and the second substrate 43, a second suction pump 49 which is formed between the second substrate 43 and the second sheet-like member 44, a third suction pump 53 which is formed between the second sheet-like member 44 and the third substrate 51, a fourth suction pump 54 which is formed between the third substrate 51 and the third sheet-like member 52, and a fluidic channel which connects the first suction pumps 48 and the inlet port 45. The fluidic channel is made up of a measurement fluidic channel 46 which has one end connected to the inlet port 45, is formed in the first sheet-like member 42, and irradiated with measurement light or the like by an external device, and a resistance fluidic channel 47 which has one end connected to the measurement fluidic channel 46 and the other end connected to the first suction pumps 48, and is formed between the first sheet-like member 42 and the second substrate 43.

<<Second Sheet-Like Member>>

As described above, the second sheet-like member 44 has an opening 441 which has a planar shape corresponding to the first substrate 41, first sheet-like member 42, and second substrate 43, is formed near the one side, and has an almost circular shape when viewed from the top, and two holes 442 which are formed on the two sides of the opening 441 and near the one side. The second sheet-like member 44 also has connection holes 443 which are formed on the two sides of the opening 441 and near the other side. The connection holes 443 have dimensions enough to cause capillary action.

<<Structure of Third Substrate>>

The third substrate 51 is formed from, e.g., an acrylic transparent substrate about 0.5 to 5 mm in thickness, and has a planar shape corresponding to the first substrate 41 and the like. A through hole 511 is formed near the center of the third substrate 51 on its one side. The lower surface of the third substrate 51 has a third cavity 512 which is formed around the through hole 511. The upper surface of the third substrate 51 has a fourth cavity 513 which is formed around the through hole 511.

The third cavity 512 is formed from the lower surface toward the upper surface of the third substrate 51 and has an almost "U" shape when viewed from the top. A plurality of almost columnar projections 512a are formed in the cavity and project downward from its ceiling. By setting the projections 512a to have an interval enough to cause capillary action, the third cavity 512 functions as the third suction pump 53. The third cavity 512 is formed into an almost "U" shape when viewed from the top, so as to surround the center portion of the third substrate 51. In the third cavity 512, vents 512b and 512c are formed at ends near the one side of the third substrate 51, and connected to the third cavity 512 and fourth cavity 513. Further, connection holes 512d and 512e are formed at corners near the other side.

As shown in FIG. 16, the fourth cavity 513 is formed from the upper surface toward the lower surface of the third substrate 51 and has an almost "U" shape when viewed from the top. A plurality of almost columnar projections 513a are formed in the cavity and project upward from its bottom. By setting the projections 513a to have an interval enough to cause capillary action, the fourth cavity 513 functions as the fourth suction pump 54. The fourth cavity 513 is formed into an almost "U" shape when viewed from the top. The vents 512b and 512c are connected to ends of the fourth cavity 513 near the one side. One end of each of the connection holes 512d and 512e is connected to a corner near the other side.

The third substrate 51 can be fabricated by injection molding using a mold having a predetermined pattern, laser processing, cutting using an end mill, or the like.

<<Third Sheet-Like Member>>

The third sheet-like member 52 is formed from, e.g., a well-known adhesive tape about 10 μm to 150 μm in thickness, and has a planar shape corresponding to the first substrate 41 and the like. The third sheet-like member 52 has an opening 521 which is formed near one side and has an almost circular shape when viewed from the top, and two holes 522 which are formed on the two sides of the opening 521 and near the one side. The holes 522 have the same shape as that of the vents 433b and 433c.

The third sheet-like member 52 can be fabricated by, for example, processing an adhesive tape into a desired shape by a cutter, laser, or the like.

<Method of Manufacturing Flow Cell>

A method of manufacturing the flow cell 50 according to the fourth embodiment will be exemplified. First, the first substrate 41, first sheet-like member 42, second substrate 43, and second sheet-like member 44 are stacked by the same procedures as those in the first embodiment.

Then, the third substrate 51 is placed on the second sheet-like member 44 so that the through hole 511 and opening 441 are connected to each other, ends of the third cavity 512 near the one side are connected to the corresponding holes 442, and the connection holes 512d and 512e are connected to the connection holes 443.

The third sheet-like member 52 is placed on the third substrate 51 so that the opening 521 and through hole 511 are connected to each other, and the holes 522 and vents 512b and 512c are connected to each other.

After the first substrate 41, first sheet-like member 42, second substrate 43, second sheet-like member 44, third substrate 51, and third sheet-like member 52 are stacked in this manner, they are pressed from the lower surface of the first substrate 41 and the upper surface of the third sheet-like member 52. This fixes the first substrate 41 and second substrate 43 to each other via the first sheet-like member 42 formed from a double-faced adhesive tape or the like, and the second substrate 43 and third substrate 51 to each other via the second sheet-like member 44 formed from a double-faced adhesive tape or the like. In addition, the third sheet-like member 52 covers the upper surface of the third substrate 51, completing the flow cell 50 having the inlet port 45, measurement fluidic channel 46, resistance fluidic channel 47, first suction pumps 48, second suction pump 49, third suction pump 53, and fourth suction pump 54.

At this time, the connection holes 433d and 433e of the second substrate 43, the two connection holes 443 of the second sheet-like member 44, and the connection holes 512d and 512e of the third substrate 51 are connected to each other in the Z direction. Similarly, the vents 433b and 433c of the second substrate 43, the holes 442 of the second sheet-like member 44, the vents 512b and 512c of the third substrate 51, and the holes 522 of the third sheet-like member 52 are connected to each other in the Z direction.

<Operation of Flow Cell>

The operation of the flow cell 50 according to the fourth embodiment will be explained.

As described above, when a sample solution is injected from the inlet port 45, it proceeds sequentially through the measurement fluidic channel 46 and resistance fluidic channel 47 by capillary action, and flows into the first suction pumps 48. In the first suction pumps 48, a plurality of projections 433a are formed to increase the surface area per unit volume, compared to a structure in which no projection 433a is formed. The inside of the first suction pump 48 has dimensions enough to cause capillary action. The sample solution which has flowed into the first suction pumps 48 proceeds through their insides. Note that the flow rate changes depending on the shape of the cavity 433 such as the outer shape and interval of the projection 433a, the resistance acting on the sample solution, and the like.

By capillary action, the sample solution which has reached the first suction pumps 48 proceeds through the insides of the first cavities 433 from the other end of the meandering channel 432 toward the vents 433b and 433c, in other words, from the other side to one side (positive direction in the Y direction) of the second substrate 43. Then, the sample solution reaches the connection holes 433d and 433e. The connection holes 433d and 433e are formed to have dimensions enough to cause capillary action. After the sample solution reaches the connection holes 433d and 433e, it passes through them and enters the second suction pump 49 configured by the second cavity 434 formed in the upper surface of the second substrate 43.

The two connection holes 443 of the second sheet-like member 44 are formed above the connection holes 433d and 433e and connected to them. The sample solution which has entered the second cavity 434 through the connection holes 433d and 433e enters, through the connection holes 443, the third suction pump 53 configured by the third cavity 512 formed in the lower surface of the third substrate 51.

Similarly, the connection holes 512d and 512e of the third substrate 51 are formed above the connection holes 443 and connected to them. The sample solution which has entered the third suction pump 53 enters, through the connection holes 512d and 512e, the fourth suction pump 54 configured by the fourth cavity 513 formed in the upper surface of the third substrate 51.

The sample solution which has entered the first suction pumps 48, second suction pump 49, third suction pump 53, and fourth suction pump 54 proceeds through their insides in the positive direction in the Y direction.

The sample solution proceeds in the positive direction in the Y direction and reaches the vents 433b and 433c or vents 512b and 512c. The vents 433b, 433c, 512b, and 512c are formed to be larger in sectional area than the connection holes 433d, 433e, 512d, and 512e, and the capillary force hardly acts on a liquid present inside the vents 433b, 433c, 512b, and 512c. Thus, when the sample solution reaches the vents 433b, 433c, 512b, and 512c, it stops proceeding or proceeds only slightly inside them. Accordingly, the suction operation of the sample solution by the first suction pumps 48, second suction pump 49, third suction pump 53, and fourth suction pump 54 ends. At this time, air which has remained in the first suction pumps 48, second suction pump 49, third suction pump 53, and fourth suction pump 54 is released outside via the vents 433b, 433c, 512b, and 512c because the sample solution uniformly proceeds in the positive direction in the Y direction, as described above. This can prevent air from remaining in the first suction pumps 48, second suction pump 49, third suction pump 53, and fourth suction pump 54.

As described above, according to the fourth embodiment, the first substrate 41, first sheet-like member 42, second substrate 43, second sheet-like member 44, third substrate 51, and third sheet-like member 52 are stacked. The first suction pumps 48 are formed between the first sheet-like member 42 and the second substrate 43. The second suction pump 49 is formed between the second substrate 43 and the second sheet-like member 44. The third suction pump 53 is formed between the second sheet-like member 44 and the third substrate 51. The fourth suction pump 54 is formed between the third substrate 51 and the third sheet-like member 52. The suction pump capacity in the flow cell 50 can be increased in the direction of thickness of the second substrate 43 and the like. The pump capacity can be increased without enlarging the planar shape of the flow cell 50.

In the fourth embodiment, cavities are formed in the two surfaces of the third substrate 51, but a cavity may be formed in only the lower surface.

In the fourth embodiment, the first substrate 41, first sheet-like member 42, second substrate 43, second sheet-like member 44, third substrate 51, and third sheet-like member 52 are stacked. However, a sheet-like member and substrate may be further stacked in accordance with the pump capacity. In this case, a necessary number of pairs each of the second sheet-like member 44 and third substrate 51 are stacked on the third substrate 51 in accordance with the pump capacity. The third sheet-like member 52 is stacked on the uppermost third substrate 51. A flow cell with a larger-capacity pump can be realized.

Figure 19:
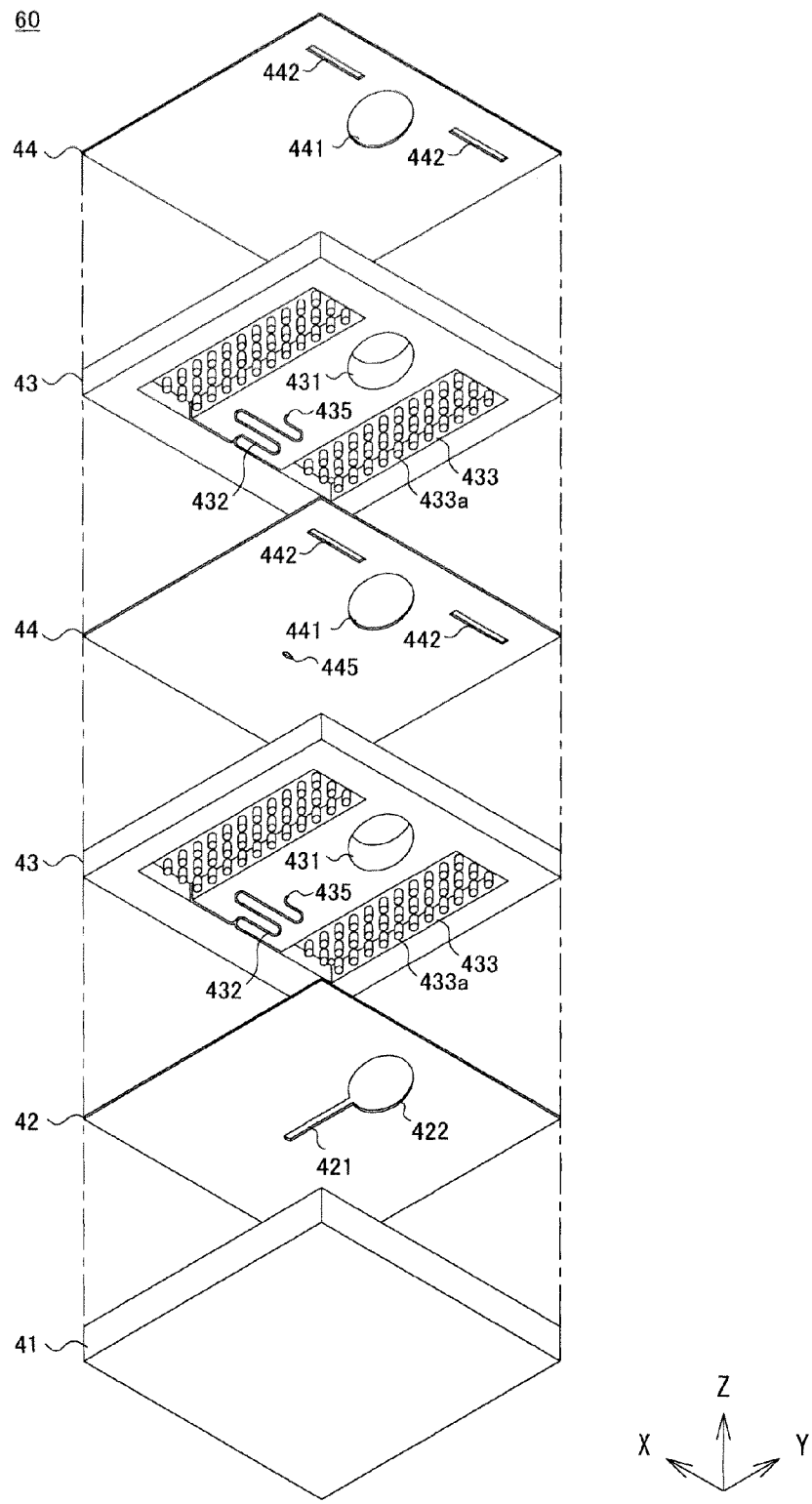
FIG. 19 is an exploded perspective view of another flow cell according to the present invention when viewed from the bottom.

As shown in FIG. 19, the second substrate 43 and second sheet-like member 44 may be stacked on the second sheet-like member 44 in the flow cell 40 described in the third embodiment. In this case, through holes 435 and 445 may be formed in the second substrate 43 and second sheet-like member 44 to be connected to each other. More specifically, the through hole 435 is formed in the second substrate 43 to pass from the open end of the meandering channel 432 in the Z direction. The through hole 445 is formed in the second sheet-like member 44 at a position corresponding to the through hole 435 when the second sheet-like member 44 is placed on the second substrate 43. The through holes 435 and 445 have dimensions enough to cause capillary action. In a flow cell 60 having this structure, when a sample solution is injected from the inlet port 45, it passes through the measurement fluidic channel 46 and reaches the resistance fluidic channel 47. The sample solution proceeds through the resistance fluidic channel 47, and enters the first suction pumps 48 and second suction pump 49 via the through hole 435 formed at one end of the resistance fluidic channel 47 and the through hole 445 which is formed in the second sheet-like member 44 and connected to the through hole 435. Then, the sample solution proceeds in the positive direction in the Y direction. Even this structure can increase the suction pump capacity in the flow cell 60 in the direction of thickness of the second substrate 43. As a result, the pump capacity can be increased without enlarging the planar shape of the flow cell 60.

In FIG. 19, the through hole 445 may not be formed in the uppermost second sheet-like member 44.

Fifth Embodiment

The fifth embodiment according to the present invention will be described in detail. In the fifth embodiment, the ends of the projections 433a and 434a in the flow cell 40 described in the third embodiment are formed as open ends. In the fifth embodiment, the same reference numerals as those in the third embodiment denote the same parts, and a description thereof will be properly omitted.

<Structure of Flow Cell>

Figure 20:
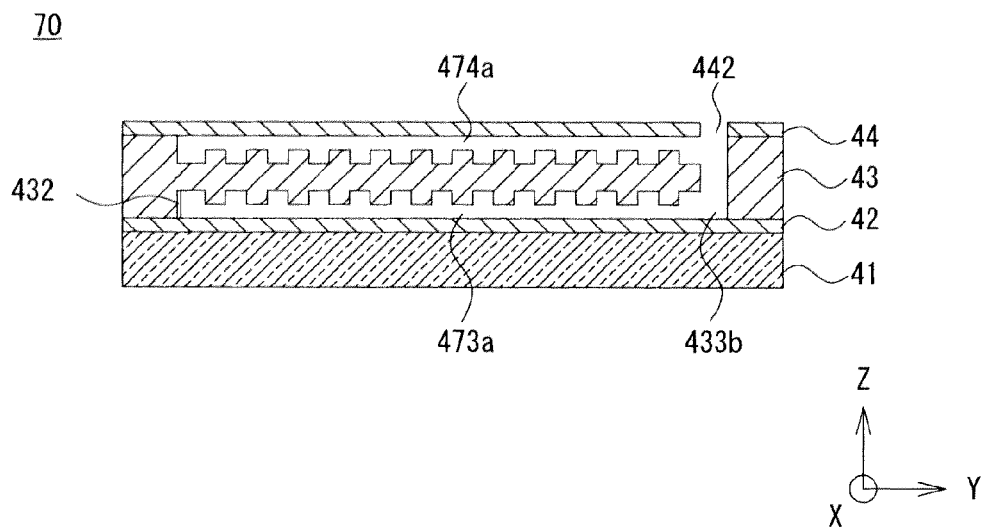
FIG. 20 is a sectional view exemplifying the structure of the main part of a flow cell according to the fifth embodiment of the present invention.

As shown in FIG. 20, a flow cell 70 according to the fifth embodiment is formed from a first substrate 41, a first sheet-like member 42 which is disposed on the first substrate 41, a second substrate 43 which is disposed on the first sheet-like member 42, and a second sheet-like member 44 which is disposed on the second substrate 43. Similar to the flow cell 40 described in the third embodiment, the flow cell 70 configured by stacking the substrates and sheet-like members includes an inlet port 45 which passes through the first sheet-like member 42, second substrate 43, and second sheet-like member 44 and allows introducing a sample solution, first suction pumps 48 which are formed between the first sheet-like member 42 and the second substrate 43, a second suction pump 49 which is formed between the second substrate 43 and the second sheet-like member 44, and a fluidic channel which connects the first suction pumps 48 and the inlet port 45. The fluidic channel is made up of a measurement fluidic channel 46 which has one end connected to the inlet port 45, is formed in the first sheet-like member 42, and irradiated with measurement light or the like by an external device, and a resistance fluidic channel 47 which has one end connected to the measurement fluidic channel 46 and the other end connected to the first suction pumps 48, and is formed between the first sheet-like member 42 and the second substrate 43.

<<Structure of Second Substrate>>

The second substrate 43 has a through hole 431 which is formed near the center on the one side, a meandering channel 432 which is formed from almost the center of the lower surface to the vicinity of the other side opposite to the one side, two first cavities 433 which are formed on the two sides of the meandering channel 432, and a second cavity 434 which is formed around the through hole 431 in the upper surface.

The two first cavities 433 are formed from the lower surface toward the upper surface of the second substrate 43 and have an almost rectangular shape when viewed from the top. A plurality of almost columnar projections 473a are formed in each cavity and project downward from its ceiling. The end of the projection 473a is formed to be located at a level vertically higher than the lower surface of the second substrate 43 when the second substrate 43 is placed on a horizontal surface. When the second substrate 43 is placed on the first sheet-like member 42, the projections 473a have open ends, i.e., do not contact the first sheet-like member 42, forming a space between them. At this time, the distance between the end of the projection 473a and the first sheet-like member 42 and the interval between the projections 473a are set to cause capillary action. With this setting, the first cavities 433 function as the first suction pumps 48.

The second cavity 434 is formed from the upper surface toward the lower surface of the second substrate 43 and has an almost "U" shape when viewed from the top. A plurality of almost columnar projections 474a are formed in the cavity and project upward from its bottom. The end of the projection 474a is formed to be located at a level vertically lower than the upper surface of the second substrate 43 when the second substrate 43 is placed on a horizontal surface. When the second sheet-like member 44 is placed on the second substrate 43, the projections 474a have open ends, i.e., the ends of the projections 474a do not contact the second sheet-like member 44, forming a space between them. At this time, the distance between the end of the projection 474a and the second sheet-like member 44 and the interval between the projections 474a are set to cause capillary action. The second cavity 434 functions as the second suction pump 49.

With this structure, the flow cell 70 according to the fifth embodiment becomes larger in the internal capacity of each suction pump than the flow cell 40 described in the third embodiment, and the capacity of each suction pump can be increased. Since the ends of the projections, and portions of the sheet-like member that abut against the ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump may be clogged with the impurity in a conventional structure. However, since the ends of the projections do not contact the sheet-like member, a gap is formed between them, as described above. The impurity can pass through the gap, preventing clogging of the inside of the suction pump with the impurity.

Sixth Embodiment

The sixth embodiment according to the present invention will be described in detail. In the sixth embodiment, the ends of the projections 433a, 434a, 512a, and 513a in the flow cell 50 described in the fourth embodiment are formed as open ends. In the sixth embodiment, the same reference numerals as those in the fourth embodiment denote the same parts, and a description thereof will be properly omitted.

<Structure of Flow Cell>

Figure 21:
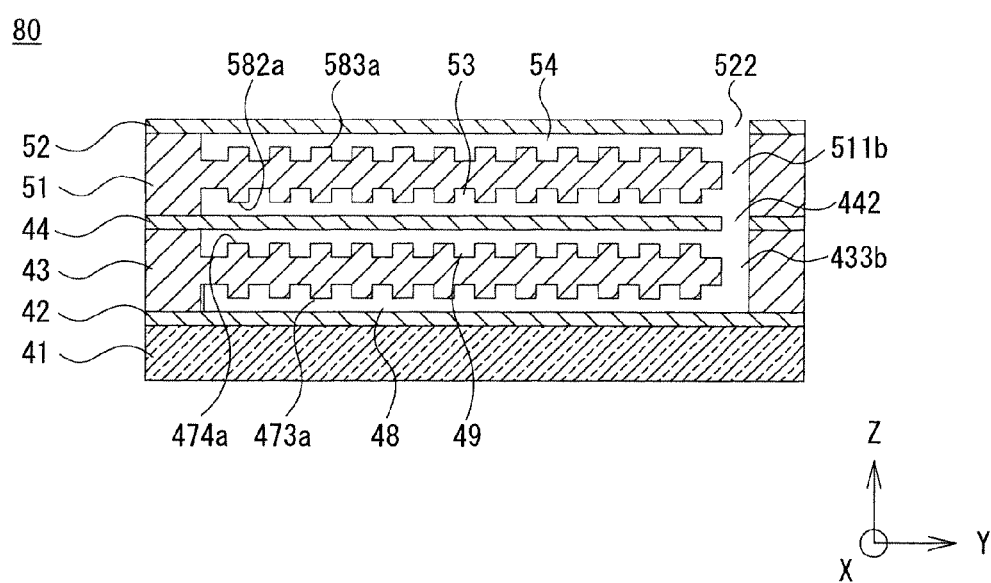
FIG. 21 is a sectional view exemplifying the structure of the main part of a flow cell according to the sixth embodiment of the present invention.
Figure 22:
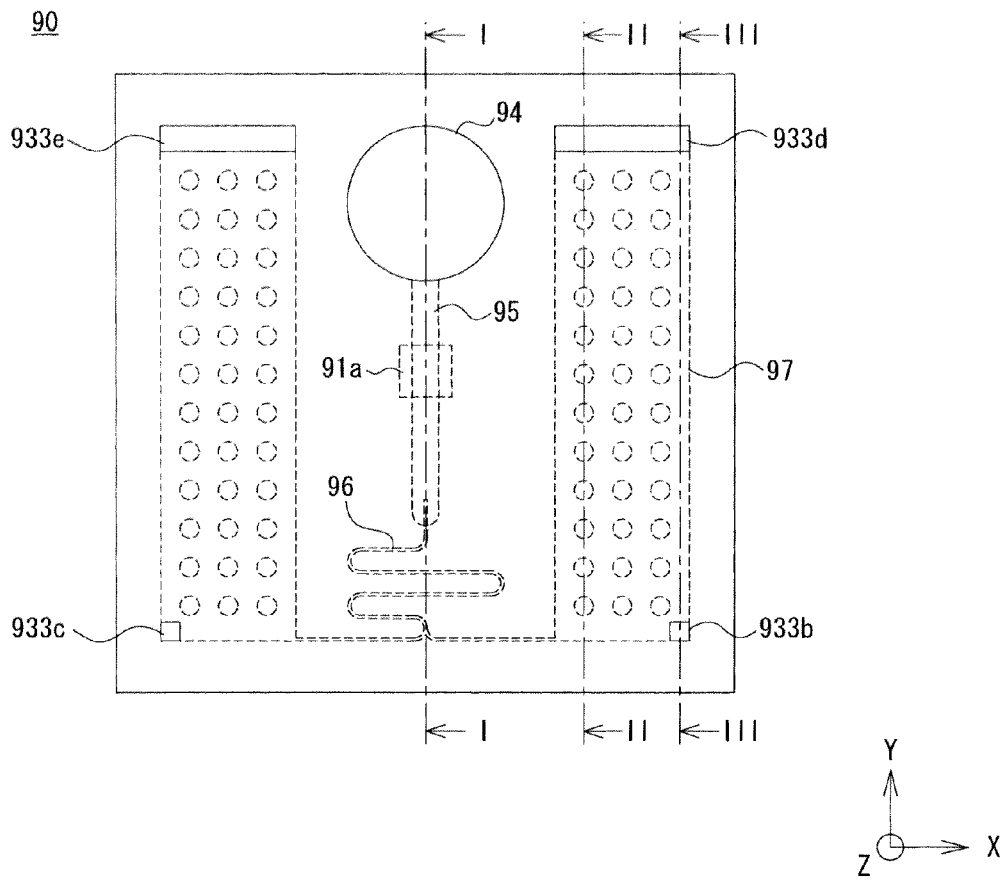
FIG. 22 is a plan view exemplifying the structure of a flow cell according to the seventh embodiment of the present invention.
Figure 23:
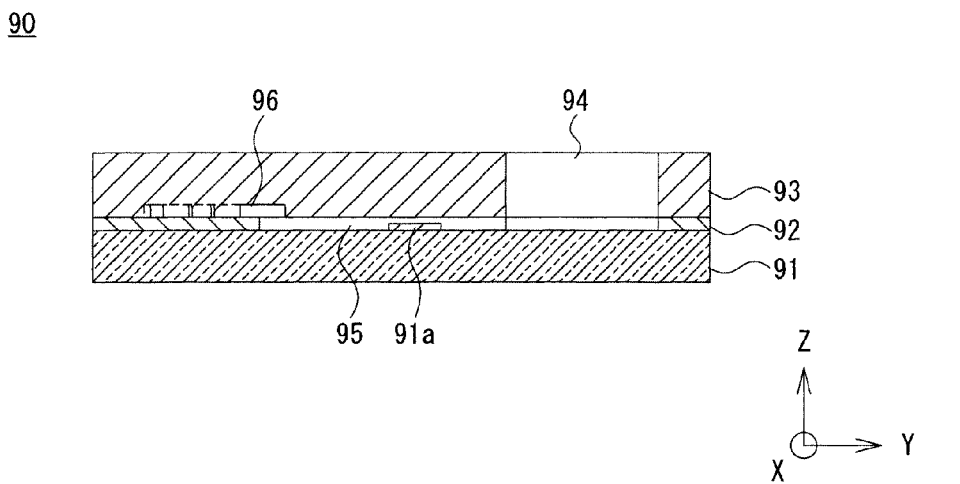
FIG. 23 is a sectional view taken along the line I-I in FIG. 22.
Figure 24:
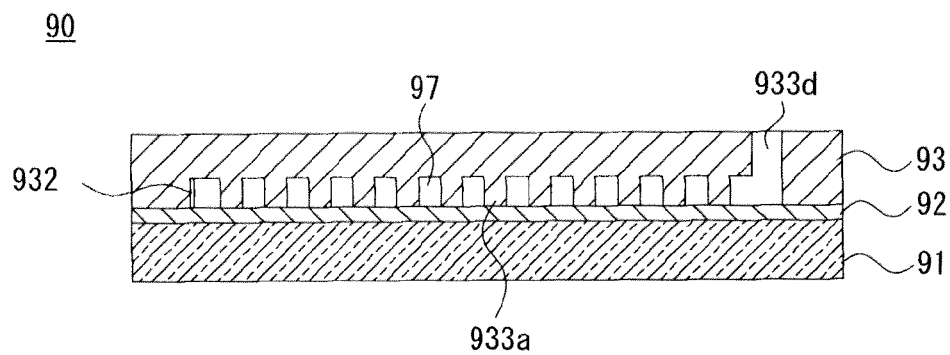
FIG. 24 is a sectional view taken along the line II-II in FIG. 22.
Figure 25:
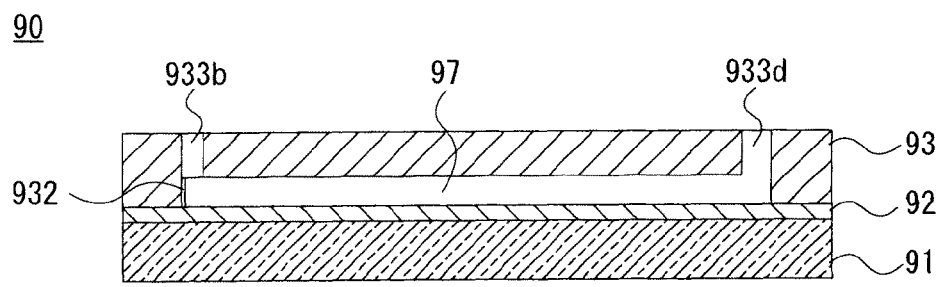
FIG. 25 is a sectional view taken along the line III-III in FIG. 22.
Figure 26:
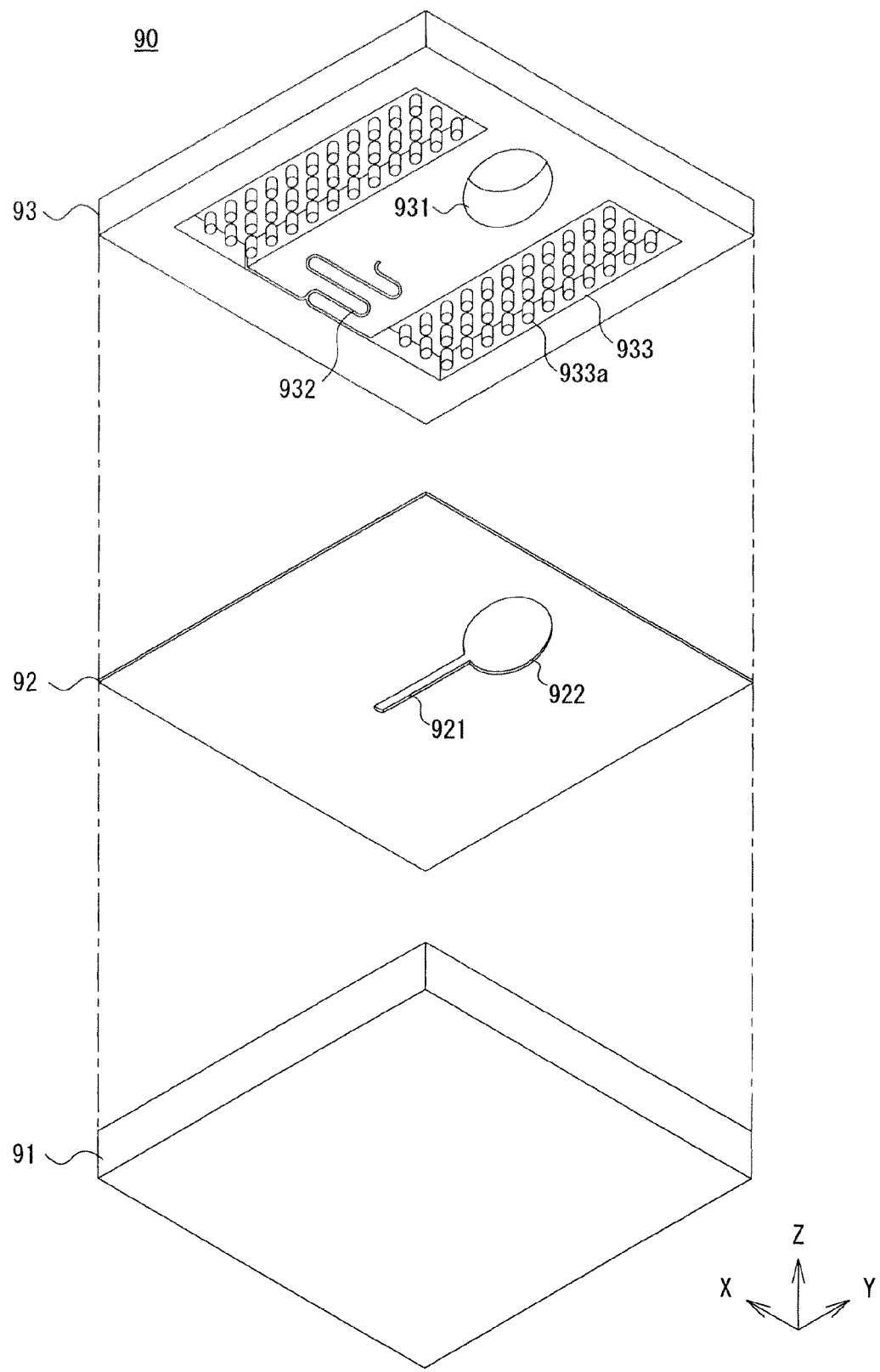
FIG. 26 is an exploded perspective view of the flow cell in FIG. 22 when viewed from the bottom.

As shown in FIG. 21, a flow cell 80 according to the sixth embodiment is formed from a first substrate 41, a first sheet-like member 42 which is disposed on the first substrate 41, a second substrate 43 which is disposed on the first sheet-like member 42, a second sheet-like member 44 which is disposed on the second substrate 43, a third substrate 51 which is disposed on the second sheet-like member 44, and a third sheet-like member 52 which is disposed on the third substrate 51. Similar to the flow cell 50 described in the fourth embodiment, the flow cell 80 configured by stacking the substrates and sheet-like members includes an inlet port 45 which passes through the first sheet-like member 42, second substrate 43, second sheet-like member 44, third substrate 51, and third sheet-like member 52 and allows introducing a sample solution, first suction pumps 48 which are formed between the first sheet-like member 42 and the second substrate 43, a second suction pump 49 which is formed between the second substrate 43 and the second sheet-like member 44, a third suction pump 53 which is formed between the second sheet-like member 44 and the third substrate 51, a fourth suction pump 54 which is formed between the third substrate 51 and the third sheet-like member 52, and a fluidic channel which connects the first suction pumps 48 and the inlet port 45. The fluidic channel is made up of a measurement fluidic channel 46 which has one end connected to the inlet port 45, is formed in the first sheet-like member 42, and irradiated with measurement light or the like by an external device, and a resistance fluidic channel 47 which has one end connected to the measurement fluidic channel 46 and the other end connected to the first suction pumps 48, and is formed between the first sheet-like member 42 and the second substrate 43.

<<Structure of Second Substrate>>

The second substrate 43 has a through hole 431 which is formed near the center on the one side, a meandering channel 432 which is formed from almost the center of the lower surface to the vicinity of the other side opposite to the one side, two first cavities 433 which are formed on the two sides of the meandering channel 432, and a second cavity 434 which is formed around the through hole 431 in the upper surface.

The two first cavities 433 are formed from the lower surface toward the upper surface of the second substrate 43 and have an almost rectangular shape when viewed from the top. A plurality of almost columnar projections 473a are formed in each cavity and project downward from its ceiling. The end of the projection 473a is formed to be located at a level vertically higher than the lower surface of the second substrate 43 when the second substrate 43 is placed on a horizontal surface. When the second substrate 43 is placed on the first sheet-like member 42, the projections 473a have open ends, i.e., do not contact the first sheet-like member 42, forming a space between them. At this time, the distance between the end of the projection 473a and the first sheet-like member 42 and the interval between the projections 473a are set to cause capillary action. The first cavities 433 function as the first suction pumps 48.

The second cavity 434 is formed from the upper surface toward the lower surface of the second substrate 43 and has an almost "U" shape when viewed from the top. A plurality of almost columnar projections 474a are formed in the cavity and project upward from its bottom. The end of the projection 474a is formed to be located at a level vertically lower than the upper surface of the second substrate 43 when the second substrate 43 is placed on a horizontal surface. When the second sheet-like member 44 is placed on the second substrate 43, the projections 474a have open ends, i.e., the ends of the projections 474a do not contact the second sheet-like member 44, forming a space between them. At this time, the distance between the end of the projection 474a and the second sheet-like member 44 and the interval between the projections 474a are set to cause capillary action. The second cavity 434 functions as the second suction pump 49.

<<Structure of Third Substrate>>

The third substrate 51 has a through hole 511 which is formed near the center on the one side, a third cavity 512 which is formed around the through hole 511 in the lower surface, and a fourth cavity 513 which is formed around the through hole 511 in the upper surface.

The third cavity 512 is formed from the lower surface toward the upper surface of the third substrate 51 and has an almost "U" shape when viewed from the top. A plurality of almost columnar projections 582a are formed in the cavity and project downward from its ceiling. The end of the projection 582a is formed to be located at a level vertically higher than the lower surface of the third substrate 51 when the third substrate 51 is placed on a horizontal surface. When the third substrate 51 is placed on the second sheet-like member 44, the projections 582a have open ends, i.e., do not contact the second sheet-like member 44, forming a space between them. At this time, the distance between the end of the projection 582a and the second sheet-like member 44 and the interval between the projections 582a are set to cause capillary action. The third cavity 512 functions as the third suction pump 53.

The fourth cavity 513 is formed from the upper surface toward the lower surface of the third substrate 51 and has an almost "U" shape when viewed from the top. A plurality of almost columnar projections 583a are formed in the cavity and project upward from its bottom. The end of the projection 583a is formed to be located at a level vertically lower than the upper surface of the third substrate 51 when the third substrate 51 is placed on a horizontal surface. When the third sheet-like member 52 is placed on the third substrate 51, the projections 583a have open ends, i.e., the ends of the projections 583a do not contact the third sheet-like member 52, forming a space between them. At this time, the distance between the end of the projection 583a and the third sheet-like member 52 and the interval between the projections 583a are set to cause capillary action. The fourth cavity 513 functions as the fourth suction pump 54.

With this structure, the flow cell 80 according to the sixth embodiment becomes larger in the internal capacity of each suction pump than the flow cell 50 described in the fourth embodiment, and the capacity of each suction pump can be increased. Since the ends of the projections, and portions of the sheet-like member that abut against these ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump may be clogged with the impurity in a conventional structure. However, since the ends of the projections do not contact the sheet-like member, a gap is formed between them, as described above. The impurity can pass through the gap, preventing clogging of the inside of the suction pump with the impurity.

<Application Example of Flow Cell>

A flow cell exemplified in each of the third to sixth embodiments is applied to measurement using the surface plasmon resonance phenomenon described with reference to FIG. 11.

Seventh Embodiment

The seventh embodiment according to the present invention will be described in detail.

In general, a desired flow rate profile changes depending on the type of sample solution or measurement apparatus, such as detection of an antigen-antibody reaction. However, in a technique using a conventional capillary pump, the flow rate of a sample solution once introduced from an inlet port cannot be changed during the process. The seventh embodiment aims to provide a flow cell capable of changing the flow rate of a liquid.

The flow cell according to the seventh embodiment is formed from a plate-like member having an opening, a fluidic channel having one end connected to the opening, and a pump which is connected to the other end of the fluidic channel and sucks, by the surface tension, a liquid that has reached the pump through the fluidic channel. The pump is formed from a cavity which is formed in the plate-like member, and a plurality of pillars which are formed in the cavity. The surface area per unit volume in the cavity changes depending on the position in the cavity.

In the flow cell, it is also possible to make pillars stand upright on the bottom of the cavity that is almost parallel to the plate-like member, form them on the bottom in a predetermined first direction, and form the first region uniformly deeply between the pillars in the first direction on the bottom. It is also possible to form pillars in the second direction perpendicular to the first direction on the bottom, and form the second region between the pillars on a bottom not common to that of the first region so as to be shallower than the first region.

In the flow cell, the pump may have a plurality of regions having pillars formed at predetermined intervals in the cavity. The predetermined intervals may be changed in each region.

In the flow cell, the pillar may have an open end.

According to the seventh embodiment, the flow rate of a liquid introduced from an inlet port can be changed during the process by changing the surface area per unit volume in the cavity.

<Structure of Flow Cell>

The structure of a flow cell 90 according to the seventh embodiment will be described in detail with reference to FIGS. 22 to 26.

As shown in FIGS. 22 to 26, the flow cell 90 according to the seventh embodiment is formed from a first substrate 91 which has an almost rectangular shape when viewed from the top, a sheet-like member 92 which is disposed on the first substrate 91, and a second substrate 93 which is disposed on the sheet-like member 92. The first substrate 91, sheet-like member 92, and second substrate 93 are stacked to form one plate-like member. The flow cell 90 includes an inlet port 94 which passes through the second substrate 93 and allows introducing a sample solution, two suction pumps 97 which are formed between the sheet-like member 92 and the second substrate 93, and a fluidic channel which connects the suction pumps 97 and the inlet port 94. The fluidic channel is made up of a measurement fluidic channel 95 which has one end connected to the inlet port 94 and is formed in the sheet-like member 92 interposed between the first substrate 91 and the second substrate 93, and a resistance fluidic channel 96 which has one end connected to the other end of the measurement fluidic channel 95 and is formed between the sheet-like member 92 and the second substrate 93.

<<First Substrate>>

The first substrate 91 is made of optical glass such as BK7, is about 1 mm in thickness, and is an almost rectangular plate about 16 mm on a side when viewed from the top. An Au layer 91a is selectively formed by vapor deposition, sputtering, plating, or the like on the upper surface of the first substrate 91, i.e., a surface of the first substrate 91 on which the sheet-like member 92 is placed. Note that the Au layer 91a may be formed only at a portion corresponding to the measurement fluidic channel 95 or formed on the entire surface.

<<Sheet-Like Member>>

The sheet-like member 92 is formed from, e.g., a well-known adhesive tape about 10 μm to 150 μm in thickness, and has a planar shape corresponding to the first substrate 91. The sheet-like member 92 has a slit 921 which is formed at almost the center and has an almost rectangular shape when viewed from the top, and an opening 922 which is connected to one end of the slit 921 and has an almost circular shape when viewed from the top. The slit 921 is formed so that its longitudinal direction becomes almost parallel to any one side of the sheet-like member 92.

Together with the upper surface (i.e., a surface in contact with the sheet-like member 92) of the first substrate 91 and the lower surface (i.e., a surface in contact with the sheet-like member 92) of the second substrate 93, the slit 921 forms the measurement fluidic channel 95 which is an almost rectangular parallelepiped space. A section of the measurement fluidic channel 95 that is perpendicular to the longitudinal direction has dimensions enough to cause capillary action with respect to an aqueous solution.

The sheet-like member 92 can be fabricated by, for example, processing an adhesive tape into a desired shape by a cutter, laser, or the like.

<<Structure of Second Substrate>>

The second substrate 93 is formed from, e.g., an acrylic substrate about 0.5 to 5 mm in thickness, and has a planar shape corresponding to the first substrate 91 and sheet-like member 92. A through hole 931 is formed near the center of the second substrate 93 on its one side. The lower surface of the second substrate 93 has a meandering channel 932 which is formed from almost the center to the vicinity of the other side opposite to the one side, and two cavities 933 which are formed on the two sides of the meandering channel 932.

The through hole 931 has the same planar shape as that of the opening 922.

The meandering channel 932 has a crank-like planar shape with a plurality of bent portions. The bent portion is smoothly bent into an almost arcuate shape, i.e., curved shape. The other end of the meandering channel 932 branches near the other side of the second substrate 93. The branches extend in opposite directions in the perpendicular direction and are connected to the adjacent cavities 933, respectively.

The cavities 933 are formed from the lower surface toward the upper surface of the second substrate 93. A plurality of almost columnar projections 933a are formed in each cavity and project downward from its ceiling. By setting the projections 933a to have an interval enough to cause capillary action, the cavity 933 functions as the suction pump. The cavity 933 is formed into an almost rectangular shape when viewed from the top. Vents 933d and 933e are formed at ends of the cavities 933 near the one side. Vents 933b and 933c are formed at corners of the cavities 933 near the other side that are opposite to corners connected to the branches of the other end of the meandering channel 932. The vents 933b to 933e pass through the second substrate 93.

The projections 933a are juxtaposed in the X and Y directions. In the cavity 933, a plurality of fluidic channels are formed in the X and Y directions in an almost matrix pattern when viewed from the lower surface of the second substrate 93. In the seventh embodiment, a fluidic channel in the X direction (to be referred to as an X fluidic channel) is formed uniformly deep in the second substrate 93, as shown in FIG. 27. In contrast, in a fluidic channel in the Y direction (to be referred to as a Y fluidic channel), deep and shallow portions alternate in the second substrate 93 for the X fluidic channels. More specifically, as shown in FIG. 28, the X fluidic channel indicated by the line X1-X1' is uniformly deep. In the Y fluidic channel indicated by the line Y1-Y1', portions common to the X fluidic channels are deep, and portions between the projections 933a are shallow. A section in a direction perpendicular to one in which the X fluidic channel extends has a semi-arcuate shape, as indicated by the line X2-X2' which crosses the projections 933a in the X direction. A section in a direction perpendicular to one in which the Y fluidic channel extends has a semi-arcuate shape, as indicated by the line Y2-Y2' which crosses the projections 933a in the Y direction.

Together with the opening 922 and the upper surface of the first substrate 91, the through hole 931 forms the inlet port 94 which is an almost columnar space with the upper surface of the first substrate defining its bottom.

When the second substrate 93 and sheet-like member 92 are brought into contact with each other, the meandering channel 932 forms the meandering resistance fluidic channel 96. The resistance fluidic channel 96 has sectional dimensions enough to cause capillary action with respect to an aqueous solution.

The second substrate 93 can be fabricated by injection molding using a mold having a predetermined pattern, laser processing, cutting using an end mill, or the like.

<Method of Manufacturing Flow Cell>

A method of manufacturing the flow cell 90 according to the seventh embodiment will be exemplified. First, the sheet-like member 92 is placed on the first substrate 91. When the Au layer 91a is formed only at part of the first substrate 91, the sheet-like member 92 is placed on the first substrate 91 so that the slit 921 for forming the measurement fluidic channel 95 is located on the Au layer 91a.

Then, the second substrate 93 is placed on the sheet-like member 92 so that the through hole 931 and opening 922 are connected to each other and one end of the meandering channel 932 is positioned in the other end of the slit 921.

After the first substrate 91, sheet-like member 92, and second substrate 93 are stacked in this way, they are pressed from the lower surface of the first substrate 91 and the upper surface of the second substrate 93. This fixes the first substrate 91 and second substrate 93 to each other via the sheet-like member 92 formed from a double-faced adhesive tape or the like, completing the flow cell 90 having the inlet port 94, measurement fluidic channel 95, resistance fluidic channel 96, and suction pumps 97.

<Operation of Flow Cell>

The operation of the flow cell 90 according to the seventh embodiment will be explained.

When a sample solution is injected from the inlet port 94, it proceeds sequentially through the measurement fluidic channel 95 and resistance fluidic channel 96 by capillary action, and flows into the suction pumps 97. In the suction pumps 97, a plurality of projections 933a are formed to increase the surface area per unit volume, compared to a structure in which no projection 933a is formed. The inside of the suction pump 97 has dimensions enough to cause capillary action. In the seventh embodiment, the projections 933a are set so that a surface tension larger than that in the measurement fluidic channel 95 and resistance fluidic channel 96 acts on a sample solution which has flowed into the suction pump 97.

The sample solution injected from the inlet port 94 passes through the measurement fluidic channel 95 and resistance fluidic channel 96, flows into the suction pumps 97, and proceeds through their insides. Note that the flow rate changes depending on the shape of the cavity 933 such as the outer shape and interval of the projection 933a, the resistance acting on the sample solution, and the like.

Figure 30A:
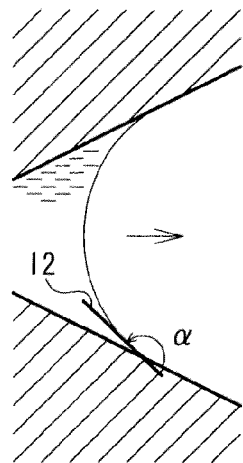
FIG. 30A is a view showing the state of a sample solution which flows through a tapered fluidic channel.
Figure 30B:
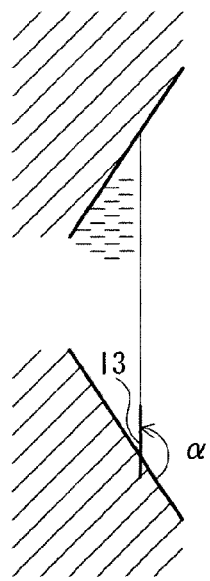
FIG. 30B is a view showing the state of a sample solution which flows through a fluidic channel that is tapered wider than that in FIG. 30A.

In the seventh embodiment, the X fluidic channel formed by a plurality of projections 933a in the suction pump 97 is formed uniformly deep in the substrate. In the Y fluidic channel, shallow portions, and deep portions which are common to the X fluidic channels alternate. For this reason, a sample solution in the X fluidic channel and that in the Y fluidic channel differ in flow rate because of a difference in the slope of the tangent of the liquid front at a portion where the sample solution, the wall surface of the fluidic channel, and air contact each other, i.e., at the edge of the liquid front of the sample solution. For example, when the tangent 11 of the liquid front of the sample solution is almost parallel to a direction in which the fluidic channel extends, and the liquid front is concaved with respect to the open end of the fluidic channel, as shown in FIG. 29, the sample solution proceeds toward the open end. When the open end of the fluidic channel is tapered as shown in FIG. 30A and the tangent 12 of the sample solution becomes slightly perpendicular to the direction in which the fluidic channel extends, compared to the case in FIG. 29, the surface tension decreases, and the flow rate of the sample solution becomes lower than that in FIG. 29. When the taper angle becomes larger than that in FIG. 30A and the tangent 13 of the liquid front of the sample solution becomes perpendicular to the direction in which the fluidic channel extends, as shown in FIG. 30B, the surface tension decreases or becomes nil, and the sample solution further decreases the flow rate or does not proceed any longer.

Figure 31:
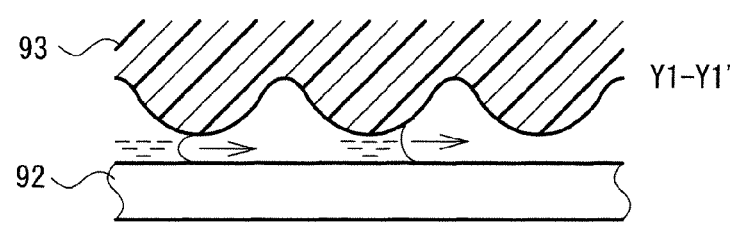
FIG. 31 is a view showing the state of a sample solution which flows through a Y fluidic channel.

In this way, the flow rate of a sample solution depends on the contact angle with respect to the wall surface of the fluidic channel. In the X fluidic channel which is formed uniformly deep, the sample solution proceeds at a constant rate. However, in the Y fluidic channel in which deep and shallow portions alternate, as shown in FIG. 31, the sample solution proceeds while changing the flow rate. Especially at a portion where the structure abruptly changes, the surface tension decreases or becomes nil, so the sample solution decreases the flow rate or does not proceed any longer. As a result, the sample solution which has flowed into the suction pump 97 preferentially flows through an X fluidic channel and only after filling the X fluidic channel by a predetermined amount, flows into a Y fluidic channel. That is, the sample solution proceeds through a Y fluidic channel only after proceeding through an X fluidic channel, and then proceeds through an X fluidic channel again.

Figure 32:
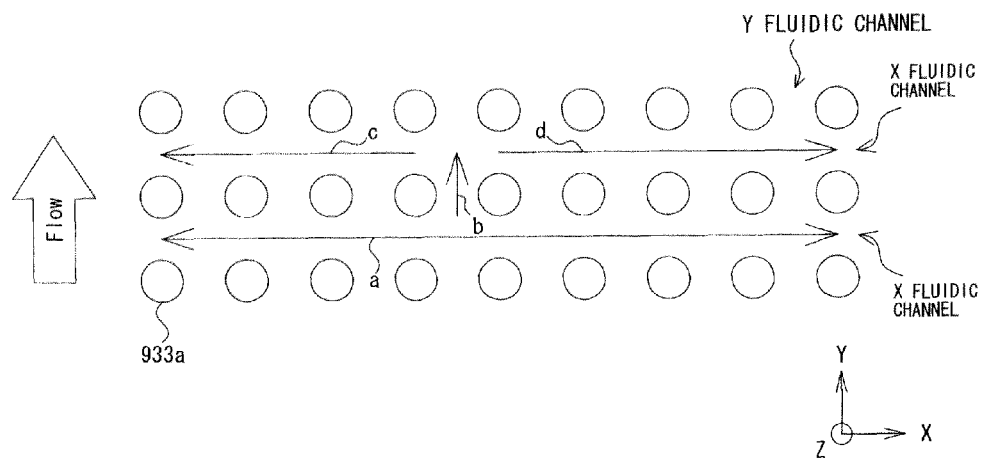
FIG. 32 is a view for explaining the operation of a suction pump in the seventh embodiment of the present invention.

For example, when the sample solution proceeds in the Y direction, as shown in FIG. 32, the sample solution which has flowed into an X fluidic channel proceeds in a direction in which the X fluidic channel extends (a). If the balance between the pressure component of the sample solution which fills the X fluidic channel and that which prevents the sample solution from flowing into any Y fluidic channel adjacent to the X fluidic channel is lost, the sample solution proceeds through the Y fluidic channel and flows into an adjacent X fluidic channel (b). The sample solution which has flowed into the X fluidic channel proceeds in directions in which the X fluidic channel extends (c and d), filling the X fluidic channel and the Y fluidic channel between this X fluidic channel and the X fluidic channel which has already been filled. By repeating this operation, the sample solution proceeds through the inside of the suction pump 97.

Figure 33:
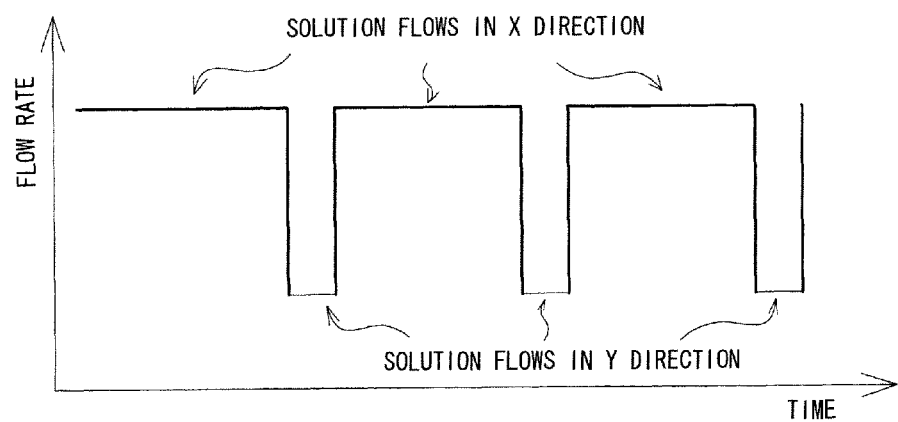
FIG. 33 is a chart exemplifying the flow rate of a sample solution in the seventh embodiment of the present invention.

In this fashion, the sample solution alternately proceeds through the X and Y fluidic channels, i.e., the X and Y directions. The sample solution flows smoothly in the X direction, but does not flow smoothly in the Y direction because it does not proceed in the Y direction until the balance is lost after filling the X fluidic channel. Thus, the flow rate of the sample solution in the Y direction becomes lower than that in the X direction. As shown in FIG. 33, the sample solution proceeds through the inside of the suction pump 97 while alternately repeating a fast flow in the X direction and a slow flow in the Y direction. Even a sample solution in the resistance fluidic channel 96, measurement fluidic channel 95, and inlet port 94 subsequent to one in the suction pump 97 flows with a profile as shown in FIG. 33.

The flow rates in the X and Y directions and the times during which the sample solution flows in these directions can be controlled by the interval between the projections 933a and the depths of the X and Y fluidic channels. By forming the suction pump 97 in accordance with a desired flow rate profile of the sample solution, the flow rate profile of the sample solution proceeding through the suction pump 97 can be controlled. Even the profile of the sample solution flowing through a stage preceding the suction pumps 97 can be controlled. The sample solution introduced from the inlet port 94 can be supplied through the measurement fluidic channel 95 with a desired flow rate profile corresponding to the types of sample solution and measurement apparatus.

For example, in the flow cell 90 according to the seventh embodiment, a suction pump 97 in which the interval between projections 933a was about 300 μm, the depth of the X fluidic channel was about 700 μm, and that of the Y fluidic channel was about 400 μm was fabricated, as shown in FIG. 27. In this case, it was confirmed that a sample solution flowed through an X fluidic channel and then flowed into an adjacent X fluidic channel via a Y fluidic channel.

In the seventh embodiment, sections of the X and Y fluidic channels formed in the cavity 933 in directions perpendicular to ones in which these fluidic channels extend have a semi-arcuate shape. However, the shapes of the sections are not limited to a semi-arcuate shape and can be freely set such as a sine wave shape.

In the seventh embodiment, the resistance fluidic channel 96 is arranged, but the measurement fluidic channel 95 and suction pumps 97 may be directly connected without arranging the resistance fluidic channel 96. Also, the shape of the resistance fluidic channel 96, i.e., that of the meandering channel 932 is not limited to the above-mentioned crank shape and can be freely set.

In the seventh embodiment, the ends of the projections 933*a* formed in the cavity 933 contact the sheet-like member 92, but they may be open ends, i.e., they need not contact the sheet-like member. The internal capacity of the suction pump 97 is increased by an amount by which the projections 933*a* are shortened, so the capacity of the suction pump 97 can be increased. Since the ends of the projections 933*a*, and portions of the sheet-like member 92 that abut against these ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 97 may be clogged with the impurity in a conventional structure. However, since the ends of the projections 933*a* do not contact the sheet-like member 92, a gap is formed between them, as described above. The impurity can pass through the gap, preventing clogging of the inside of the suction pump 97 with the impurity.

In the seventh embodiment, the slit 921 has an almost rectangular shape when viewed from the top, and is formed at almost the center of the sheet-like member 92. However, the shape and formation position of the slit 921 are not limited to them and can be freely set as long as the slit 921 extends on the Au layer 91*a*. Even the shape and position of the measurement fluidic channel 95 defined by the slit 921 can be freely set.

In the seventh embodiment, the opening 922 has an almost circular shape when viewed from the top. However, the shape of the opening 922 is not limited to this, and can be freely set as long as the opening 922 exists at a position where it is connected to the through hole 931 of the second substrate 93.

In the seventh embodiment, the cavity 933 has an almost rectangular shape when viewed from the top. However, the planar shape of the cavity 933 is not limited to this and can be freely set. Similarly, the shape of the projection 933*a* formed in the cavity 933 is not limited to an almost columnar shape and can be freely set as long as the surface area in the cavity 933 increases.

Eighth Embodiment

The eighth embodiment according to the present invention will be described. In the eighth embodiment, the structure of the cavity 933 which forms the suction pump 97 in the seventh embodiment is changed. Hence, the same reference numerals as those in the seventh embodiment denote the same parts except for the suction pump, and a description thereof will be properly omitted.

Figure 34:
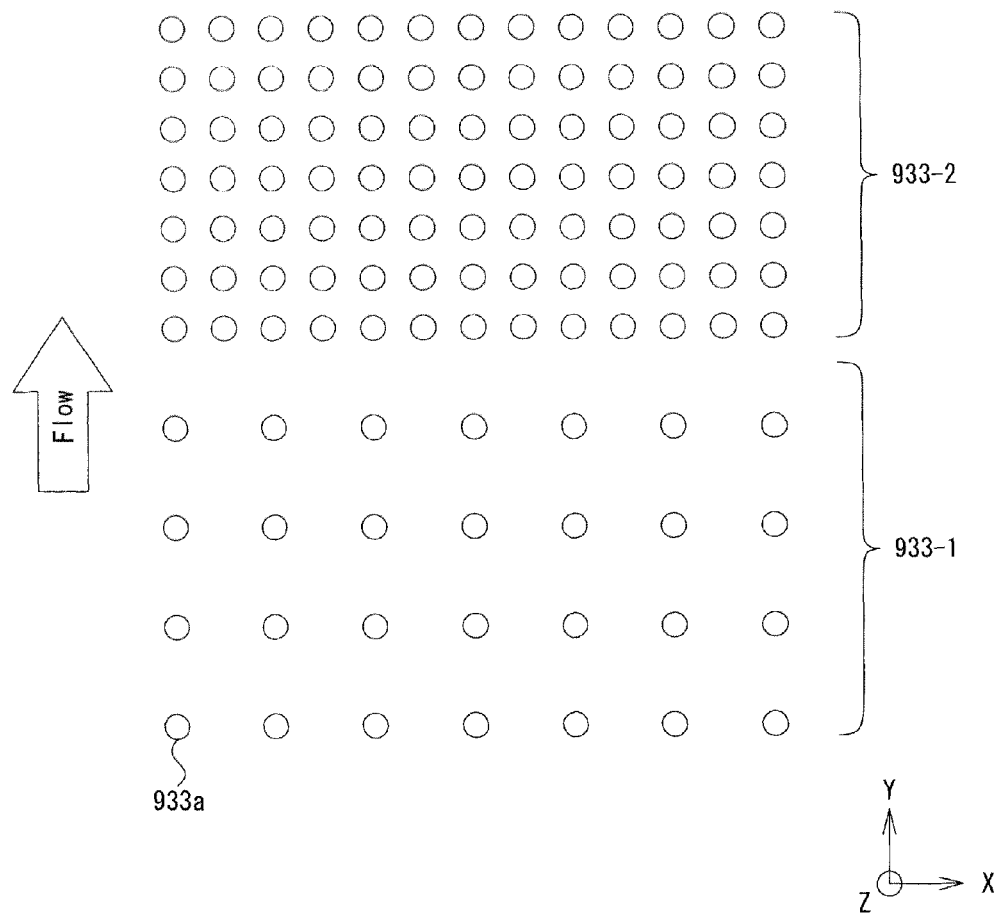
FIG. 34 is a view exemplifying the arrangement of projections in the eighth embodiment of the present invention.

In the eighth embodiment, cavities 933 are formed from the lower surface toward the upper surface of a second substrate 93. A plurality of almost columnar projections 933*a* are formed in each cavity and project downward from its ceiling. The projections 933*a* are regularly juxtaposed at predetermined intervals in the X and Y directions. The interval is set large in a first region 933-1 of the cavity 933 near the other side, and small in a second region 933-2 near one side, as shown in FIG. 34.

Figure 35:
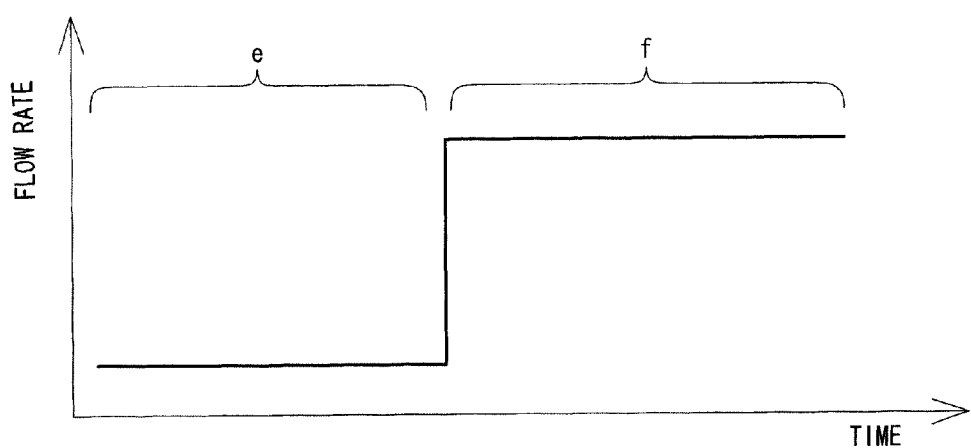
FIG. 35 is a chart exemplifying the flow rate of a sample solution in the eighth embodiment of the present invention.

The flow rate of a sample solution which proceeds through the cavity 933 depends on the internal shape of the cavity 933. As the surface area per unit volume is larger, i.e., the area of contact with the sample solution is larger, the flow rate becomes higher. Since the surface area per unit volume is larger in the second region 933-2 where the interval between the projections 933*a* is smaller than in the first region 933-1 where it is larger, the flow rate of the sample solution becomes higher, as shown in FIGS. 34 and 35. By controlling the interval between the projections 933*a* in the cavity 933 in accordance with a desired flow rate profile of the sample solution, the flow rate profile of a sample solution which proceeds through a suction pump 97 can be controlled. Even the flow rate profile of the sample solution flowing through a stage preceding the suction pumps 97 can be controlled. The sample solution can be supplied into a measurement fluidic channel 95 with a desired flow rate profile of the sample solution that corresponds to the types of sample solution and measurement apparatus.

In the eighth embodiment, the cavity 933 has two regions, i.e., the first region 933-1 and second region 933-2. Needless to say, the cavity 933 may be divided into an appropriate number of regions such as three or four. When the cavity 933 is divided into many regions, the interval between the projections 933*a* may be changed for each region or regions having the same interval may exist.

In the eighth embodiment, a resistance fluidic channel 96 is arranged, but the measurement fluidic channel 95 and suction pumps 97 may be directly connected without arranging the resistance fluidic channel 96. Also, the shape of the resistance fluidic channel 96, i.e., that of a meandering channel 932 is not limited to the above-mentioned crank shape and can be freely set.

In the eighth embodiment, the ends of the projections 933*a* formed in the cavity 933 contact a sheet-like member 92, but they may be open ends, i.e., they need not contact the sheet-like member. The internal capacity of the suction pump 97 is increased by an amount by which the projections 933*a* are shortened, so the capacity of the suction pump 97 can be increased. Since the ends of the projections 933*a*, and portions of the sheet-like member 92 that abut against these ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 97 may be clogged with the impurity in a conventional structure. However, since the ends of the projections 933*a* do not contact the sheet-like member 92, a gap is formed between them, as described above. The impurity can pass through the gap, preventing clogging of the inside of the suction pump 97 with the impurity.

In the eighth embodiment, a slit 921 has an almost rectangular shape when viewed from the top, and is formed at almost the center of the sheet-like member 92. However, the shape and formation position of the slit 921 are not limited to them and can be freely set as long as the slit 921 extends on an Au layer 91a. Even the shape and position of the measurement fluidic channel 95 defined by the slit 921 can be freely set.

In the eighth embodiment, an opening 922 has an almost circular shape when viewed from the top. However, the shape of the opening 922 is not limited to this and can be freely set as long as the opening 922 exists at a position where it is connected to a through hole 931 of the second substrate 93.

In the eighth embodiment, the cavity 933 has an almost rectangular shape when viewed from the top. However, the planar shape of the cavity 933 is not limited to this and can be freely set. Similarly, the shape of the projection 933a formed in the cavity 933 is not limited to an almost columnar shape and can be freely set as long as the surface area in the cavity 933 increases.

In the eighth embodiment, the sheet-like member 92 is arranged, but the flow cell may be formed from a first substrate 91 and the second substrate 93 without arranging the sheet-like member 92. In this case, the slit formed in the sheet-like member 92 is formed in the first substrate 91 or second substrate 93. A member to engage with the sides of the first substrate 91 and second substrate 93 is attached to join them. Alternatively, the first substrate 91 and second substrate 93 are bonded to each other using an adhesive or the like.

<Application Example of Flow Cell>

A flow cell exemplified in each of the seventh and eighth embodiments is applied to measurement using the surface plasmon resonance phenomenon described with reference to FIG. 11.

Ninth Embodiment

In a conventional capillary pump, pillars are formed at constant intervals. The direction of progression of a sample solution in the capillary pump has not been examined sufficiently. For example, air may remain in the capillary pump. In this case, the capacity of the capillary pump cannot be fully utilized. A predetermined amount of sample solution cannot pass through the measurement fluidic channel, failing to normally measure the sample solution.

From this, the ninth embodiment aims to provide a flow cell in which a sample solution can proceed in a desired direction in the capillary pump.

To solve the above problems, the flow cell according to the ninth embodiment is formed from a plate-like member having an opening, a fluidic channel having one end connected to the opening, and a pump which is connected to the other end of the fluidic channel and sucks, by the surface tension, a liquid that has reached the pump through the fluidic channel. The pump is formed from a cavity which is formed in the plate-like member, and a plurality of pillars which are periodically formed in the cavity. The interval between adjacent pillars is smaller in a predetermined direction than that in another direction. The pillar may have an open end.

According to the ninth embodiment, the pillars arranged in the cavity which forms the suction pump are formed such that the interval between adjacent pillars becomes smaller in a predetermined direction than that in another direction. With this structure, a liquid can proceed in a predetermined direction.

<Structure of Flow Cell>

Details of a flow cell 100 according to the ninth embodiment will be described with reference to FIGS. 36 to 40.

As shown in FIGS. 36 to 40, the flow cell 100 according to the ninth embodiment is formed from a first substrate 101 which has an almost rectangular shape when viewed from the top, a sheet-like member 102 which is disposed on the first substrate 101, and a second substrate 103 which is disposed on the sheet-like member 102. The first substrate 101, sheet-like member 102, and second substrate 103 are stacked to form one plate-like member. The flow cell 100 includes an inlet port 104 which passes through the sheet-like member 102 and second substrate 103 and allows introducing a sample solution, two suction pumps 107 which are formed between the sheet-like member 102 and the second substrate 103, and a fluidic channel which connects the suction pumps 107 and the inlet port 104. The fluidic channel is made up of a measurement fluidic channel 105 which has one end connected to the inlet port 104 and is formed in the sheet-like member 102 interposed between the first substrate 101 and the second substrate 103, and a resistance fluidic channel 106 which has one end connected to the other end of the measurement fluidic channel 105 and is formed between the sheet-like member 102 and the second substrate 103.

<<First Substrate>>

The first substrate 101 is made of optical glass such as BK7, is about 1 mm in thickness, and has an almost rectangular shape about 16 mm on a side when viewed from the top. An Au layer 101a is formed by vapor deposition, sputtering, plating, or the like on the upper surface of the first substrate 101, i.e., a surface of the first substrate 101 on the side of the sheet-like member 102. Note that the Au layer 101a may be formed only at a portion corresponding to the measurement fluidic channel 105.

<<Sheet-Like Member>>

The sheet-like member 102 is formed from, e.g., a well-known adhesive tape about 10 μm to 150 μm in thickness, and has a planar shape corresponding to the first substrate 101. The sheet-like member 102 has a slit 1021 which is formed at almost the center and has an almost rectangular shape when viewed from the top, and an opening 1022 which is connected to one end of the slit 1021 and has an almost circular shape when viewed from the top. The slit 1021 is formed so that its longitudinal direction becomes almost parallel to any one side of the sheet-like member 102.

Together with the upper surface of the first substrate 101 and the lower surface of the second substrate 103, the slit 1021 forms the measurement fluidic channel 105 which is an almost rectangular parallelepiped space. A section of the measurement fluidic channel 105 that is perpendicular to the longitudinal direction has dimensions enough to cause capillary action with respect to an aqueous solution.

The sheet-like member 102 can be fabricated by, for example, processing an adhesive tape into a desired shape by a cutter, laser, or the like.

<<Structure of Second Substrate>>

The second substrate 103 is formed from, e.g., an acrylic substrate about 0.5 to 5 mm in thickness, and has a planar shape corresponding to the first substrate 101 and sheet-like member 102. A through hole 1031 is formed near the center of the second substrate 103 on its one side. The lower surface of the second substrate 103 has a meandering channel 1032 which is formed from almost the center to the vicinity of the other side opposite to the one side, and two cavities 1033 which are formed on the two sides of the meandering channel 1032.

The through hole 1031 has the same planar shape as that of the opening 1022.

The meandering channel 1032 has a crank-like planar shape with a plurality of bent portions. The bent portion is smoothly bent into an almost arcuate shape, i.e., curved shape. The other end of the meandering channel 1032 branches near the other side of the second substrate 103. The branches extend in opposite directions in the perpendicular direction and are connected to the adjacent cavities 1033, respectively.

The two cavities 1033 are formed from the lower surface toward the upper surface of the second substrate 103, and have an almost rectangular shape when viewed from the top. A plurality of almost columnar projections 1033*a* are formed in each cavity and project downward from its ceiling. By setting the projections 1033*a* to have an interval enough to cause capillary action, the cavity 1033 functions as the suction pump. The cavity 1033 is formed into an almost rectangular shape when viewed from the top. Vents 1033*d* and 1033*e* are formed at ends of the cavities 1033 near the one side. Vents 1033*b* and 1033*c* are formed at corners of the cavities 1033 near the other side that are opposite to corners connected to the branches of the other end of the meandering channel 1032. The vents 1033*b* to 1033*e* pass through the second substrate 103.

Figure 41:
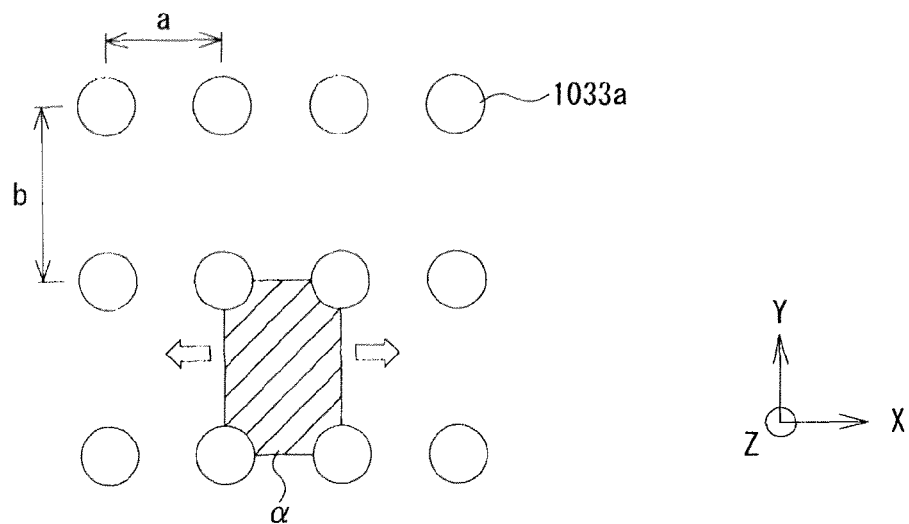
FIG. 41 is a view exemplifying the arrangement of projections in a suction pump.

The projections 1033*a* are regularly juxtaposed in the X and Y directions at predetermined intervals. In the ninth embodiment, the projections 1033*a* are arrayed to have a distance a in the X direction and a distance b (>a) in the Y direction between themselves, as shown in FIG. 41.

Together with the opening 1022 and the upper surface of the first substrate 101, the through hole 1031 forms the inlet port 104 which is an almost columnar space with the upper surface of the first substrate defining its bottom.

When the second substrate 103 and sheet-like member 102 are brought into contact with each other, the meandering channel 1032 forms the meandering resistance fluidic channel 106. The resistance fluidic channel 106 has sectional dimensions enough to cause capillary action with respect to an aqueous solution.

The second substrate 103 can be fabricated by injection molding using a mold having a predetermined pattern, laser processing, cutting using an end mill, or the like.

<Method of Manufacturing Flow Cell>

A method of manufacturing the flow cell 100 according to the ninth embodiment will be exemplified. First, the sheet-like member 102 is placed on the first substrate 101. When the Au layer 101*a* is formed only at part of the first substrate 101, the sheet-like member 102 is placed on the first substrate 101 so that the slit 1021 for forming the measurement fluidic channel 105 is located on the Au layer 101*a*.

Then, the second substrate 103 is placed on the sheet-like member 102 so that the through hole 1031 and opening 1022 are connected to each other and one end of the meandering channel 1032 is positioned in the other end of the slit 1021.

After the first substrate 101, sheet-like member 102, and second substrate 103 are stacked in this way, they are pressed from the lower surface of the first substrate 101 and the upper surface of the second substrate 103. This fixes the first substrate 101 and second substrate 103 to each other via the sheet-like member 102 formed from a double-faced adhesive tape or the like, completing the flow cell 100 having the inlet port 104, measurement fluidic channel 105, resistance fluidic channel 106, and suction pumps 107.

<Operation of Flow Cell>

The operation of the flow cell 100 according to the ninth embodiment will be explained.

When a sample solution is injected from the inlet port 104, it proceeds sequentially through the measurement fluidic channel 105 and resistance fluidic channel 106 by capillary action, and flows into the suction pumps 107. In the suction pumps 107, a plurality of projections 1033*a* are formed to increase the surface area per unit volume, compared to a structure in which no projection 1033*a* is formed. The inside of the suction pump 107 has dimensions enough to cause capillary action. In the ninth embodiment, the shape and interval of the projections 1033*a* and the like are set so that the surface tension which acts on the liquid front of the sample solution in the suction pump 107 becomes larger than that which acts on the liquid front of the sample solution in the inlet port 104.

The sample solution injected from the inlet port 104 passes through the measurement fluidic channel 105 and resistance fluidic channel 106, flows into the suction pumps 107, and proceeds through their insides. Note that the flow rate changes depending on the shape of the cavity 1033 such as the outer shape and interval of the projection 1033*a*, the resistance acting on the sample solution, and the like.

Figure 42:
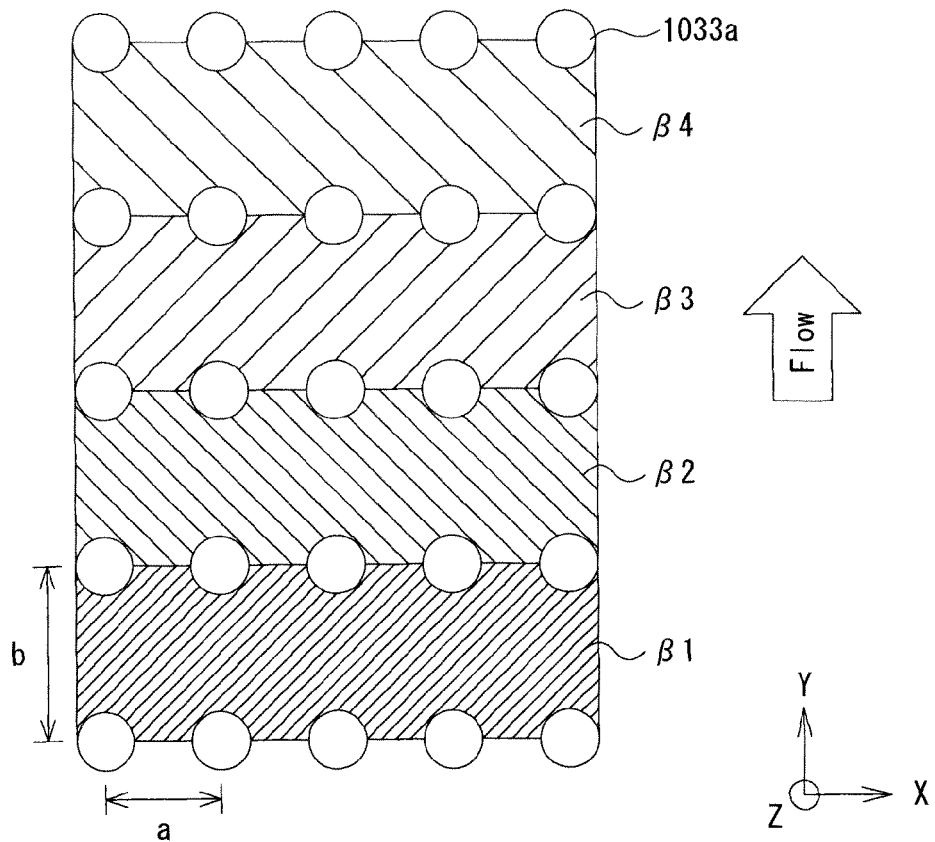
FIG. 42 is a view for explaining the internal operation of the suction pump.

The sample solution which has flowed into the suction pumps 107 proceeds through their insides. The direction of progression depends on the surface tension acting on the sample solution, the interval between the projections 1033*a*, and the like. For example, assume that the projections 1033*a* are spaced apart by the distance a in the X direction and the distance b (>a) in the Y direction, and a liquid proceeds similarly in the X and Y directions from a region α which is surrounded by the projections 1033*a* at four corners and has an almost rectangular shape when viewed from the top. When the liquid proceeds by the distance a in both the X and Y directions, the liquid which has proceeded in the X direction reaches a projection 1033*a* adjacent (X direction) to the region α. However, the liquid which has proceeded in the Y direction does not reach a projection 1033*a* adjacent (Y direction) to the region α. The liquid which has proceeded in the X direction and reached the adjacent projection 1033*a* draws, in the X direction, even the liquid which has proceeded in the Y direction, owing to the surface tension generated by the projection 1033*a*. By repeating this operation, the liquid which has flowed into the suction pump 107 proceeds in the X direction. When the sample solution proceeds in the X direction and fills a region (to be referred to as an X channel) between one group of projections 1033*a* juxtaposed in the X direction and another adjacent group of projections 1033*a*, it proceeds in the Y direction to fill an adjacent X channel. As shown in FIG. 42, the sample solution proceeds in the Y direction while filling X channels β1 to β4 juxtaposed in the Y direction one by one in the order named.

By properly setting the intervals between the projections 1033*a* in the X and Y directions, the direction of progression of a sample solution in the suction pump 107 can be controlled. The projections 1033*a* are arranged in accordance with the structure of the flow cell, preventing air from remaining in the flow cell. The capacity of the capillary pump can be fully used. Hence, a predetermined amount of sample solution can pass through the measurement fluidic channel to normally measure the sample solution.

Figure 36:
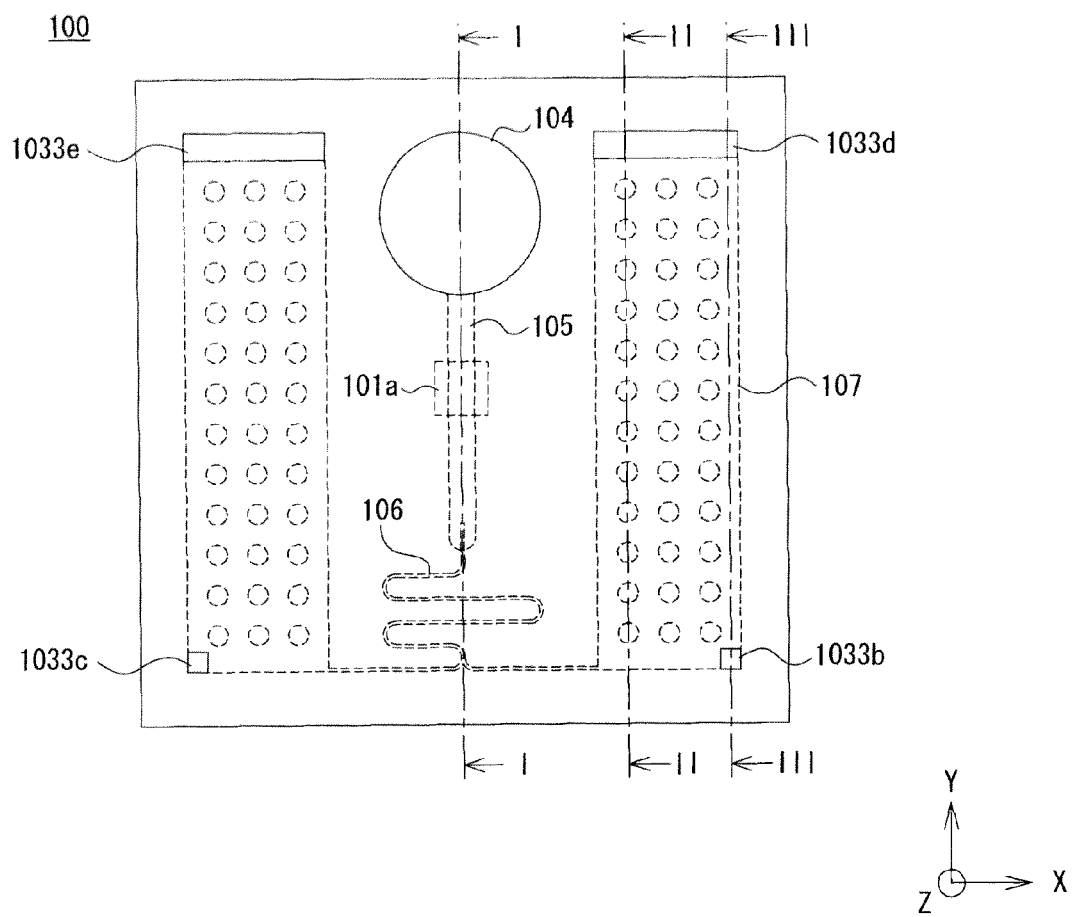
FIG. 36 is a plan view exemplifying the structure of a flow cell according to the ninth embodiment of the present invention.
Figure 37:
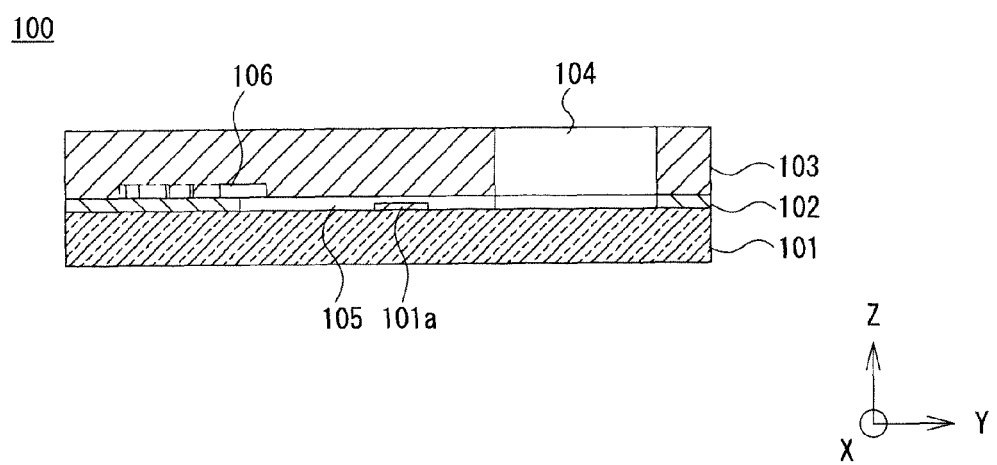
FIG. 37 is a sectional view taken along the line I-I in FIG. 36.
Figure 38:
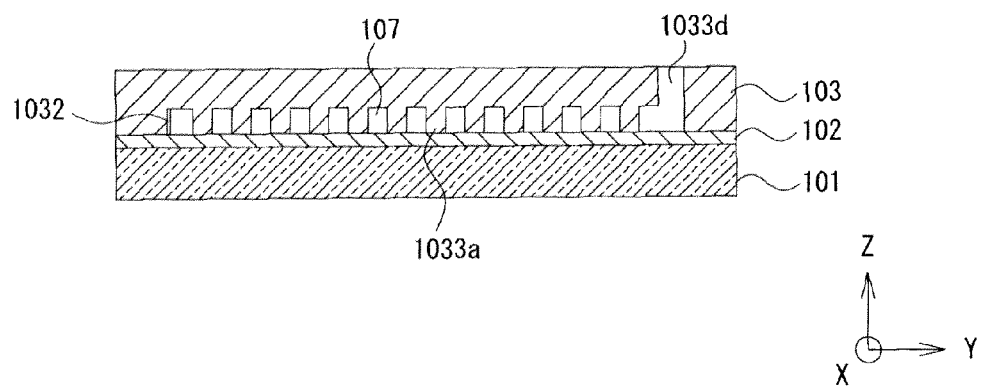
FIG. 38 is a sectional view taken along the line II-II in FIG. 36.
Figure 39:
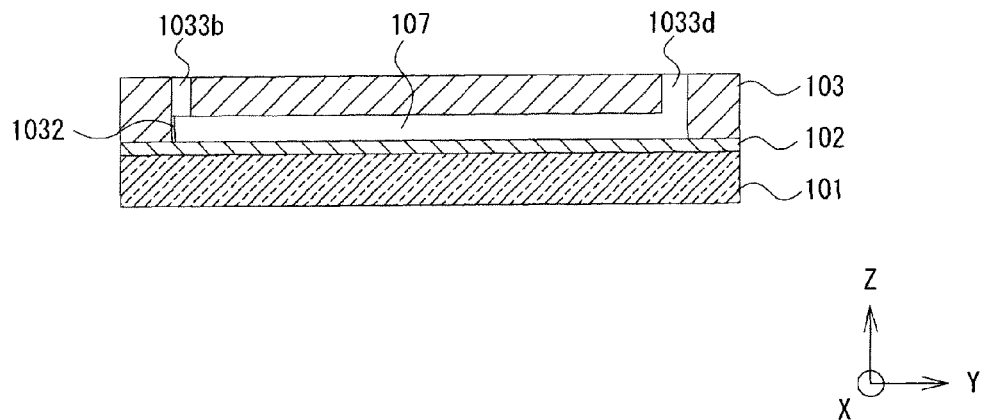
FIG. 39 is a sectional view taken along the line III-III in FIG. 36.
Figure 40:
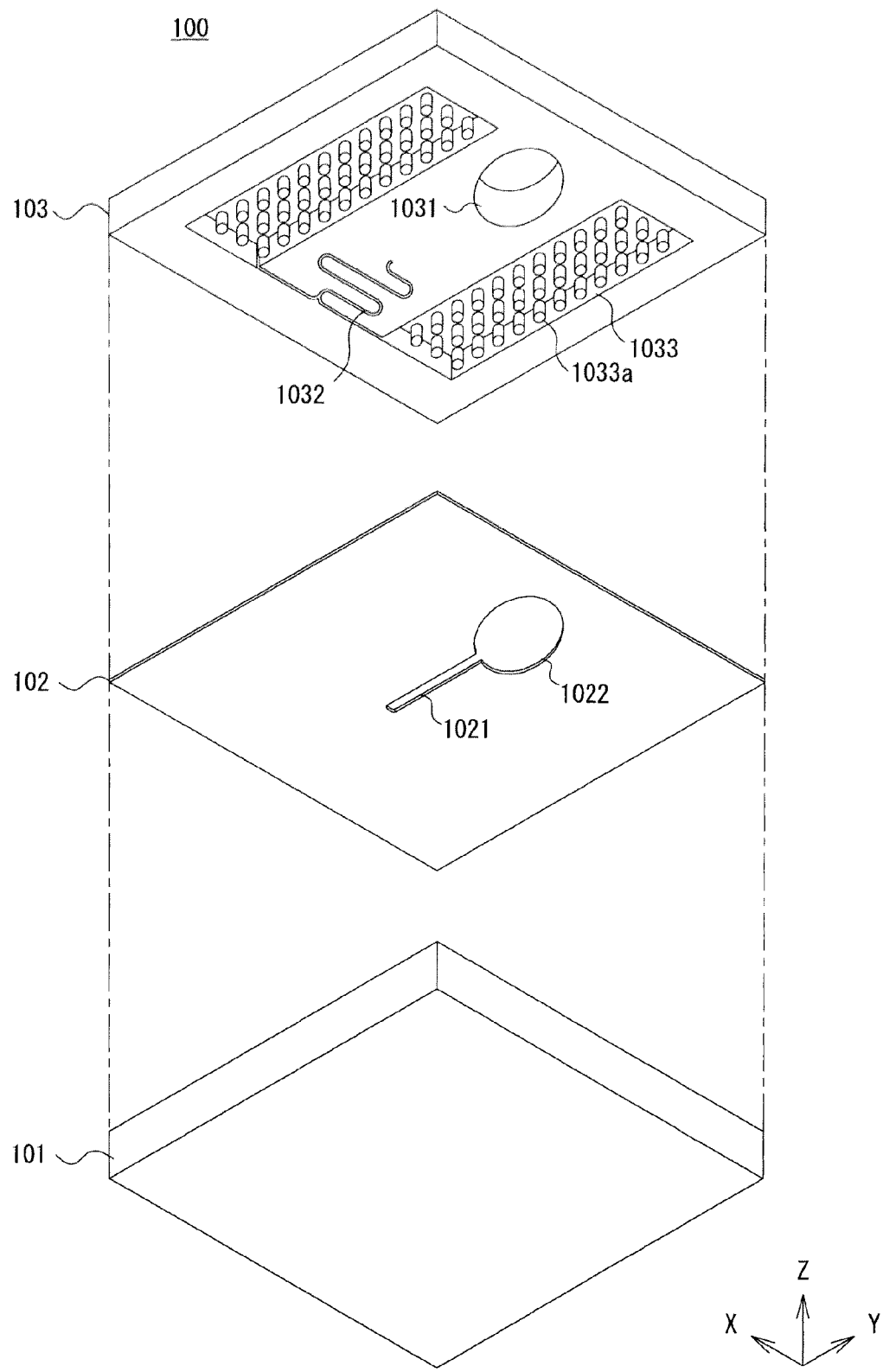
FIG. 40 is an exploded perspective view of the flow cell in FIG. 36 when viewed from the bottom.

For example, in the flow cell 100 shown in FIG. 36, the vents 1033*b* to 1033*e* are formed at ends of the cavities 1033 in the positive direction in the Y direction, and at corners opposite to those connected to the other end of the meandering channel 1032 in the negative direction in the Y direction. To prevent air from remaining in the cavity 1033, it suffices to, for example, form the projections 1033*a* in the X and Y directions to have an interval larger in the Y direction than that in the X direction. Then, a sample solution which has flowed into the suction pump 107 through the resistance fluidic channel 106 flows first in the X direction. Air which is present in and near the resistance fluidic channel 106 is exhausted from the vents 1033b and 1033c. Then, the sample solution proceeds in the Y direction while filling channels in the X direction. Air present in the suction pump 107 is pushed away by the sample solution in the Y direction, and finally exhausted from the vents 1033d and 1033e. By forming the projections 1033a in this manner, air can be prevented from remaining in the suction pump 107.

Figure 43:
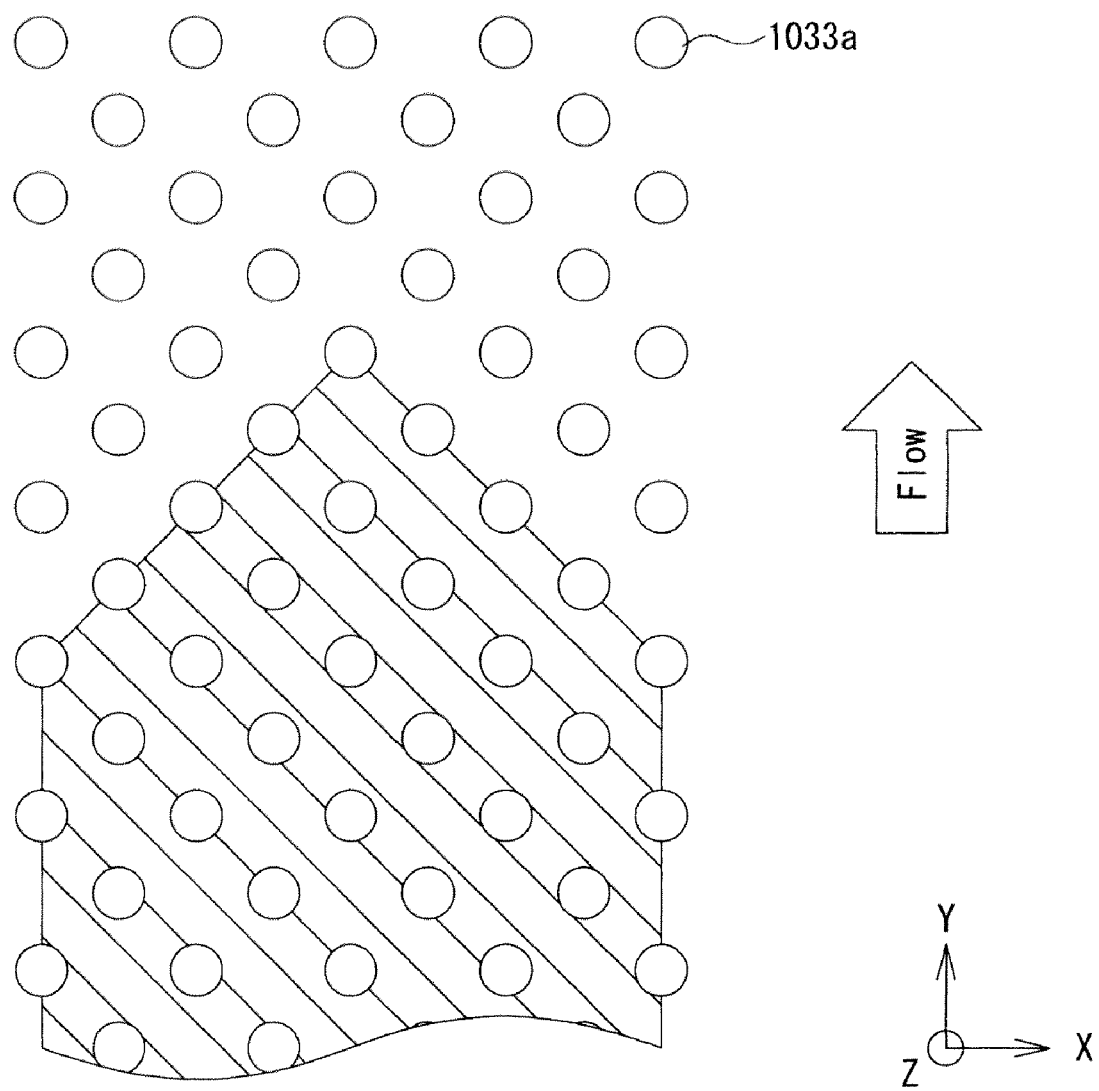
FIG. 43 is a view exemplifying another arrangement of projections in the suction pump.
Figure 44:
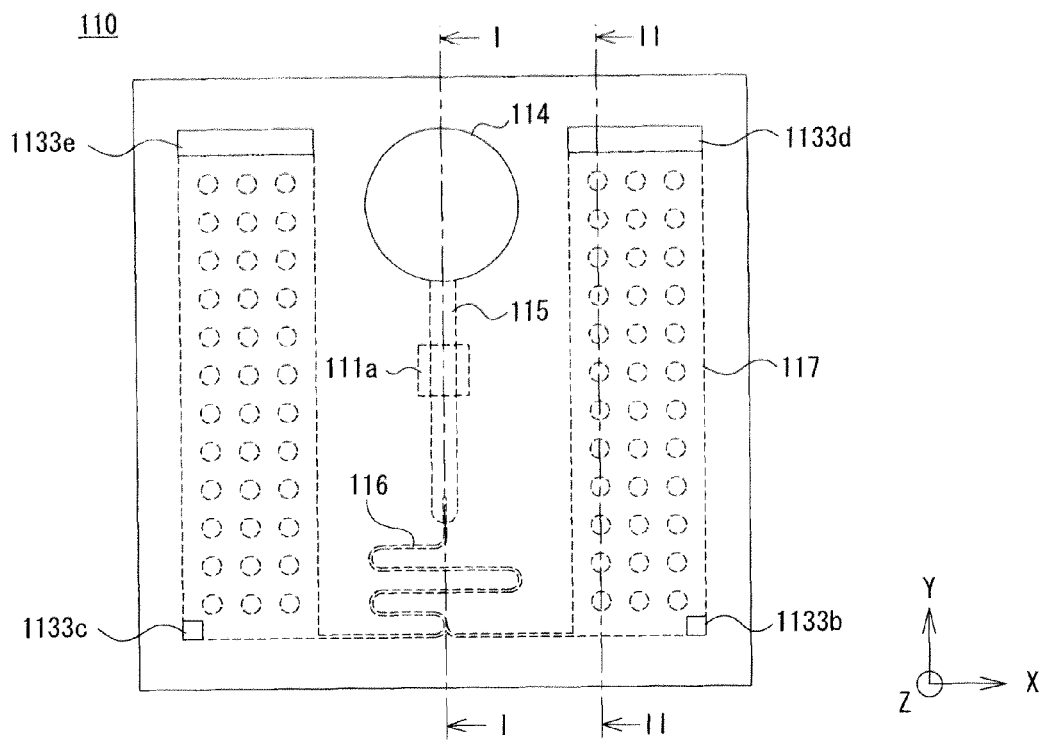
FIG. 44 is a plan view exemplifying the structure of a flow cell according to the 10th embodiment of the present invention.
Figure 45:
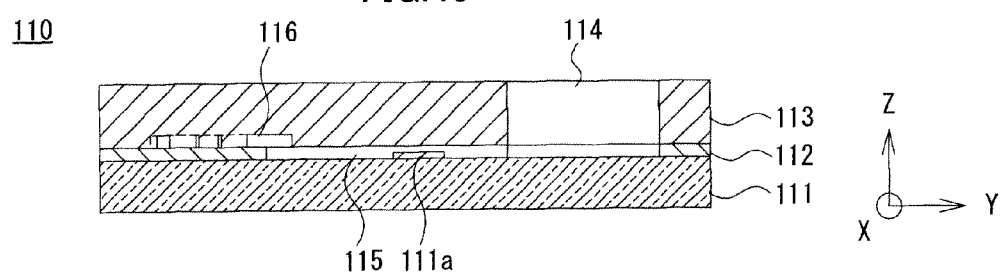
FIG. 45 is a sectional view taken along the line I-I in FIG. 44.
Figure 46:
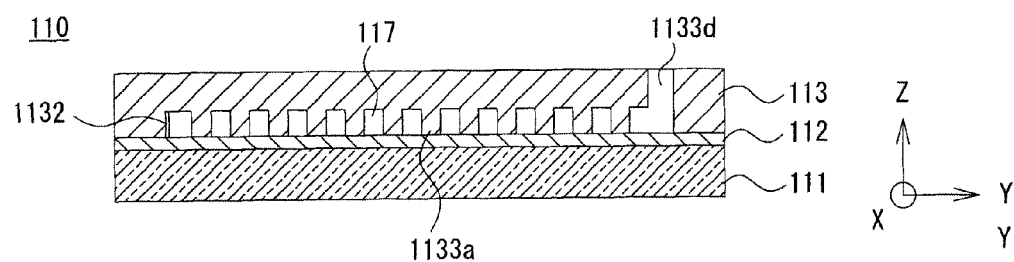
FIG. 46 is a sectional view taken along the line II-II in FIG. 44.
Figure 47:
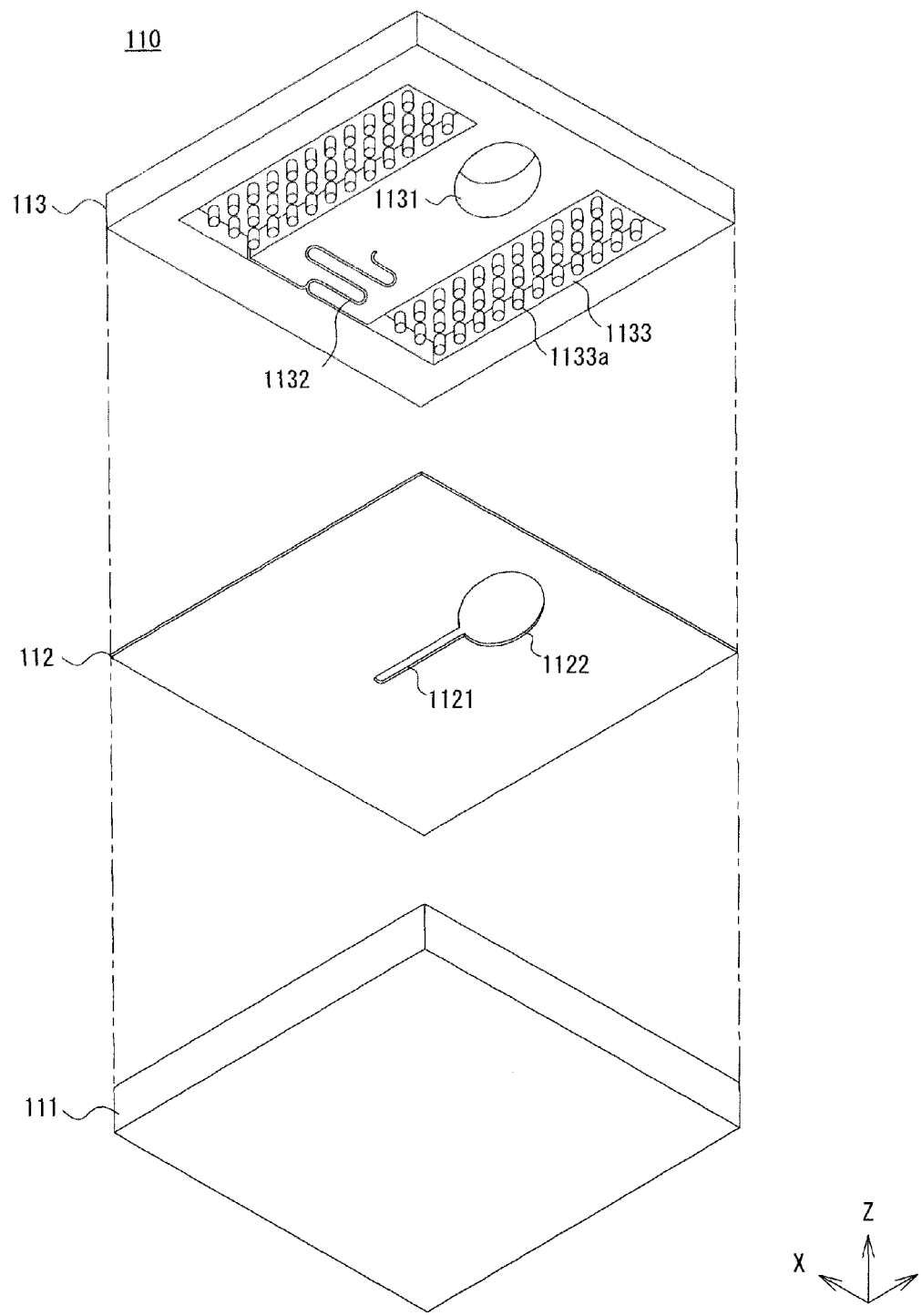
FIG. 47 is an exploded perspective view of the flow cell in FIG. 44 when viewed from the bottom.

For example, the projections 1033a may be formed as shown in FIG. 43. In FIG. 43, the projections 1033a are formed in the first direction which crosses the positive direction in the X direction at 45°, and the second direction which crosses the positive direction in the Y direction at 45° (positive direction in the X direction at 135°) so that the intervals between projections 1033a adjacent in the first and second directions become equal to each other. Even in this case, a sample solution proceeds in a direction in which the surface area is large, i.e., the interval between the projections 1033a is small. When the sample solution enters the suction pump 107 from the negative side in the Y direction, it proceeds in a direction in which the interval between the projections 1033a is small, that is, not toward projections 1033a adjacent in the Y direction but toward projections 1033a adjacent in directions inclined by 45° with respect to the positive and negative directions in the Y direction. As shown in FIG. 43, the sample solution proceeds through the inside of the suction pump 107 in the Y direction in an almost triangular shape which protrudes in the Y direction.

As an actual sample, a flow cell 100 having a suction pump 107 in which the diameter of a projection 1033a was about 200 μm, the intervals between projections 1033a in directions inclined by 45° with respect to the positive and negative directions in the Y direction were about 200 μm in the pattern shown in FIG. 43 was fabricated. In this case, it was confirmed that a sample solution proceeded through the inside of the suction pump 107 in the Y direction while drawing an almost triangular shape which protruded in the Y direction, as shown in FIG. 43.

In the ninth embodiment, the ends of the projections 1033a formed in the cavity 1033 contact the sheet-like member 102, but they may be open ends, i.e., they need not contact the sheet-like member. The internal capacity of the suction pump 107 is increased by an amount by which the projections 1033a are shortened, so the capacity of the suction pump 107 can be increased. Since the ends of the projections 1033a, and portions of the sheet-like member 102 that abut against these ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 107 may be clogged with the impurity in a conventional structure. However, since the ends of the projections 1033a do not contact the sheet-like member 102, a gap is formed between them, as described above. The impurity can pass through the gap, preventing clogging of the inside of the suction pump 107 with the impurity.

In the ninth embodiment, the slit 1021 has an almost rectangular shape when viewed from the top, and is formed at almost the center of the sheet-like member 102. However, the shape and formation position of the slit 1021 are not limited to them and can be freely set as long as the slit 1021 extends on the Au layer 101a. Even the shape and position of the measurement fluidic channel 105 defined by the slit 1021 can be freely set.

In the ninth embodiment, the opening 1022 has an almost circular shape when viewed from the top. However, the shape of the opening 1022 is not limited to this and can be freely set as long as the opening 1022 exists at a position where it is connected to the through hole 1031 of the second substrate 103.

In the ninth embodiment, the cavity 1033 has an almost rectangular shape when viewed from the top. However, the planar shape of the cavity 1033 is not limited to this and can be freely set. Similarly, the shape of the projection 1033a formed in the cavity 1033 is not limited to an almost columnar shape and can be freely set as long as the surface area in the cavity 1033 increases.

In the ninth embodiment, the resistance fluidic channel 106 is arranged, but the measurement fluidic channel 105 and suction pumps 107 may be directly connected without arranging the resistance fluidic channel 106. Also, the shape of the resistance fluidic channel 106, i.e., that of the meandering channel 1032 is not limited to the above-mentioned crank shape and can be freely set.

In the ninth embodiment, the sheet-like member 102 is arranged, but the flow cell may be formed from the first substrate 101 and second substrate 103 without arranging the sheet-like member 102. In this case, the slit formed in the sheet-like member 102 is formed in the first substrate 101 or second substrate 103. A member to engage with the sides of the first substrate 101 and second substrate 103 is attached to join them. Alternatively, the first substrate 101 and second substrate 103 are bonded to each other using an adhesive or the like.

<Application Example of Flow Cell>

A flow cell exemplified in the ninth embodiment is applied to measurement using the surface plasmon resonance phenomenon described with reference to FIG. 11.

10th Embodiment

The 10th embodiment according to the present invention will be described.

An application example of a measurement chip having a capillary pump will be described briefly. A measurement chip such as a flow cell having a capillary pump is applied to, for example, measurement using a well-known surface plasmon resonance phenomenon (see references 5 and 6). Measurement using the surface plasmon resonance phenomenon utilizes resonance of an evanescent wave and surface plasmon wave on a metal surface in contact with an analyte to be measured.

In this measurement, as shown in FIG. 11, light emitted by a light source 9001 is focused by an entrance lens 9002 and enters a prism 9003. The light irradiates an Au film functioning as the measuring portion of a flow cell 9005 in tight contact with an upper surface 9004 of the prism 9003. An Au thin film is formed in the flow cell 9005. An analyte is set in contact with the surface of the Au thin film. The focused light which passed through the flow cell 9005 irradiates the lower surface of the Au thin film, and is reflected by the lower surface of the Au thin film. At this time, the intensity of the reflected light in a predetermined direction decreases in accordance with the presence/absence of the analyte owing to the surface plasmon resonance phenomenon. A photodetector 9006 formed from an image sensing element such as a CCD image sensor measures the intensity (light intensity). Then, a dip exhibiting a decrease in reflectance is observed at an angle at which the resonance occurs.

This measurement detects the presence/absence of an analyte which selectively binds to an antibody or DNA fragment immobilized on the surface (on the side of a detecting portion) of the Au film. In a state in which a sample solution is simply set at the detecting portion, a change caused by a reaction between the target analyte and the antibody and a change caused by a foreign substance settled and deposited on the detecting portion cannot be discriminated. Considering this, the sample solution is kept flowing at the detecting portion, suppressing sedimentation of a foreign substance. The change caused by a reaction can be selectively detected.

In this measurement, when a sample containing an analyte at a predetermined concentration is supplied at a predetermined flow rate to check a response such as an antigen-antibody reaction, the elapsed time (time during which the sample is supplied) of the reaction and the change amount of a signal (change amount of the SPR angle) obtained by a reaction between the analyte and the antibody have a nonlinear relationship. Further, the elapsed time of the reaction and the change amount of the signal change depending on the concentration of the analyte, a combination of the analyte and antibody, and the like. Quantitative determination of the analyte requires analysis, and real-time determination is difficult.

Under the circumstance, the 10th embodiment aims to provide a flow cell capable of easily analyzing a measurement result.

To solve the above problems, the flow cell according to the 10th embodiment is formed from a plate-like member having an opening, a fluidic channel having one end connected to the opening, and a pump which is connected to the other end of the fluidic channel and sucks, by the surface tension, a liquid that has reached the pump through the fluidic channel. The fluidic channel has a measuring portion for measuring a liquid. The pump is formed from a cavity which is formed in the plate-like member, and a plurality of pillars which are formed in the cavity. The surface area per unit volume in the cavity changes with the distance from the point of connection with the fluidic channel. The surface area per unit volume in the cavity may change in accordance with the characteristics of the liquid.

According to the 10th embodiment, since the surface area per unit volume in the cavity changes with the distance from the point of connection with the fluidic channel, the flow rate of a fluid flowing through the fluidic channel changes, and the measurement result of the fluid flowing through the measuring portion also changes. The surface area per unit volume in the cavity is set in advance in accordance with the distance from the point of connection with the fluidic channel so that the measurement result exhibits a predetermined profile. This facilitates the analysis of the measurement result.

<Structure of Flow Cell>

Details of a flow cell 110 according to the 10th embodiment will be described with reference to FIGS. 44 to 47.

As shown in FIGS. 44 to 47, the flow cell 110 according to the 10th embodiment is formed from a first substrate 111 which has an almost rectangular shape when viewed from the top, a sheet-like member 112 which is disposed on the first substrate 111, and a second substrate 113 which is disposed on the sheet-like member 112. The first substrate 111, sheet-like member 112, and second substrate 113 are stacked to form one plate-like member. The flow cell 110 includes an inlet port 114 which passes through the sheet-like member 112 and second substrate 113 and allows introducing a sample solution, two suction pumps 117 which are formed between the sheet-like member 112 and the second substrate 113, and a fluidic channel which connects the suction pumps 117 and the inlet port 114. The fluidic channel is made up of a measurement fluidic channel 115 which has one end connected to the inlet port 114 and is formed in the sheet-like member 112 interposed between the first substrate 111 and the second substrate 113, and a resistance fluidic channel 116 which has one end connected to the other end of the measurement fluidic channel 115 and is formed between the sheet-like member 112 and the second substrate 113.

<<First Substrate>>

The first substrate 111 is made of optical glass such as BK7, is about 1 mm in thickness, and has an almost rectangular shape about 16 mm on a side when viewed from the top. An Au layer 111a is formed by plating, vapor deposition, sputtering, or the like on the upper surface of the first substrate 111, i.e., a surface of the first substrate 111 on the side of the sheet-like member 112. Note that the Au layer 111a may be formed only at a portion corresponding to the measurement fluidic channel 115.

<<Sheet-Like Member>>

The sheet-like member 112 is formed from, e.g., a well-known adhesive tape about 10 μm to 150 μm in thickness, and has a planar shape corresponding to the first substrate 111. The sheet-like member 112 has a slit 1121 which is formed at almost the center and has an almost rectangular shape when viewed from the top, and an opening 1122 which is connected to one end of the slit 1121 and has an almost circular shape when viewed from the top. The slit 1121 is formed so that its longitudinal direction becomes almost parallel to any one side of the sheet-like member 112.

Together with the upper surface of the first substrate 111 and the lower surface of the second substrate 113, the slit 1121 forms the measurement fluidic channel 115 which is an almost rectangular parallelepiped space. A section of the measurement fluidic channel 115 that is perpendicular to the longitudinal direction has dimensions enough to cause capillary action with respect to an aqueous solution.

The sheet-like member 112 can be fabricated by, for example, processing an adhesive tape into a desired shape by a cutter, laser, or the like.

<<Structure of Second Substrate>>

The second substrate 113 is formed from, e.g., an acrylic substrate about 0.5 to 5 mm in thickness, and has a planar shape corresponding to the first substrate 111 and sheet-like member 112. A through hole 1131 is formed near the center of the second substrate 113 on its one side. The lower surface of the second substrate 113 has a meandering channel 1132 which is formed from almost the center to the vicinity of the other side opposite to the one side, and two cavities 1133 which are formed on the two sides of the meandering channel 1132.

The through hole 1131 has the same planar shape as that of the opening 1122.

The meandering channel 1132 has a crank-like planar shape with a plurality of bent portions. The bent portion is smoothly bent into an almost arcuate shape, i.e., curved shape. The other end of the meandering channel 1132 branches near the other side of the second substrate 113. The branches extend in opposite directions in the perpendicular direction and are connected to the adjacent cavities 1133, respectively.

The two cavities 1133 are formed from the lower surface toward the upper surface of the second substrate 113, and have an almost rectangular shape when viewed from the top. A plurality of almost columnar projections 1133a are formed in each cavity and project downward from its ceiling. By setting the projections 1133a to have an interval enough to cause capillary action, the cavity 1133 functions as the suction pump 117. The cavity 1133 is formed into an almost rectangular shape when viewed from the top. Vents 1133d and 1133e are formed at ends of the cavities 1133 near the one side. Vents 1133b and 1133c are formed at corners of the cavities 1133 near the other side that are opposite to corners connected to the branches of the other end of the meandering channel 1132. The vents 1133b to 1133e pass through the second substrate 113.

The projections 1133a are juxtaposed in the X and Y directions. The interval between adjacent projections 1133a and their diameter are changed depending on the position in the cavity 1133 in accordance with a desired flow rate profile of a sample solution in the flow cell 110 and the characteristics (e.g., viscosity) of a sample solution introduced into the flow cell 110. With this setting, the surface area per unit volume in the cavity 1133 changes depending on the position in the cavity 1133 in accordance with a desired flow rate profile of the sample solution and its characteristics.

Together with the opening 1122 and the upper surface of the first substrate 111, the through hole 1131 forms the inlet port 114 which is an almost columnar space with the upper surface of the first substrate defining its bottom.

When the second substrate 113 and sheet-like member 112 are brought into contact with each other, the meandering channel 1132 forms the meandering resistance fluidic channel 116. The resistance fluidic channel 116 has sectional dimensions enough to cause capillary action with respect to an aqueous solution.

The second substrate 113 can be fabricated by injection molding using a mold having a predetermined pattern, laser processing, cutting using an end mill, or the like.

<Method of Manufacturing Flow Cell>

A method of manufacturing the flow cell 110 according to the 10th embodiment will be exemplified. First, the sheet-like member 112 is placed on the first substrate 111. When the Au layer 111a is formed only at part of the first substrate 111, the sheet-like member 112 is placed on the first substrate 111 so that the slit 1121 for forming the measurement fluidic channel 115 is located on the Au layer 111a.

Then, the second substrate 113 is placed on the sheet-like member 112 so that the through hole 1131 and opening 1122 are connected to each other and one end of the meandering channel 1132 is positioned in the other end of the slit 1121.

After the first substrate 111, sheet-like member 112, and second substrate 113 are stacked in this way, they are pressed from the lower surface of the first substrate 111 and the upper surface of the second substrate 113. The first substrate 111 and second substrate 113 are fixed to each other via the sheet-like member 112 formed from a double-faced adhesive tape or the like, completing the flow cell 110 having the inlet port 114, measurement fluidic channel 115, resistance fluidic channel 116, and suction pumps 117.

<Operation of Flow Cell>

The operation of the flow cell 110 according to the 10th embodiment will be explained.

When a sample solution is injected from the inlet port 114, it proceeds sequentially through the measurement fluidic channel 115 and resistance fluidic channel 116 by capillary action, and flows into the suction pumps 117. In the suction pumps 117, a plurality of projections 1133a are formed to increase the surface area per unit volume, compared to a structure in which no projection 1133a is formed. The inside of the suction pump 117 has dimensions enough to cause capillary action. In the 10th embodiment, the shape and interval of the projections 1133a and the like are set so that the surface tension which acts on the liquid front of the sample solution in the suction pump 117 becomes larger than that which acts on the liquid front of the sample solution in the inlet port 114. Thus, the sample solution injected from the inlet port 114 passes through the measurement fluidic channel 115 and resistance fluidic channel 116, flows into the suction pumps 117, and proceeds through their insides.

The sample solution which has flowed into the suction pumps 117 proceeds through their insides owing to the surface tension. The magnitude of the surface tension acting on the sample solution depends on the surface area per unit volume. The surface tension acting on the sample solution increases as the surface area per unit volume increases. The sample solution proceeds through the inside of the suction pump 117 at high flow rate as if it was sucked by a strong suction force. Even in the measurement fluidic channel 115, the sample solution flows at a high flow rate. In contrast, if the surface area per unit volume is small, the surface tension acting on the sample solution becomes small and the sample solution proceeds through the suction pump 117 at a low flow rate. Even in the measurement fluidic channel 115, the sample solution flows at a low flow rate. In this fashion, the flow rate of the sample solution flowing through the measurement fluidic channel 115 depends on the surface area per unit volume in the suction pump 117. When the surface area per unit volume changes in the suction pump 117, the flow rate of the sample solution flowing through the measurement fluidic channel 15 also changes in response to this change.

Figure 48A:
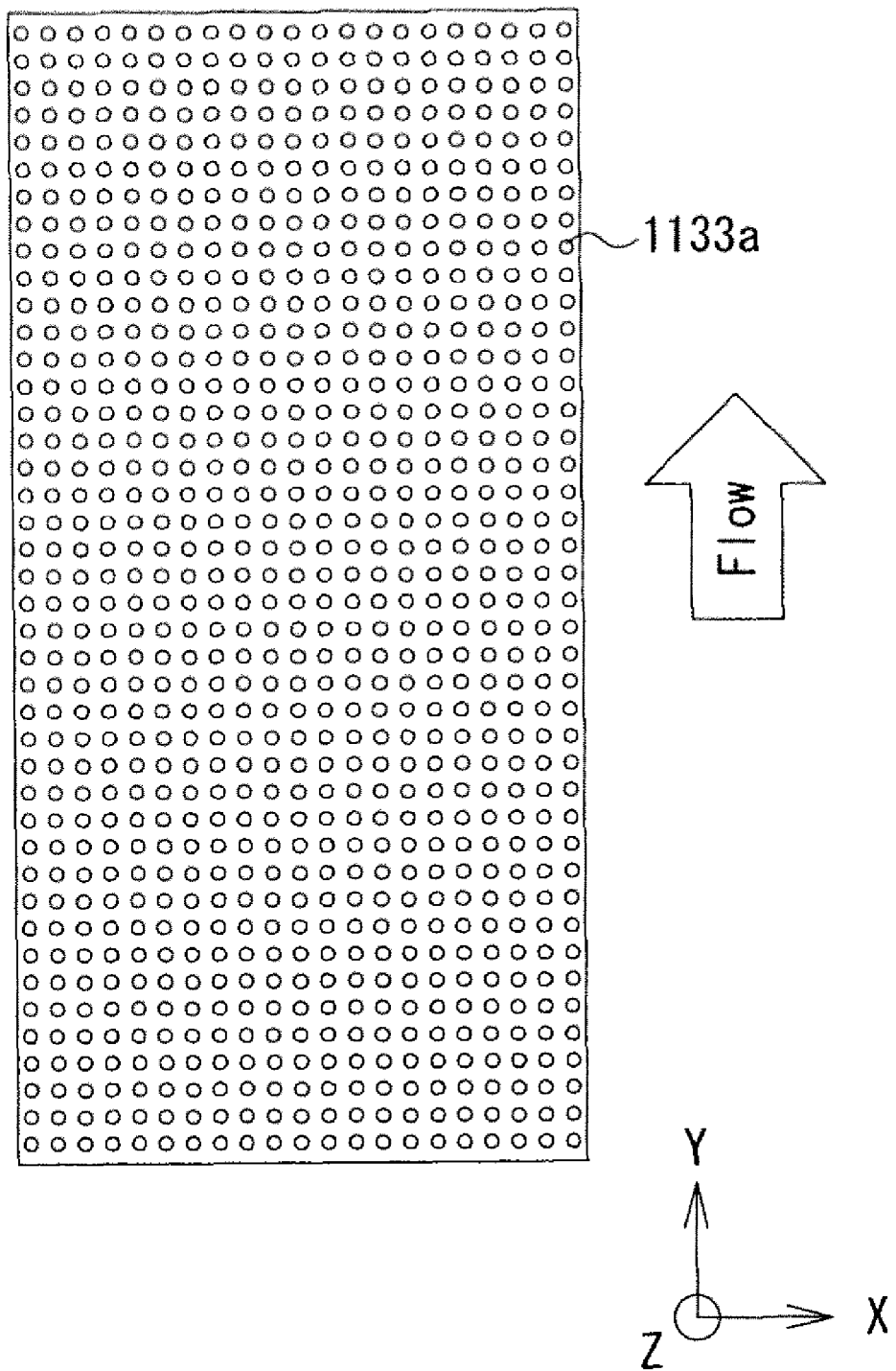
FIG. 48A is a plan view showing a cavity in which projections are formed uniformly.
Figure 48B:
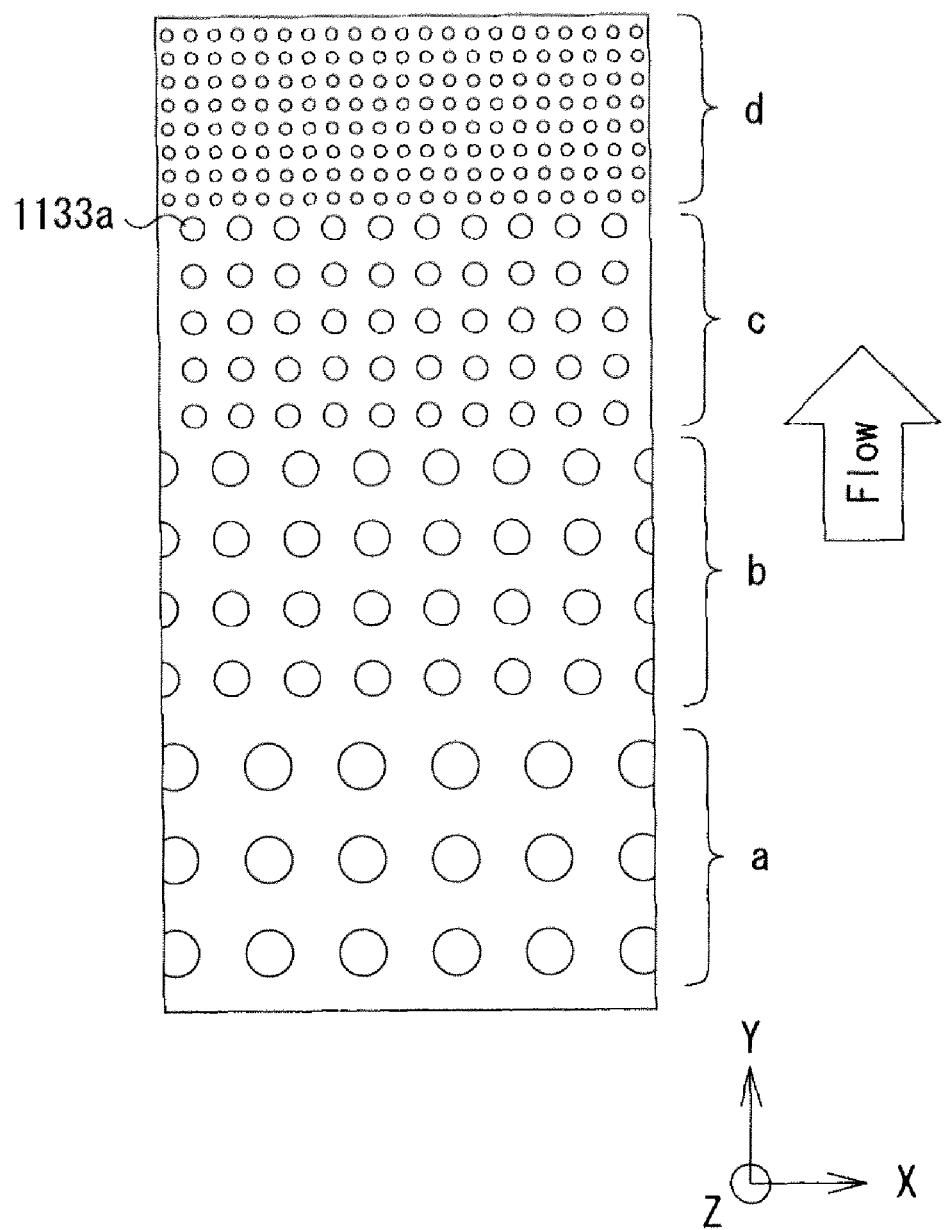
FIG. 48B is a plan view of the main part of a cavity in which the diameter and interval of projections are changed gradually.
Figure 49A:
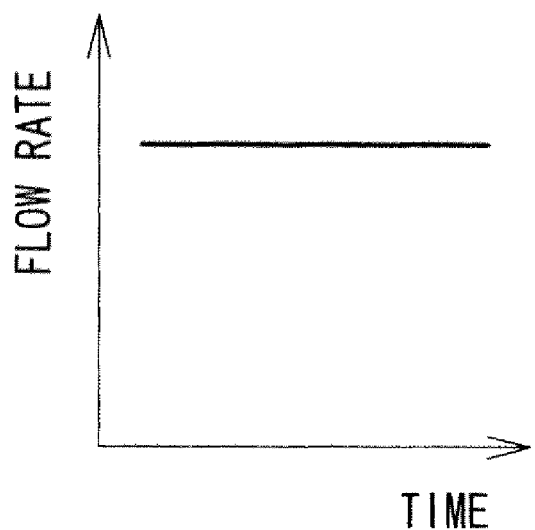
FIG. 49A is a graph showing the flow rate of a sample solution in a flow cell having the cavity in FIG. 48A.
Figure 50A:
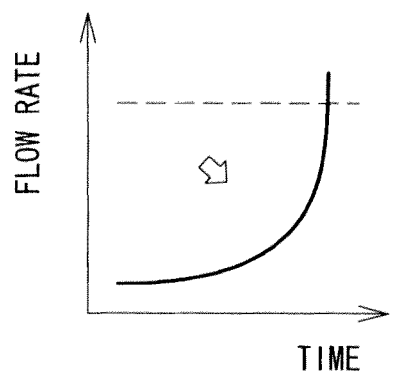
FIG. 50A is a graph showing the flow rate of a sample solution in a flow cell having the cavity in FIG. 48B.

When the resistance applied to the sample solution in the flow cell 110 is ignored and the projections 1133a are formed with the same diameter at equal intervals, as shown in FIG. 48A, the sample solution flows at a constant flow rate, as shown in FIG. 49A. To the contrary, when the projections 1133a are formed to gradually decrease their diameter and interval from a region a to a region d, as shown in FIG. 48B, the flow rate of the sample solution gradually increases, as shown in FIG. 50A. By appropriately setting the diameter and interval of the projections 1133a, the flow rate profile of the sample solution in the suction pump 117 can be controlled. The measurement result can be analyzed easily by setting the flow rate profile in accordance with the application purpose of the flow cell 110 and the characteristics of a sample solution. This principle will be explained below.

In a measurement apparatus as shown in FIG. 11, an antibody or DNA fragment is immobilized in the measurement fluidic channel 115 of the flow cell 110 to detect the presence/absence (biological reaction) of an analyte which selectively binds to the antibody or DNA fragment. In this case, when the measurement is done using the flow cell 110 having the projections 1133a which are formed with the same diameter at equal intervals, as shown in FIG. 48A, the flow rate in the measurement fluidic channel 115 of the flow cell 110 becomes constant, as shown in FIG. 49A. In the measurement using a constant flow rate, the quantity of biological reaction generally shows a curved profile, like an exponential function shown in FIG. 49B. That is, the quantity of biological reaction is large at the beginning, but becomes small gradually with the lapse of time.

The measurement apparatus generally determines, based on the measurement result, whether a sample solution contains a substance to be detected, or the amount of substance to be measured exceeds a threshold. Based on a measurement result with a profile like an exponential function shown in FIG. 49B, it is difficult to compare the threshold and measurement value with the naked eye, and the analysis of the measurement result is troublesome. If the measurement result or threshold has a simple profile such as a straight line, the measurement result can be easily analyzed even with the naked eye. Hence, in the 10th embodiment, the diameter and interval of the projections 1133a in the suction pump 117 are set in accordance with the characteristics of a sample solution. By changing the flow rate of a sample solution, the quantity of biological reaction is also changed so that the measurement result exhibits a desired profile.

Figure 49B:
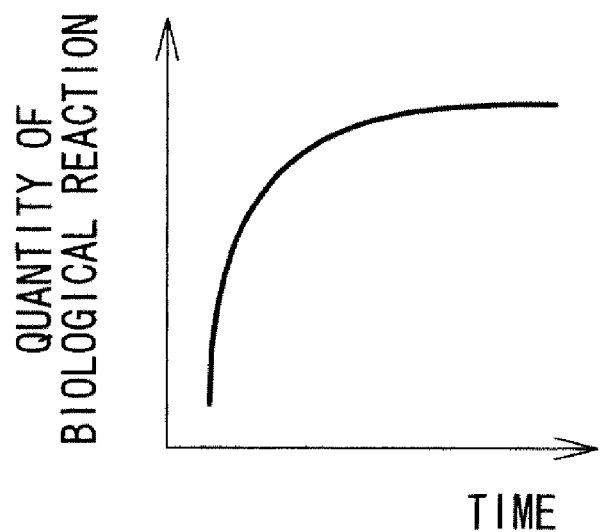
FIG. 49B is a graph showing the biological reaction in the case of FIG. 49A.
Figure 50B:
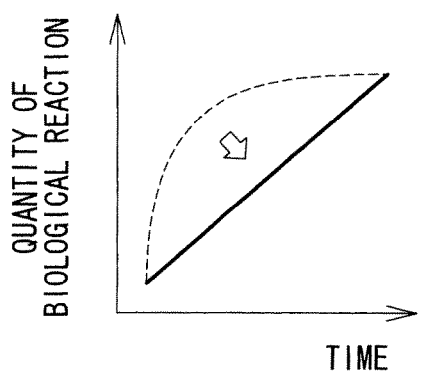
FIG. 50B is a graph showing the biological reaction in the case of FIG. 50A.

For example, it suffices to set the diameter and interval of the projections 1133*a* to show a flow rate profile from which a reaction profile of a linear function is obtained, as shown in FIG. 50B. More specifically, when the measurement result exhibits a curved profile as shown in FIG. 49B, the profile in FIG. 49B is converted to be axisymmetrical with respect to a liner function, as shown in FIG. 50B. The diameter and interval of the projections 1133*a* are set to obtain a flow rate having the converted profile. That is, the diameter and interval of the projections 1133*a* are changed in accordance with the distance from the point of connection with the measurement fluidic channel 115 so that the flow rate is low at the beginning and then gradually increases. In this case, for example, the density of projections 1133*a* is increased from the upstream side to downstream side of a sample solution, as shown in FIG. 48B. This structure can realize a flow rate profile as shown in FIG. 50A.

Figure 51:
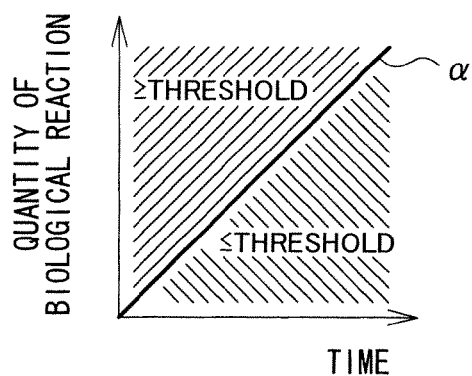
FIG. 51 is a graph showing the measurement result of a flow cell which is set so that the threshold draws a straight line.

For example, the diameter and interval of the projections 1133*a* are set in accordance with the distance from the point of connection with the measurement fluidic channel 115 so that the measurement result profile of a model sample solution or that of a sample solution corresponding to a threshold shows a linear function. With this setting, the flow rate of a sample solution in the measurement fluidic channel 115 is controlled to facilitate the analysis of the measurement result. More specifically, a flow cell 110 in which projections 1133*a* are arranged so that the threshold of the measurement result of a sample solution shows a profile of a straight line $\alpha$, as shown in FIG. 51, is formed in advance. By using the flow cell 110, a sample solution is measured. The obtained measurement result is compared with the profile of the straight line $\alpha$. The quantity of biological reaction of the sample fluid is equal to or larger than the threshold if the measurement result falls within the region above the straight line $\alpha$, and is equal to or smaller than the threshold if it falls within the region below the straight line $\alpha$. In this manner, the measurement result profile of a model sample solution or that of a sample solution corresponding to a threshold is set to represent a predetermined shape such as a linear function. The measurement result can be easily analyzed with the naked eye or the like.

As described above, according to the 10th embodiment, the measurement result is made to comply with a predetermined profile. For example, by only determining whether the measurement result falls within the region above or below a predetermined profile, it can be determined whether the measurement result is equal to or larger/smaller than a threshold. The measurement result profile changes depending on even the analyte concentration. However, all determinations can be made using the same protocol by setting the flow cell 110 in advance in accordance with various concentrations or setting the flow cell 110 so that all measurement results represent the same profile even for different analytes. This means that data of a reference measurement result is integrated in the flow cell 110 (e.g., a preset profile serves as reference data).

Not only determination with the naked eye but also determination using the measurement apparatus can be made easily. Conventionally, the measurement result is determined using a protocol of fitting the measurement result profile based on an exponential function or the like, and obtaining the gradient of the curve to measure the analyte concentration. Therefore, arithmetic processing and the like are cumbersome, and the measurement apparatus needs to have a certain level of performance. However, the flow cell 110 according to the 10th embodiment can reduce the arithmetic load, compared to the conventional measurement. This is because it suffices in threshold determination to determine whether the measurement result falls within the region above or below, e.g., a linear function. Even when the concentration or analyte is changed, the flow cell 110 is set so that the measurement result complies with a predetermined profile. The measurement apparatus can directly use the conventional protocol and does not require updating or the like.

The flow cell 110 according to the 10th embodiment is effective especially when the concentration of an analyte contained in a sample solution is low. This is because the measurement result, i.e., the antigen-antibody reaction depends on the flow rate of a sample solution flowing through the inside of the flow cell 110. When the analyte concentration is sufficiently high, analytes larger in number than those consumed by the antigen-antibody reaction are supplied even at low flow rate, and the flow rate does not have an influence. However, if the analyte concentration is low, the number of analytes consumable by a reaction per unit time becomes larger than that of flowing analytes, so the reaction becomes proportional to the flow rate (number of supplied analytes). In view of this, the width and interval of the projections 1133*a* in the suction pump 117 are adjusted to control the flow rate profile of a sample solution flowing through the inside of the flow cell 110, like the 10th embodiment. Even when a sample fluid having an analyte concentration at which the antigen-antibody reaction depends on the flow rate is used, a measurement result with a desired profile can be obtained, easily analyzing the measurement result.

Note that a preset measurement result profile is not limited to the above-mentioned linear function and can be freely set. Also, the method of acquiring a linear function profile is not limited to the above-mentioned axisymmetrical conversion, and various methods can be freely adopted, including a method of multiplying a measurement result by a predetermined coefficient or function.

In the 10th embodiment, the whole flow cell 110 has an almost rectangular shape when viewed from the top. However, the planar shape of the flow cell 110 is not limited to this and can be freely set in accordance with the shape of, e.g., a measurement apparatus in which the flow cell 110 is mounted.

In the 10th embodiment, the resistance fluidic channel 116 is arranged, but the measurement fluidic channel 115 and suction pumps 117 may be directly connected without arranging the resistance fluidic channel 116. Also, the shape of the resistance fluidic channel 116, i.e., that of the meandering channel 1132 is not limited to the above-mentioned crank shape and can be freely set.

In the 10th embodiment, the ends of the projections 1133*a* formed in the cavity 1133 contact the sheet-like member 112, but they may be open ends, i.e., they need not contact the sheet-like member. The internal capacity of the suction pump 117 is increased by an amount by which the projections 1133*a* are shortened, so the capacity of the suction pump 117 can be increased. Since the ends of the projections 1133*a*, and portions of the sheet-like member 112 that abut against these ends in a conventional structure are exposed, a large surface area can be ensured and in some cases, the surface area can be further increased, further increasing the suction force. For example, when a sample solution containing an impurity, such as food and drink or a body fluid, is injected into the flow cell, the inside of the suction pump 117 may be clogged with the impurity in a conventional structure. However, since the ends of the projections 1133*a* do not contact the sheet-like member 112, a gap is formed between them, as described above. The impurity can pass through the gap, preventing clogging of the inside of the suction pump 117 with the impurity.

In the 10th embodiment, the slit 1121 has an almost rectangular shape when viewed from the top, and is formed at almost the center of the sheet-like member 112. However, the shape and formation position of the slit 1121 are not limited to them and can be freely set as long as the slit 1121 passes above the Au layer 111a. Even the shape and position of the measurement fluidic channel 115 defined by the slit 1121 can be freely set.

In the 10th embodiment, the opening 1122 has an almost circular shape when viewed from the top. However, the shape of the opening 1122 is not limited to this and can be freely set as long as the opening 1122 exists at a position where it is connected to the through hole 1131 of the second substrate 113. Similarly, the shape of the inlet port 114 can also be freely set.

In the 10th embodiment, the cavity 1133 has an almost rectangular shape when viewed from the top. However, the planar shape of the cavity 1133 is not limited to this and can be freely set. Similarly, the shape of the projection 1133a formed in the cavity 1133 is not limited to an almost columnar shape and can be freely set as long as the surface area in the cavity 1133 increases.

In the 10th embodiment, the sheet-like member 112 is arranged, but the flow cell may be formed from the first substrate 111 and second substrate 113 without arranging the sheet-like member 112. In this case, the slit formed in the sheet-like member 112 is formed in the first substrate 111 or second substrate 113. A member to engage with the sides of the first substrate 111 and second substrate 113 is attached to join them. Alternatively, the first substrate 111 and second substrate 113 are bonded to each other using an adhesive or the like.

11th Embodiment

The 11th embodiment according to the present invention will be described.

Recently, measurement and analysis using a small amount of liquid have become popular, including micro-TAS, micro combinatorial chemistry, chemical IC, chemical sensor, biosensor, microanalysis, electrochemical analysis, QCM analysis, SPR analysis, and ATR analysis.

For example, SPR analysis described in reference 5 detects a pathogenic bacteria present in a liquid. For this purpose, a detecting portion supporting an antibody that reacts with an antigen originated from the pathogenic bacteria is arranged. A liquid to be measured is supplied onto the detecting portion to cause an antigen-antibody reaction. The reaction is detected by a surface plasmon resonance (SPR) method.

As a means for supplying a small amount of liquid, a flow cell is employed as described in, e.g., reference 4. In the flow cell, a plate-like member made of a synthetic resin or the like is micropatterned to form channels with various patterns, or the like. A capillary pump using capillary action transfers a liquid.

In the flow cell using the capillary pump described in reference 4, microchannels are formed in a silicon substrate (one substrate). A substrate (the other substrate) made of polydimethylsiloxane (PDMS) is stacked on the silicon substrate, forming a fluidic channel. One end of the fluidic channel is connected to a capillary pump. PDMS is a kind of silicone rubber and is very elastic. When the other substrate is stacked on one substrate in which a channel serving as a fluidic channel is formed, it is satisfactorily elastically deformed. The side wall of the channel and the other substrate come into tight contact with each other, preventing a gap from remaining, and a liquid from leaking from the fluidic channel.

A gap between the side wall of the channel and the other substrate can also be prevented from remaining, by interposing a seal member made of an elastic material between rigid substrates made of an acrylic resin or the like. Leakage of a liquid and the like can also be prevented.

However, when a PDMS substrate is used, the raw material cost is high, increasing the manufacturing cost of the flow cell. When, for example, the flow cell is set at a predetermined location in the surface plasmon resonance apparatus, the substrate itself elastically deforms, and the detecting portion supporting an antibody cannot be arranged at a predetermined position. Further, the substrate itself is poor in rigidity and readily deforms, and the fluidic channel may collapse.

The use of the seal member increases the number of components. In addition, it is difficult to handle a thin seal member, and the manufacturing cost of the flow cell increases.

The 11th embodiment has been made in consideration of this situation, and aims to provide a flow cell in which a fluidic channel is formed using rigid substrates not to leak a liquid, and the liquid can reliably flow through the fluidic channel.

To solve the above problems and achieve the object, a flow cell according to the 11th embodiment includes a first substrate, and a second substrate which is stacked on the first substrate. A plurality of pillars stand between the first and second substrates. The pillars include first and second pillars which are different in surface tension that acts on a liquid in contact with their outer surfaces. The pillars form a fluidic channel through which a liquid flows in a direction in which the first pillars are juxtaposed.

In the flow cell having this structure, a plurality of pillars including the first and second pillars which are different in surface tension that acts on a liquid in contact with their outer surfaces stand between the first and second substrates. The pillars form the fluidic channel through which a liquid flows in the direction in which the first pillars are juxtaposed. The fluidic channel can be formed using the difference in surface tension between the first and second pillars without forming channels in the first and second substrates.

More specifically, the surface tension is made different between the first and second pillars. A liquid is selectively transferred in the direction in which the first pillars are juxtaposed while preventing it from flowing toward a portion where the second pillars are formed. By using the difference in surface tension, the liquid flows along a line of first pillars even if a gap is formed on the side of the line of first pillars serving as a fluidic channel, thereby preventing leakage of the liquid. The 11th embodiment can provide a flow cell which prevents leakage of a liquid without bringing the first and second substrates into tight contact with each other.

It is preferable that the surfaces of the first pillars are hydrophilic and those of the second pillars are hydrophobic.

In this case, the surfaces of the first pillars are hydrophilic and are good in wettability, so a liquid flows toward the first pillars. In contrast, the surfaces of the second pillars are hydrophobic, are poor in wettability, and repel a liquid to prevent it from flowing toward the second pillars. Accordingly, the fluidic channel is formed in the direction in which the first pillars are juxtaposed.

It is preferable that the first pillars have a shape and arrangement which continuously generate a surface tension in the direction in which the fluidic channel extends, and the second pillars have a shape and arrangement which discretely generate a surface tension.

In this case, the first pillars have a shape and arrangement which continuously generate a surface tension in the direction in which the fluidic channel extends. By the surface tension, a liquid flows in the direction in which the fluidic channel extends. The second pillars have a shape and arrangement which discretely generate a surface tension, thereby preventing a liquid from flowing toward the second pillars.

It is preferable to employ a structure in which a section of the first pillar that is perpendicular to a direction in which the first pillar projects has an aspect ratio higher than 1, and the longitudinal direction of the section of the first pillar matches the direction in which the fluidic channel extends.

In this case, the aspect ratio of the section of the first pillar is higher than 1, i.e., the section of the first pillar is elongated in the longitudinal direction. The first pillar is disposed to make the longitudinal direction match the direction in which the fluidic channel extends. This structure has many portions at which the surface tension acts continuously in the direction in which the fluidic channel extends. By the surface tension, a liquid flows in the direction in which the fluidic channel extends.

It is preferable that at least one first pillar exists on a section perpendicular to the direction in which the fluidic channel extends.

In this case, the surface tension acts continuously in the direction in which the fluidic channel extends. By the surface tension, a liquid can be reliably transferred in the direction in which the fluidic channel extends.

It is also possible to adopt a structure in which at least a pair of lines of first pillars juxtaposed in the direction in which the fluidic channel extends is formed, and a passage having no pillar is formed between the paired lines of first pillars.

In this case, a liquid is sucked by the pair of lines of first pillars which are disposed on the two sides of the passage. By the suction force, the liquid flows through the passage. Since the passage having no pillar is formed, a detecting portion used to measure and analyze a liquid can be arranged in the passage.

Guide ribs which extend in the direction in which the fluidic channel extends may be formed in the passage. In this case, the surface tension which acts on the surfaces of the guide ribs acts continuously in the direction in which the fluidic channel extends. This promotes the flow of a liquid through the fluidic channel.

It is also possible to adopt a structure in which a gap in which no pillar is arranged on the first substrate is formed in part of the fluidic channel.

In this case, a detecting portion used to measure and analyze a liquid can be arranged in the gap on the first substrate side. The detecting portion can measure and analyze a liquid without interfering with a plurality of pillars.

It is preferable to form at least one of the first and second substrates from a light-transmissive material.

In this case, light can enter the flow cell from the outside of the first substrate, enabling measurement and analysis using light, like the surface plasmon resonance method.

The flow cell preferably includes an inlet port for introducing the liquid into the fluidic channel, and a pump for sucking the liquid in the fluidic channel.

In this case, a liquid introduced from the inlet port is sucked by the pump and can reliably flow through the fluidic channel. Since a liquid can flow without externally arranging a member such as a pump, measurement and analysis using the flow cell can be easily performed.

The 11th embodiment can provide a flow cell in which a fluidic channel is formed using rigid substrates not to leak a liquid, and the liquid can reliably flow through the fluidic channel.

<Structure of Flow Cell>

Figure 52:
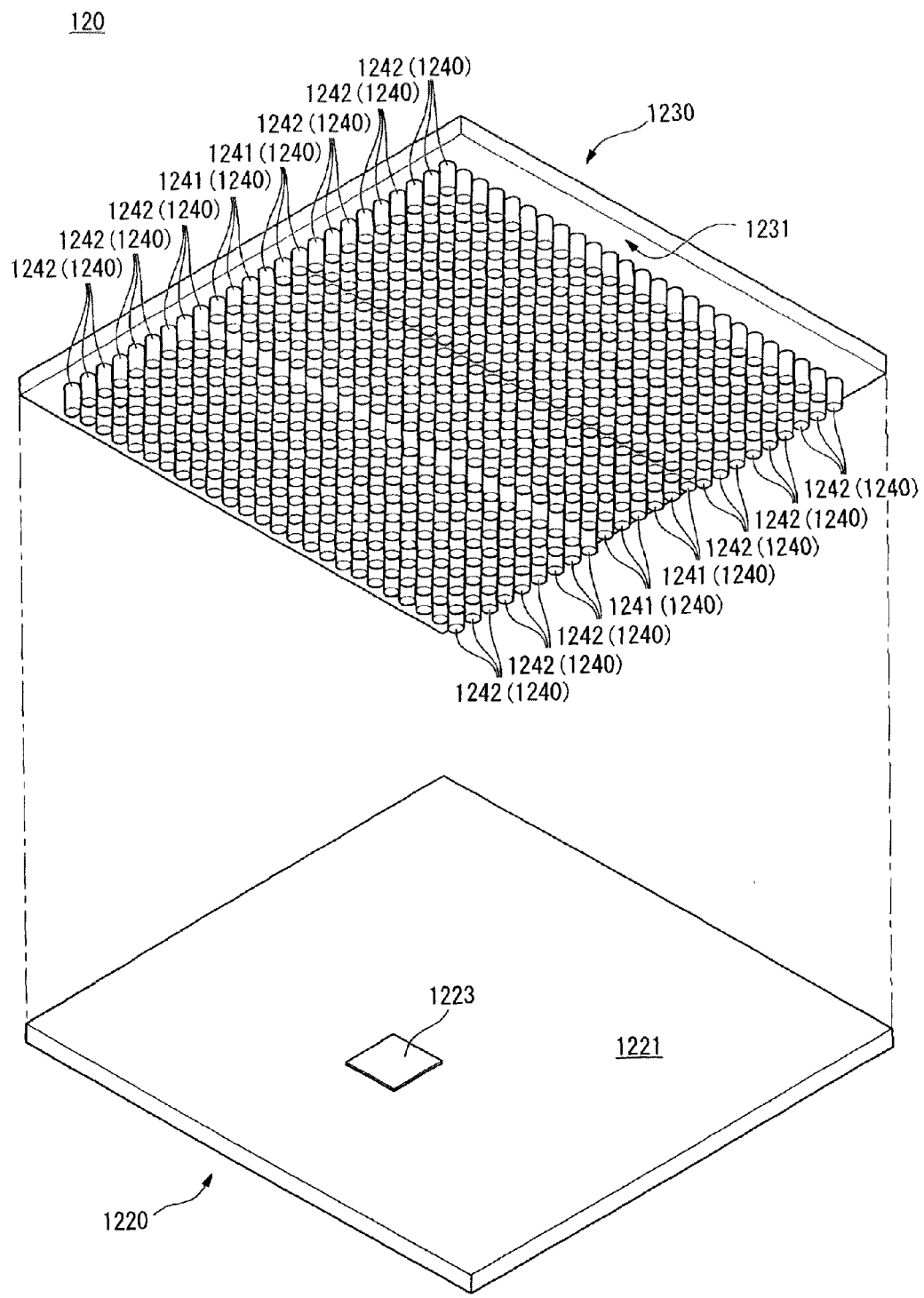
FIG. 52 is a perspective view of the first and second substrates which form a flow cell according to the 11th embodiment of the present invention.

Details of a flow cell according to the 11th embodiment of the present invention will be described with reference to FIGS. 52, 53, and 54.

A flow cell 120 according to the 11th embodiment includes a first substrate 1220, a second substrate 1230 which is stacked on the first substrate 1220, and a fluidic channel 1212 which is formed between the first substrate 1220 and the second substrate 1230.

The first substrate 1220 is made of a material which has relatively high rigidity and in which light is transmissive. In the 11th embodiment, the first substrate 1220 is made of a transparent glass substrate. The first substrate 1220 is a rectangular flat plate, and has an opposite surface 1221 which is arranged to face the second substrate 1230, and a bottom surface 1222 parallel to the opposite surface 1221. The opposite surface 1221 and bottom surface 1222 are smooth flat surfaces.

A detecting portion 1223 which reacts with a substance to be detected is arranged near the center of the opposite surface 1221. In the 11th embodiment, the detecting portion 1223 includes a metal film which is formed on the opposite surface 1221 and is 100 nm or less in thickness, and an antibody film applied on the metal film.

The second substrate 1230 is made of a synthetic resin such as a polymer. The second substrate 1230 is an almost rectangular flat plate, and has an opposite surface 1231 which is arranged to face the first substrate 1220, and an upper surface 1232 which extends parallel to the opposite surface 1231.

A plurality of pillars 1240 having a circular section stand on the opposite surface 1231 of the second substrate 1230. The pillars 1240 include first pillars 1241 and second pillars 1242 which are different in surface tension that acts on a liquid in contact with their outer surfaces.

Figure 53:
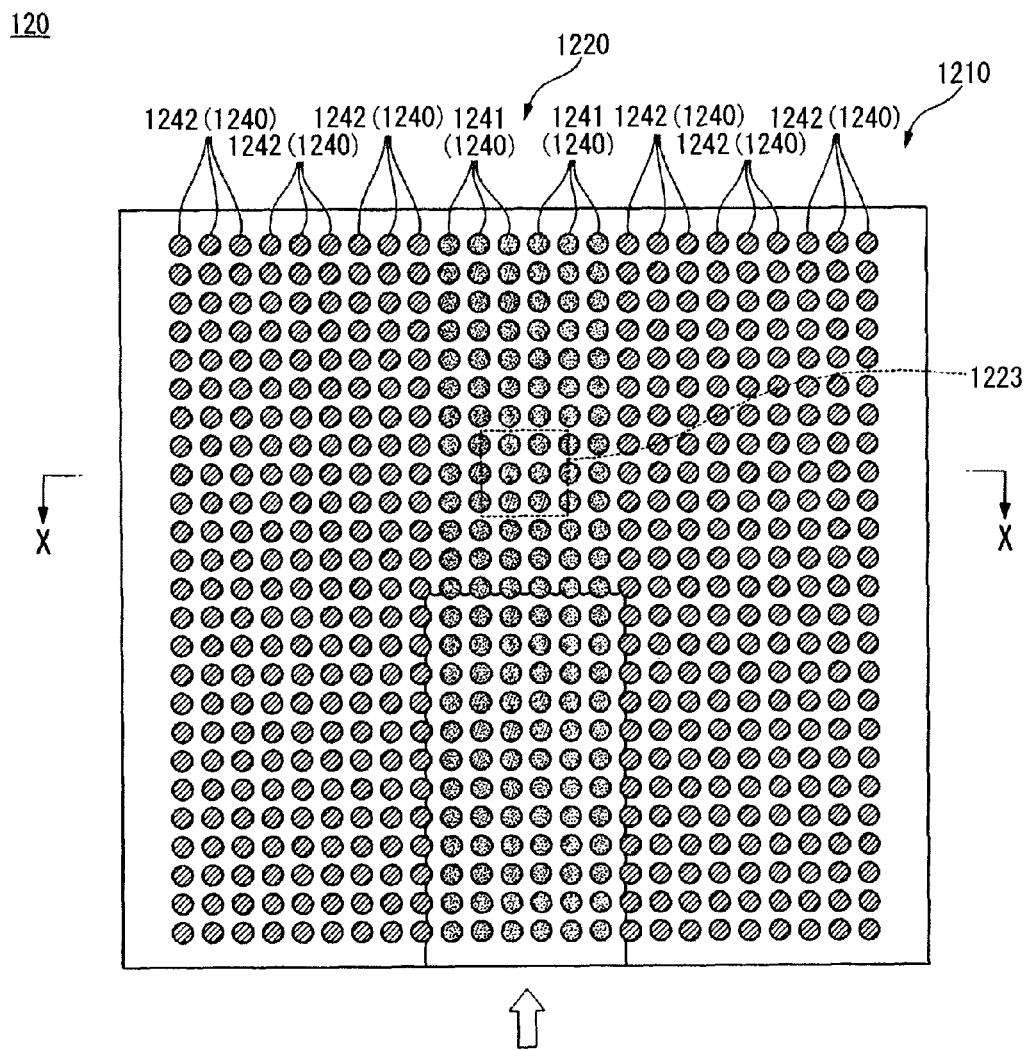
FIG. 53 is a view for explaining a section of the flow cell according to the 11th embodiment.

In the 11th embodiment, as shown in FIG. 53, the first pillars 1241 are arrayed from one end (lower side in FIG. 53) to the other end (upper side in FIG. 53) of the second substrate 1230. Six lines of first pillars 1241 are arranged. The second pillars 1242 are arranged on the two sides of lines of first pillars 1241. On each side, nine lines of second pillars 1242 are arranged.

In the 11th embodiment, the first pillars 1241 and second pillars 1242 are arranged at equal intervals, as shown in FIG. 53. As shown in FIG. 54, the first pillar 1241 is lower in projection height than the second pillar 1242.

The surfaces of the first pillars 1241 have undergone a hydrophilic treatment. The surfaces of the second pillars 1242 are hydrophobic. To make the surfaces of the first pillars 1241 hydrophilic, it suffices to apply a commercially available hydrophilic coating material such as "Lipidure" available from NOF Corporation.

The first substrate 1220 and second substrate 1230 are stacked, forming the flow cell 120 according to the 11th embodiment. At this time, the second pillars 1242 come into contact with the opposite surface 1221 of the first substrate 1220. However, the second pillars 1242 and the opposite surface 1221 of the first substrate 1220 need not be in tight contact with each other.

The first pillars 1241 and second pillars 1242 interposed between the first substrate 1220 and the second substrate 1230 form the fluidic channel 1212 through which the liquid flows.

Since the surfaces of the first pillars 1241 undergo a hydrophilic treatment and have good wettability with a liquid, the surface tension acts to suck in a liquid. In contrast, the surfaces of the second pillars 1242 are hydrophobic and have poor wettability with a liquid, so the surface tension acts to repel a liquid.

A liquid introduced into the fluidic channel 1212 proceeds in a direction in which the first pillars 1241 with good wettability are disposed, and does not proceed in a direction in which the second pillars 1242 with poor wettability are disposed. Hence, the liquid is selectively transferred in the direction in which the first pillars 1241 are arrayed.

Figure 54:
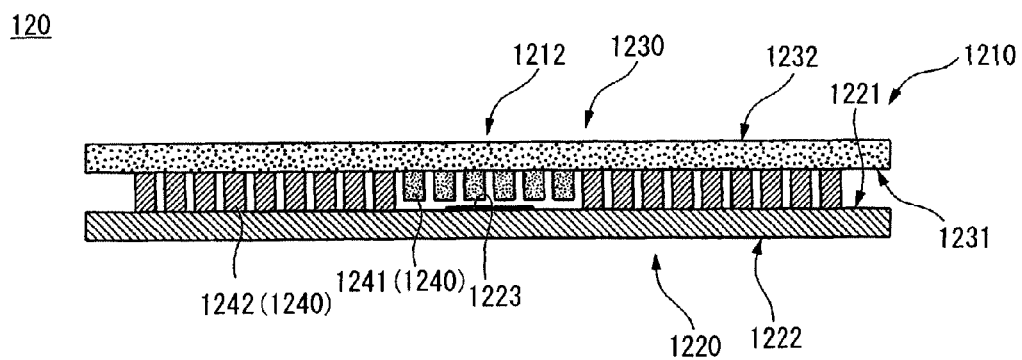
FIG. 54 is a sectional view taken along the line X-X in FIG. 53.

As shown in FIG. 54, the projection height of the first pillars 1241 is small to form a gap between the first pillars 1241 and the opposite surface 1221 of the first substrate 1220. The distal ends of the first pillars 1241 do not contact the detecting portion 1223.

<Example of Use of Flow Cell>

An example of the use of the flow cell according to the 11th embodiment will be explained.

The flow cell in the 11th embodiment is used as a measurement chip for a surface plasmon resonance measurement apparatus 9101.

An antibody which reacts with an antigen is applied to the detecting portion 1223 of the first substrate 1220.

Figure 55:
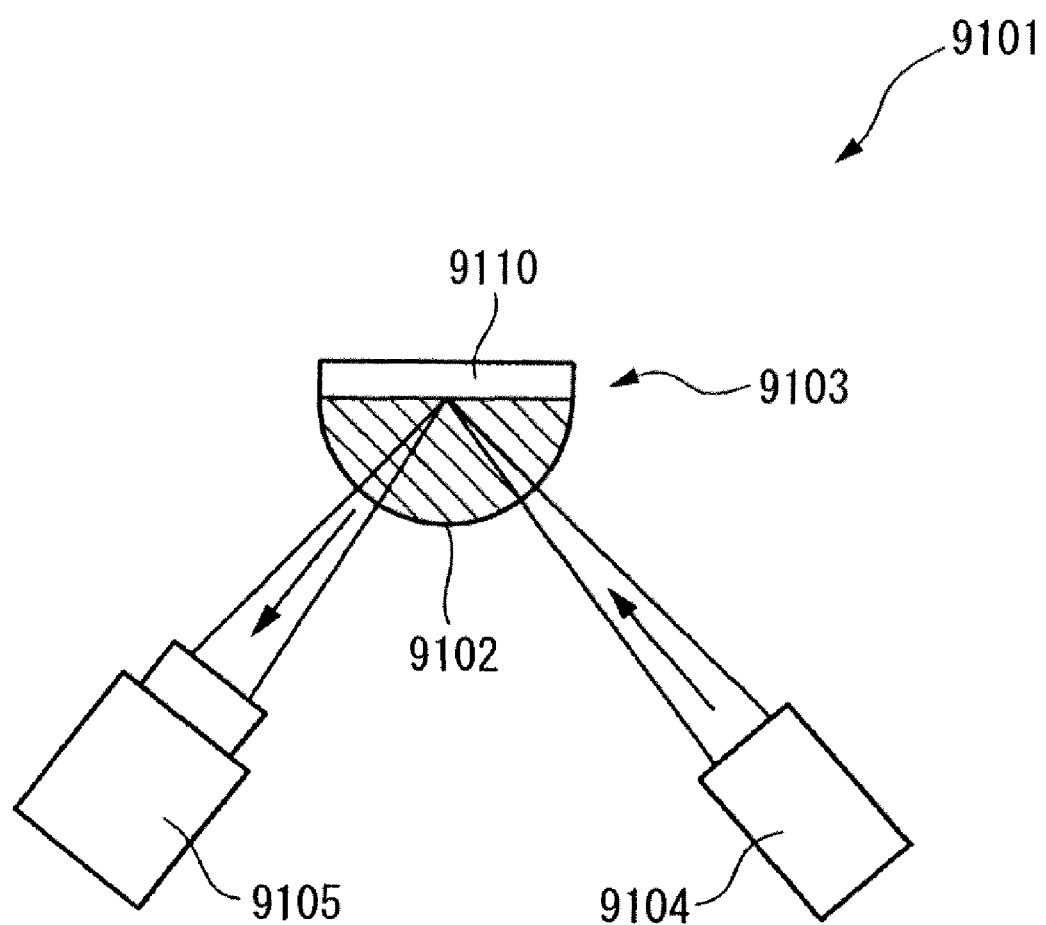
FIG. 55 is a schematic view showing the arrangement of a surface plasmon resonance measurement apparatus.

As shown in FIG. 55, the surface plasmon resonance measurement apparatus 9101 includes a semi-columnar prism 9102. Further, the surface plasmon resonance measurement apparatus 9101 includes a fixing portion 9103 at which the flow cell 120 in the 11th embodiment is fixed on the prism 9102, a laser emitting unit 9104 which emits a laser beam toward the detecting portion 1223 of the flow cell 120 via the prism 9102, and a laser detecting unit 9105 which detects the laser beam reflected by the detecting portion 1223.

The flow cell 120 in the 11th embodiment is fixed to the fixing portion 9103 so that the bottom surface 1222 of the first substrate 1220 faces the prism 9102.

When a liquid is introduced into the fluidic channel 1212 of the flow cell 120, it flows along the array of the first pillars 1241 and passes on the detecting portion 1223.

If an antigen exists in the liquid, the antigen in the liquid flowing through the fluidic channel 1212 and the antibody applied to the detecting portion 1223 cause an antigen-antibody reaction, changing the refractive index of the surface of the detecting portion 1223. This change is detected as a change of the frequency at which the surface plasmon and evanescent wave resonate, thereby determining the presence/absence of the antigen.

In the flow cell 120 of the 11th embodiment having this structure, the first pillars 1241 and the second pillars 1242 which are positioned outside the first pillars 1241 stand on the opposite surface 1231 of the second substrate 1230. The surfaces of the first pillars 1241 undergo a hydrophilic treatment, whereas those of the second pillars 1242 are hydrophobic. The first pillars 1241 and second pillars 1242 differ in surface tension which acts on a liquid in contact with their outer surfaces.

The surfaces of the first pillars 1241 undergo a hydrophilic treatment and are good in wettability, so a liquid flows toward the first pillars 1241. To the contrary, the surfaces of the second pillars 1242 are hydrophobic, are poor in wettability, and repel a liquid to prevent it from flowing toward the second pillars 1242. In this fashion, the fluidic channel 1212 is formed along the array of the first pillars 1241.

In the formed fluidic channel 1212, the second pillars 1242 are disposed outside the fluidic channel 1212. Even if a gap between the first substrate 1220 and the second substrate 1230 is formed outside the fluidic channel 1212, a liquid flows along the array of the first pillars 1241, preventing leakage of the liquid from this gap. The 11th embodiment can therefore provide the flow cell 120 which prevents leakage of a liquid without bringing the first substrate 1220 and second substrate 1230 into tight contact with each other. An elastically deformable seal member or the like need not be interposed between the first substrate 1220 and the second substrate 1230. The surface roughness of the opposite surface 1221 need not be excessively improved. The flow cell 120 can be manufactured at low cost.

The projection height of the first pillars 1241 is smaller than that of the second pillars 1242, and the distal ends of the first pillars 1241 do not contact the detecting portion 1223. When measuring a liquid, light neither interferes with the first pillars 1241, nor obstructs a reaction on the sensor surface. The liquid can be measured and analyzed with high precision.

In the 11th embodiment, the surface tension is made different between the first pillars 1241 and the second pillars 1242 by performing a hydrophilic treatment for only the first pillars 1241. That is, the first pillars 1241 and second pillars 1242 are formed by executing a hydrophilic treatment. The hydrophilic treatment is done for pillars 1240 at arbitrary positions among those arrayed at equal intervals, forming them as the first pillars 1241. The remaining pillars 1240 are formed as the second pillars 1242. The fluidic channel 1212 can be formed at an arbitrary position in an arbitrary direction.

12th Embodiment

The 12th embodiment according to the present invention will be described with reference to FIGS. 56, 57, and 58. The 12th embodiment is different from the 11th embodiment in the shapes and arrangements of first pillars 1341 and second pillars 1342.

Figure 56:
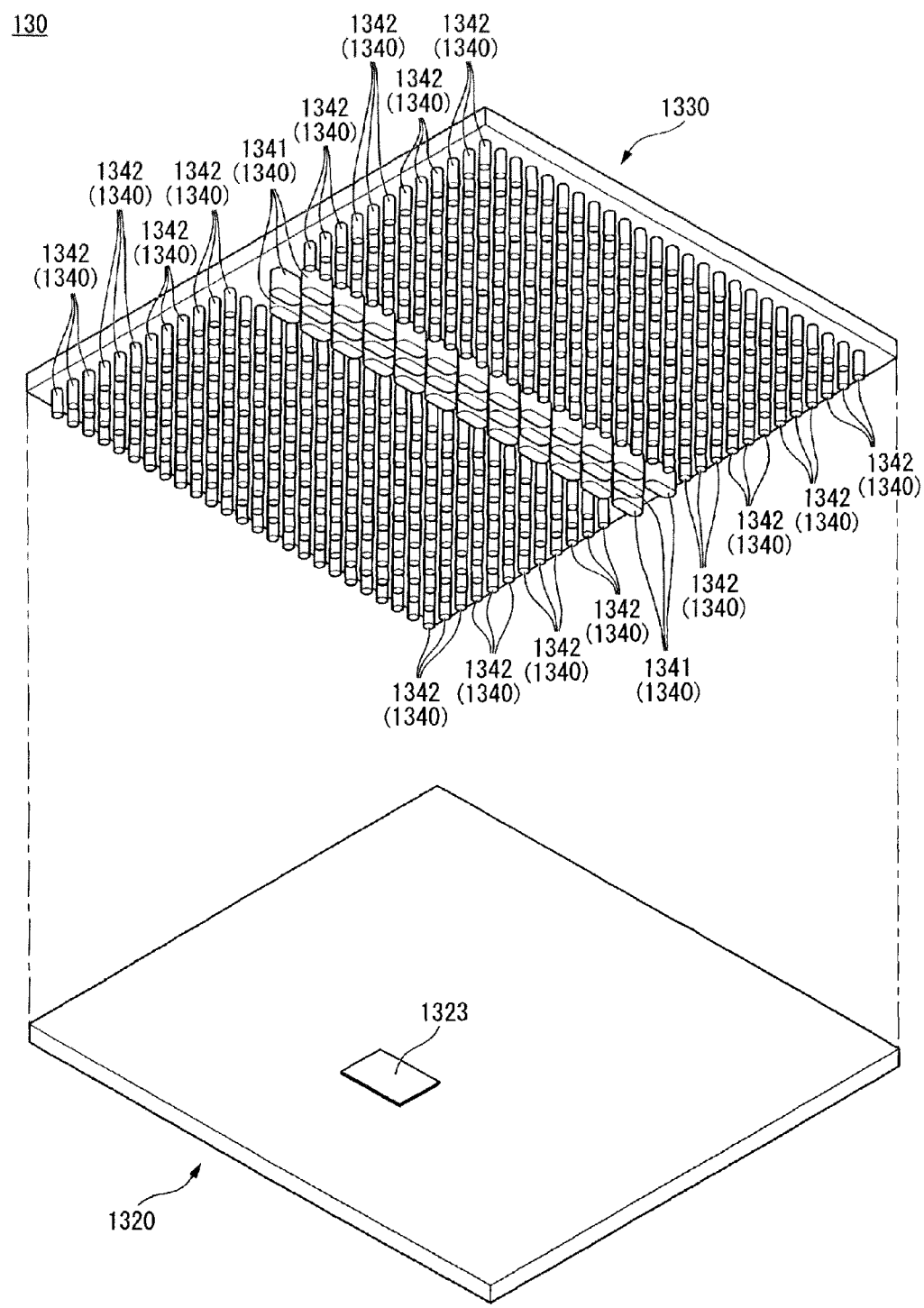
FIG. 56 is a perspective view of the first and second substrates which form a flow cell according to the 12th embodiment of the present invention.
Figure 57:
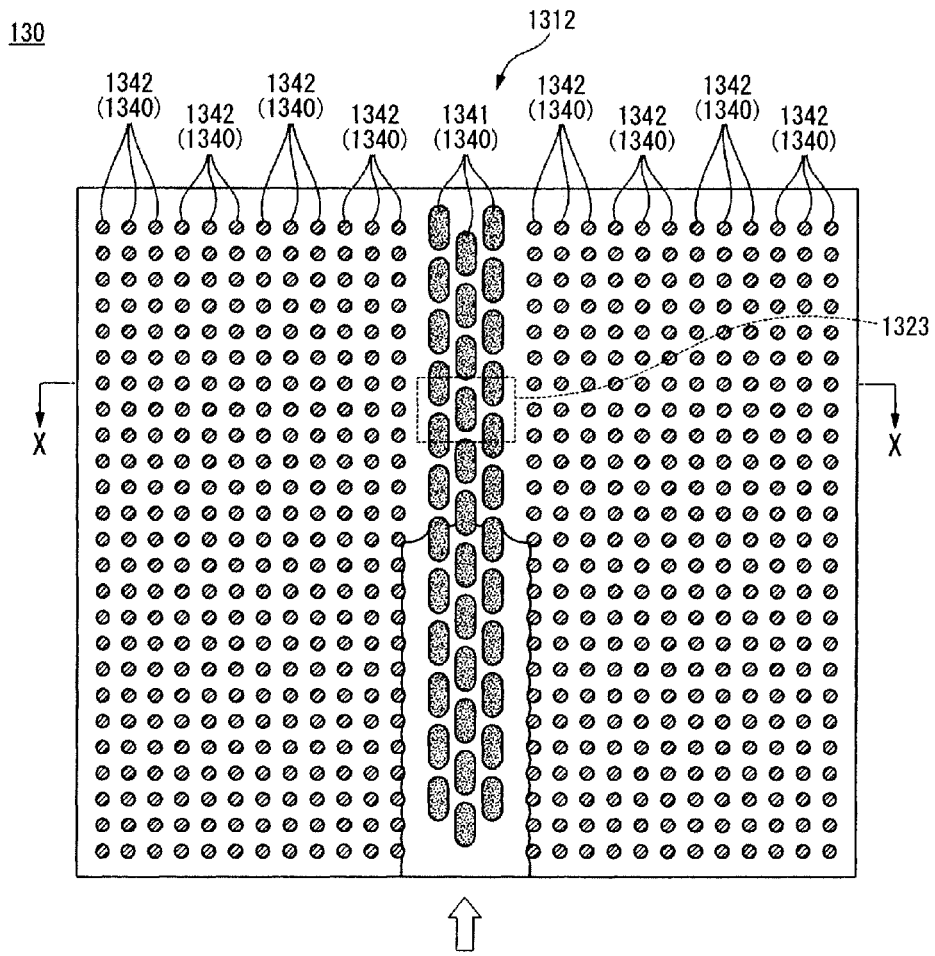
FIG. 57 is a view for explaining a section of the flow cell according to the 12th embodiment.
Figure 58:
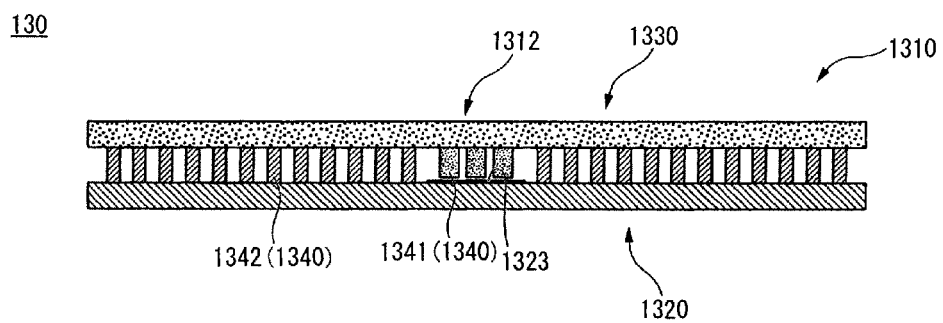
FIG. 58 is a sectional view taken along the line X-X in FIG. 57.

As shown in FIGS. 56 and 57, a section of the first pillar 1341 that is perpendicular to a direction in which the first pillar 1341 projects has an almost oval shape. The ratio of dimensions in the longitudinal and widthwise directions, i.e., aspect ratio $\gamma 1$ is set to be higher than 1. The first pillars 1341 are arranged so that their longitudinal direction matches a direction in which a fluidic channel 1312 extends. Three lines of first pillars 1341 are formed in the direction in which the fluidic channel 1312 extends. The first pillars 1341 on the center line are disposed at positions different from those of the first pillars 1341 on the right and left lines in the direction in which the fluidic channel 1312 extends. With this arrangement, at least one first pillar 1341 exists on a section perpendicular to the direction in which the fluidic channel 1312 extends.

As shown in FIGS. 56 and 57, a section of the second pillar 1342 that is perpendicular to a direction in which the second pillar 1342 projects has a circular shape. The ratio of dimensions in the longitudinal and widthwise directions, i.e., aspect ratio $\gamma 2$ is set to be 1. As shown in FIG. 57, the second pillars 1342 are arrayed to be discontinuous in any direction when viewed from the top.

In a flow cell 130 of the 12th embodiment having this structure, the surface tension acts continuously in the longitudinal direction of the first pillars 1341. The surface tension acts discretely in the widthwise direction of the first pillars 1341 and in any direction at portions where the second pillars 1342 are disposed. Then, a liquid selectively proceeds in the longitudinal direction of the first pillars 1341 in which the surface tension continuously acts. The first pillars 1341 and second pillars 1342 form the fluidic channel 1312.

The liquid does not proceed toward the second pillars 1342 on which the surface tension discretely acts. For this reason, an elastically deformable seal member or the like need not be interposed between a first substrate 1320 and a second substrate 1330. The surface roughness of an opposite surface 1321 of the first substrate 1320 need not be excessively improved. The flow cell 120 can be manufactured at low cost.

In the 12th embodiment, at least one first pillar 1341 is arranged on a section perpendicular to the direction in which the fluidic channel 1312 extends. The surface tension acts continuously in the direction in which the fluidic channel 1312 extends. The surface tension can reliably transfer a liquid in the direction in which the fluidic channel 1312 extends.

13th Embodiment

Figure 59:
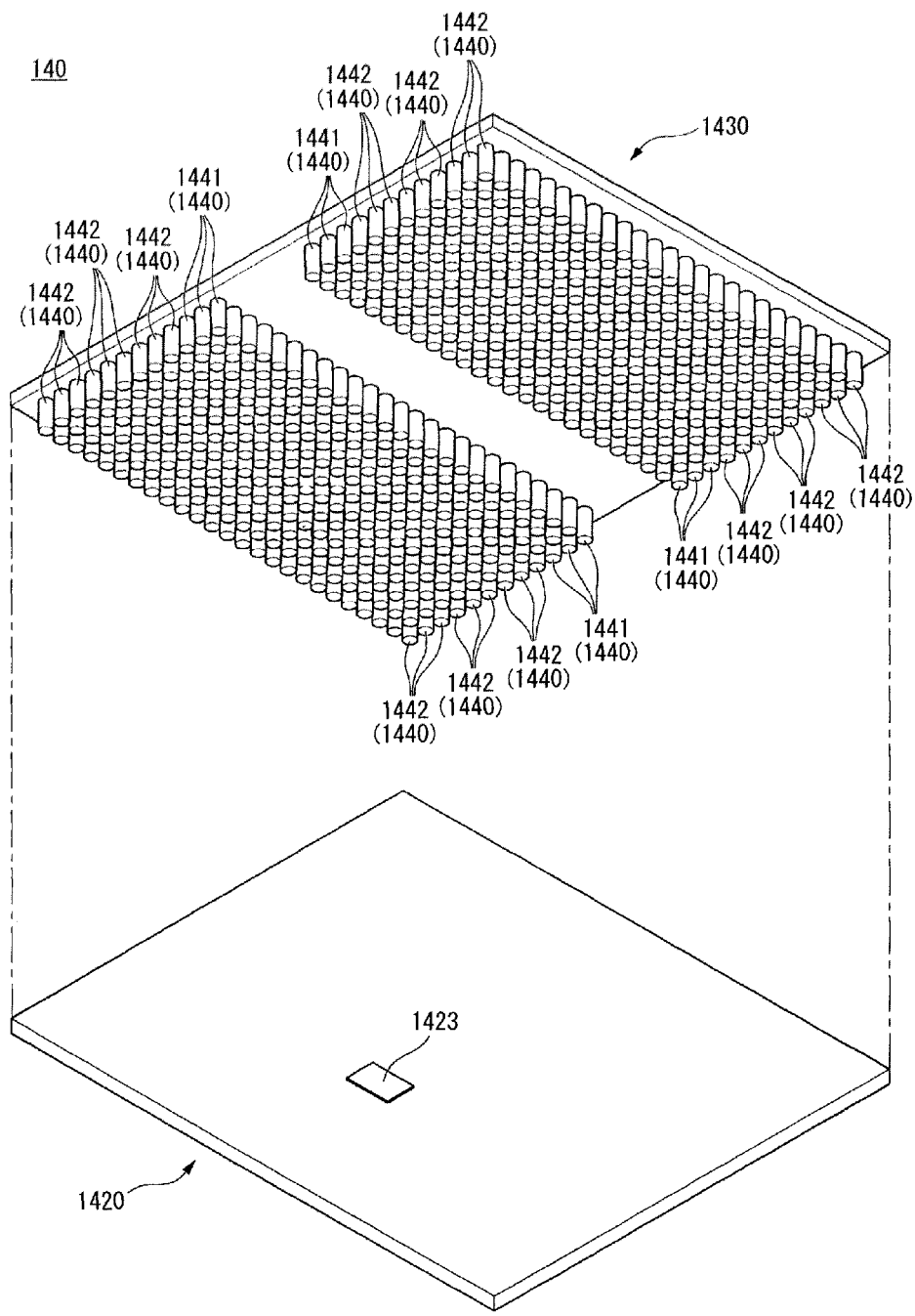
FIG. 59 is a perspective view of the first and second substrates which form a flow cell according to the 13th embodiment of the present invention.
Figure 60:
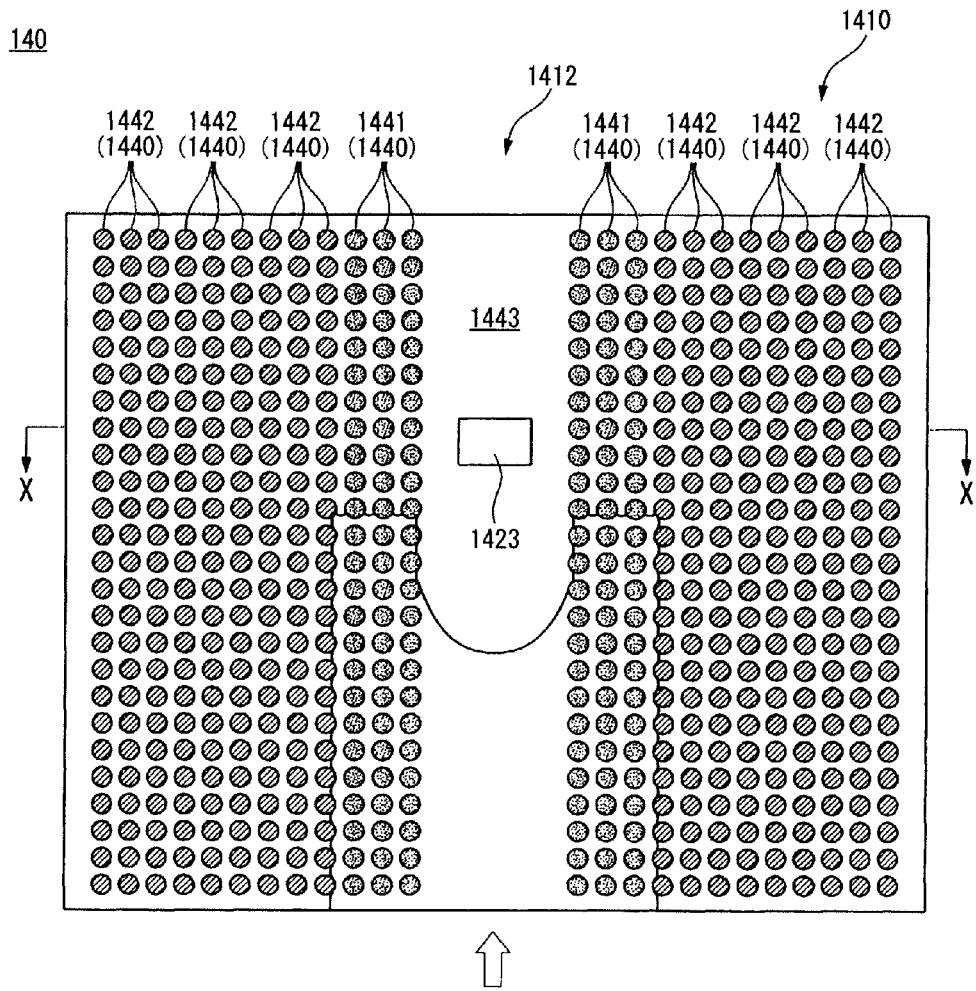
FIG. 60 is a view for explaining a section of the flow cell according to the 13th embodiment.
Figure 61:
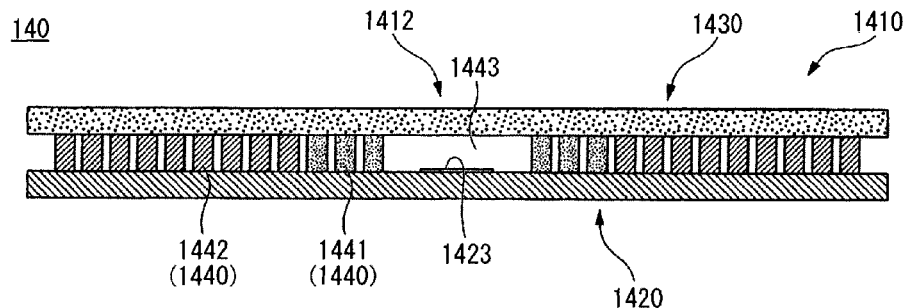
FIG. 61 is a sectional view taken along the line X-X in FIG. 60.

The 13th embodiment according to the present invention will be described with reference to FIGS. 59, 60, and 61. The 13th embodiment is different from the 11th embodiment in the arrangements of first pillars 1441 and second pillars 1442.

In a flow cell 140 according to the 13th embodiment, six lines of first pillars 1441 which are juxtaposed in the direction in which a fluidic channel 1412 extends are formed between a first substrate 1420 and a second substrate 1430. A passage 1443 having no pillar 1440 is formed at the center between the six lines of first pillars 1441. That is, three lines of first pillars 1441 are arranged on each side of the passage 1443. The second pillars 1442 are formed on the side of the first pillars 1441.

The surfaces of the first pillars 1441 have undergone a hydrophilic treatment and are made hydrophilic, whereas those of the second pillars 1442 are hydrophobic. The first pillars 1441 and second pillars 1442 differ in surface tension which acts on a liquid in contact with their outer surfaces.

In the flow cell 140 of the 13th embodiment having this structure, a liquid is sucked by a pair of line groups of first pillars 1441 which are disposed on the two sides of the passage 1443. By the suction force, the liquid flows through the passage 1443. Since the passage 1443 having no pillar 1440 is formed, a detecting portion 1423 can be arranged in the passage 1443.

Figure 62:
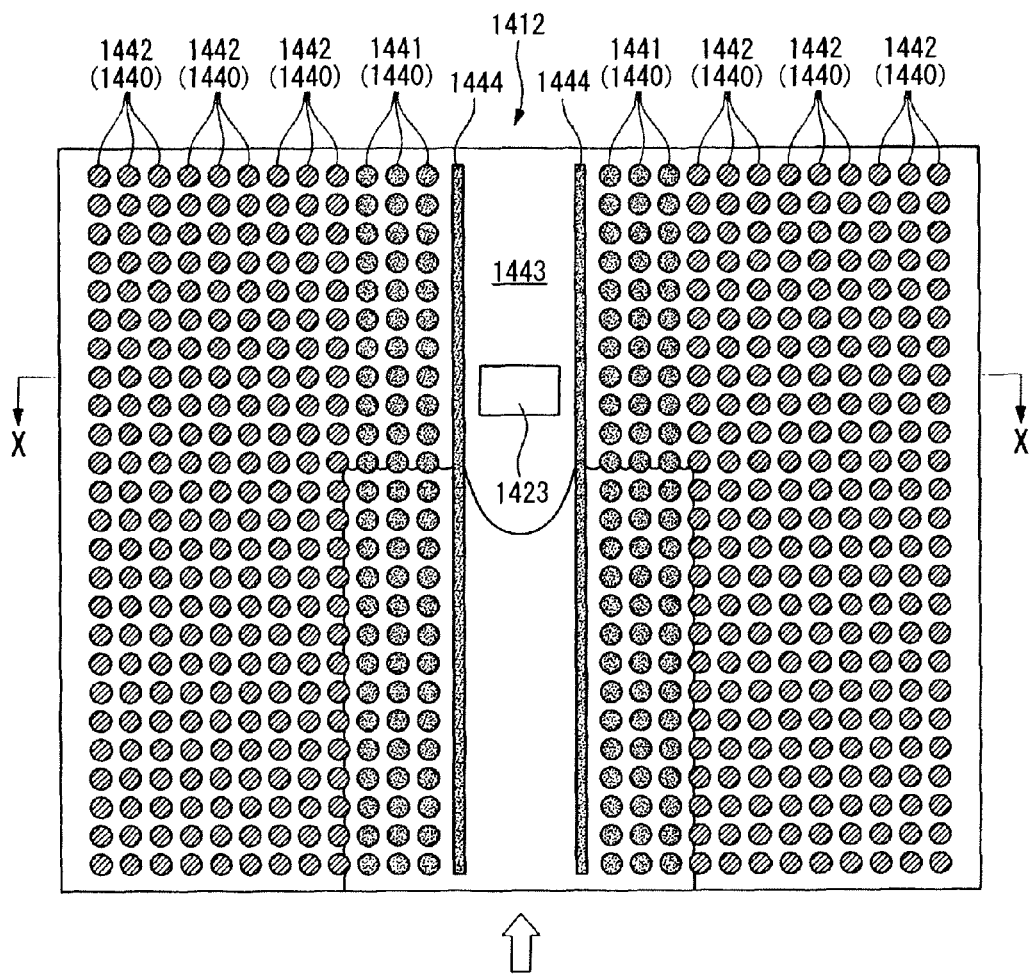
FIG. 62 is a view for explaining a section of a flow cell according to another embodiment.
Figure 63:
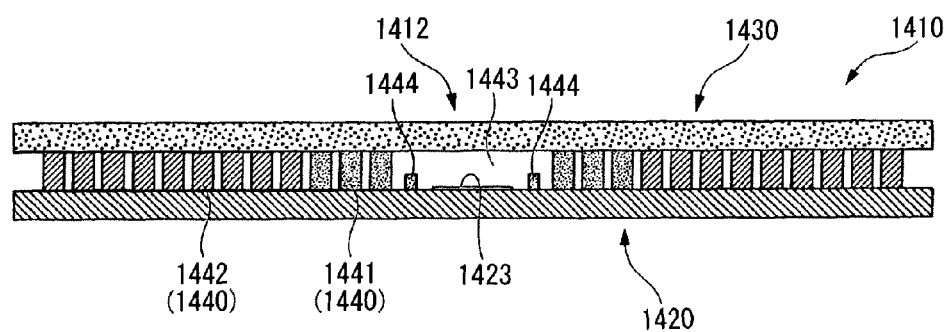
FIG. 63 is a sectional view taken along the line X-X in FIG. 62.

As shown in FIGS. 62 and 63, guide ribs 1444 which extend in the direction in which the fluidic channel 1412 extends and are lower in projection height than the pillar 1440 may be formed in the passage 1443. In this case, the surface tension which acts on the surfaces of the guide ribs 1444 acts continuously in the direction in which the fluidic channel 1412 extends. This further promotes the flow of a liquid through the fluidic channel 1412.

The flow cells 120 to 140 according to the embodiments of the present invention have been described. However, the technical scope of the present invention is not limited to them, and various changes and modifications can be made without departing from the technical concept of the invention.

For example, in the above description, the first substrate is formed from a glass substrate and the second substrate is made of a synthetic resin. However, the first and second substrates are not limited to them and may be made of a resin material, metal, ceramic, or the like.

In the above description, the flow cell is used in the surface plasmon resonance method. However, the flow cell is not limited to this and may be used in another analysis or the like.

Further in the above description, hydrophobic pillars are formed, and the surfaces of some of them undergo a hydrophilic treatment to form the first and second pillars. However, the present invention is not limited to this. For example, the first substrate may be formed from a hydrophobic material to form the second pillars to stand on it, and the second substrate may be formed from a hydrophilic material to form the first pillars to stand on it. To the contrary, the first substrate may be formed from a hydrophilic material to form the first pillars to stand on it, and the second substrate may be formed from a hydrophobic material to form the second pillars to stand on it.

In the above description, the fluidic channel is formed by a plurality of pillars which stand on the opposite surface of the second substrate. However, the present invention is not limited to this. A recessed channel may be formed in the opposite surface to dispose a plurality of pillars in it and form a fluidic channel.

Also, an inlet port for introducing a liquid into the fluidic channel may be formed to supply a liquid from the inlet port under pressure.

Moreover, an inlet port for introducing a liquid may be formed at one end of the fluidic channel, and a capillary pump may be formed at its other end to supply a liquid from the inlet port to the capillary pump.

14th Embodiment

The 14th embodiment according to the present invention will be explained.

Recently, measurement and analysis using a small amount of liquid have become popular, including micro-TAS, micro combinatorial chemistry, chemical IC, chemical sensor, biosensor, microanalysis, electrochemical analysis, QCM analysis, SPR analysis, and ATR analysis.

For example, SPR analysis described in reference 5 detects a pathogenic bacteria present in a liquid. For this purpose, a detecting portion supporting an antibody that reacts with an antigen originated from the pathogenic bacteria is arranged. A liquid to be measured is supplied onto the detecting portion to cause an antigen-antibody reaction. The reaction is detected by a surface plasmon resonance (SPR) method.

As a means for supplying a small amount of liquid, a flow cell is employed as described in, e.g., reference 4. In the flow cell, a plate-like member made of a synthetic resin or the like is micropatterned to form channels with various patterns, or the like. A capillary pump using capillary action transfers a liquid. In the flow cell described in reference 4, microchannels are formed in a silicon substrate. A substrate made of polydimethylsiloxane (PDMS) is stacked on the silicon substrate, forming a fluidic channel. One end of the fluidic channel is connected to a capillary pump.

There is also proposed a flow cell configured by interposing a seal member made of an elastic material between rigid substrates made of an acrylic resin or the like.

However, forming microchannels or the like in a substrate requires high-precision processing, greatly increasing the manufacturing cost of the flow cell.

To prevent leakage of a liquid from the fluidic channel, one substrate and the other substrate need to tightly contact with each other without any gap. However, it is difficult to equalize the surface roughnesses of one substrate and the other substrate with high precision when using an adhesive or the like or performing thermal welding. One substrate and the other substrate may be joined under high pressure to bring them into tight contact with each other. However, this greatly increases the manufacturing cost of the flow cell.

Conventionally, it is necessary to use a substrate made of an elastic material such as PDMS or interpose a seal member made of an elastic material. This further increases the manufacturing cost of the flow cell.

The 14th embodiment has been made in consideration of this situation, and aims to provide a flow cell which can be manufactured at low cost and in which substrates can be joined in tight contact with each other near the fluidic channel, and a method of manufacturing the flow cell.

To solve the above problems and achieve the object, a flow cell according to the 14th embodiment includes a first substrate, and a second substrate which is stacked on the first substrate. The first substrate has a plurality of first pillars which stand on an opposite surface that faces the second substrate. The second substrate has a plurality of second pillars which stand on an opposite surface that faces the first substrate. At junction portions at which the first and second pillars mesh with each other, the first and second substrates are joined. At a non-junction portion at which the first and second pillars do not mesh with each other, a fluidic channel through which a liquid flows is formed.

In the flow cell having this structure, the first pillars stand on the opposite surface of the first substrate, and the second pillars stand on the opposite surface of the second substrate. The flow cell has junction portions at which the first and second pillars mesh with each other. The first and second substrates can be joined and integrated without using an adhesive or the like.

Also, the flow cell has the non-junction portion at which the first and second pillars do not mesh with each other. At the non-junction portion, a fluidic channel through which a liquid flows is formed. The fluidic channel for a liquid can be formed without using a structure in which two substrates are completely tightly sealed. By arranging the junction portions near the fluidic channel, the first and second substrates can be joined near the fluidic channel.

It is preferable that the first pillars are arrayed at the non-junction portion in a direction in which the fluidic channel extends, the second pillars are arrayed between lines of first pillars and the junction portions, and at the non-junction portion, the first and second pillars are different in surface tension that acts on a liquid in contact with their outer surfaces.

In this case, the surface tension is made different between the first and second pillars, so a liquid is selectively transferred along the array of the first pillars, preventing the liquid from flowing toward a portion where the second pillars are formed. As a consequence, the fluidic channel can be formed at the non-junction portion.

It is preferable that the surfaces of the first pillars arrayed at the non-junction portion are hydrophilic and those of the second pillars arrayed between lines of first pillars and the junction portions are hydrophobic.

In this case, the surfaces of the first pillars arrayed at the non-junction portion are hydrophilic and are good in wettability, so a liquid flows toward the first pillars. Accordingly, the fluidic channel is formed along the array of the first pillars. In contrast, the surfaces of the second pillars arrayed between lines of first pillars and the junction portions are hydrophobic, are poor in wettability, and repel a liquid to prevent it from proceeding toward the second pillars. The first and second substrates are joined at the junction portions, providing a flow cell which prevents leakage of a liquid from the fluidic channel.

It is also possible to employ a structure in which the entire surface of the first substrate is hydrophilic and that of the second substrate is hydrophobic.

In this case, by using a hydrophilic substrate and hydrophobic substrate, the above-described flow cell can be relatively easily manufactured without performing a hydrophilic treatment and hydrophobic treatment for the first and second pillars.

It is preferable that the first pillars arrayed at the non-junction portion in the direction in which the fluidic channel extends have a shape and arrangement which continuously generate a surface tension in the direction in which the fluidic channel extends, and the second pillars arrayed between lines of first pillars and the junction portions have a shape and arrangement which discretely generate a surface tension.

In this case, the first pillars have a shape and arrangement which continuously generate a surface tension in the direction in which the fluidic channel extends. By this surface tension, a liquid flows in the direction in which the fluidic channel extends. The second pillars arrayed between lines of first pillars and the junction portions have a shape and arrangement which discretely generate a surface tension, thereby preventing a liquid from proceeding toward the second pillars.

It is preferable to employ a structure in which the aspect ratio of the section of the first pillar is higher than 1, and the longitudinal direction of the section of the first pillar matches the direction in which the fluidic channel extends. In this case, the aspect ratio of the section of the first pillar is higher than 1, i.e., the section of the first pillar is elongated in the longitudinal direction. The first pillar is disposed to make the longitudinal direction match the direction in which the fluidic channel extends. The surface tension acts continuously in the direction in which the fluidic channel extends. By the surface tension, a liquid flows in the direction in which the fluidic channel extends.

It is also possible to form at least a pair of lines of first pillars juxtaposed in the direction in which the fluidic channel extends, and form, between the paired lines of first pillars, a passage having neither the first pillar nor second pillar.

In this case, a liquid is sucked by the pair of lines of first pillars which are disposed on the two sides of the passage. By the suction force, the liquid flows through the passage. Since the passage having neither the first pillar nor second pillar is formed, a detecting portion used to measure and analyze a liquid can be arranged in the passage.

Guide ribs which extend in the direction in which the fluidic channel extends may be formed in the passage.

In this case, the guide ribs make the surface tension to act continuously in the direction in which the fluidic channel extends. This promotes the flow of a liquid through the fluidic channel.

The first substrate or second substrate may be made of a light-transmissive material.

In this case, light can enter the flow cell from the outside of the first substrate or second substrate, enabling measurement and analysis using light, like the surface plasmon resonance method.

The flow cell preferably includes an inlet port for introducing the liquid into the fluidic channel, and a pump for sucking the liquid in the fluidic channel.

In this case, a liquid introduced from the inlet port is sucked by the pump and can reliably flow through the fluidic channel. Since a liquid can flow without externally arranging a member such as a pump, measurement and analysis using the flow cell can be easily performed.

A method of manufacturing a flow cell according to the 14th embodiment is characterized by joining a first substrate and a second substrate so that a plurality of pillars that stand on the opposite surface of the first substrate and a plurality of second pillars that stand on the opposite surface of the second substrate mesh with each other, and forming, at a non-junction portion at which the first pillars and second pillars do not mesh with each other, a fluidic channel through which a liquid flows.

According to the flow cell manufacturing method having these steps, the first and second substrates can be joined and integrated without using an adhesive or the like. The flow cell can be manufactured at low cost.

The 14th embodiment can provide a flow cell which can be manufactured at low cost and in which substrates can be joined in tight contact with each other near the fluidic channel, and a method of manufacturing the flow cell.

<Structure of Flow Cell>

Details of a flow cell according to the 14th embodiment of the present invention will be described with reference to FIGS. 64 to 66.

A flow cell 150 according to the 14th embodiment is formed by stacking a first substrate 1520 and second substrate 1530. The flow cell 150 incorporates a fluidic channel 1512 through which a liquid flows.

Figure 64:
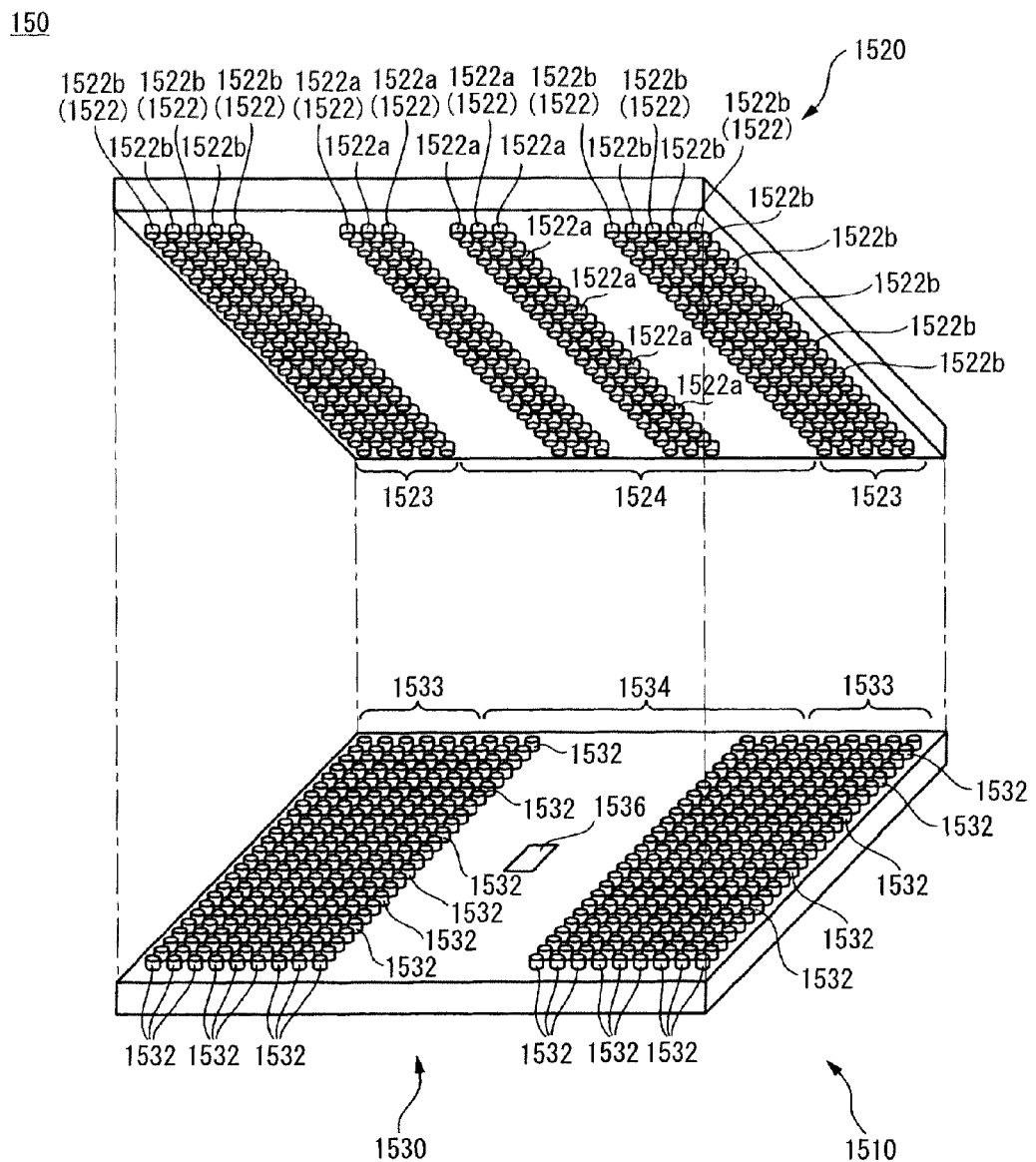
FIG. 64 is a perspective view of the first and second substrates which form a flow cell according to the 14th embodiment.

As shown in FIG. 64, the first substrate 1520 is a rectangular flat plate. A plurality of first columnar pillars 1522 stand on an opposite surface of the first substrate 1520 that is arranged to face the second substrate 1530. The first substrate 1520 is made of a synthetic resin such as a polymer resin. The entire surface of the first substrate 1520 is hydrophilic by a hydrophilic treatment, and the outer surfaces of the first pillars 1522 are also hydrophilic.

The first pillars 1522 are arrayed from one end (lower right side in FIG. 64) to the other end (upper left side in FIG. 64) of the first substrate 1520. Junction regions 1523 in each of which five lines of first pillars 1522*b* are arrayed are formed on sides (right and left sides in FIG. 64) on the first substrate 1520. A non-junction region 1524 where three lines of first pillars 1522*a* are arrayed on each side is formed between the junction regions 1523.

As shown in FIG. 64, the second substrate 1530 is a rectangular flat plate. A plurality of second columnar pillars 1532 stand on an opposite surface of the second substrate 1530 that is arranged to face the first substrate 1520. The second substrate 1530 is made of a material which has relatively high rigidity and in which light is transmissive. In the 14th embodiment, the second substrate 1530 is made of a transparent polymer resin. The entire surface of the second substrate 1530 is hydrophobic, and the outer surfaces of the second pillars 1532 are also hydrophobic.

The second pillars 1532 are arrayed from one end (upper right side in FIG. 64) to the other end (lower left side in FIG. 64) of the second substrate 1530. Junction regions 1533 in each of which six lines of second pillars 1532 are arrayed are formed on sides (right and left sides in FIG. 64) on the second substrate 1530. A non-junction region 1534 where three lines of second pillars 1532 are arrayed on each side is formed between the junction regions 1533.

A detecting portion 1536 supporting an antibody that reacts with a substance to be detected is arranged near the center of the opposite surface of the second substrate 1530, i.e., the center of the non-junction region 1534. In the 14th embodiment, the detecting portion 1536 includes a metal film which is formed on the opposite surface and is 100 nm or less in thickness, and an antibody film applied on the metal film.

The first substrate 1520 and second substrate 1530 are stacked while their opposite surfaces face each other. In the junction regions 1523 and 1533, as shown in FIG. 65, the first pillars 1522*b* and second pillars 1532 mesh with each other so that the second pillars 1532 of the second substrate 1530 enter the intervals between the first pillars 1522*b* of the first substrate 1520, thereby forming junction portions 1513. By forming the junction portions 1513 in this way, the first substrate 1520 and second substrate 1530 are joined to each other, forming the flow cell 150 according to the 14th embodiment.

Figure 65:
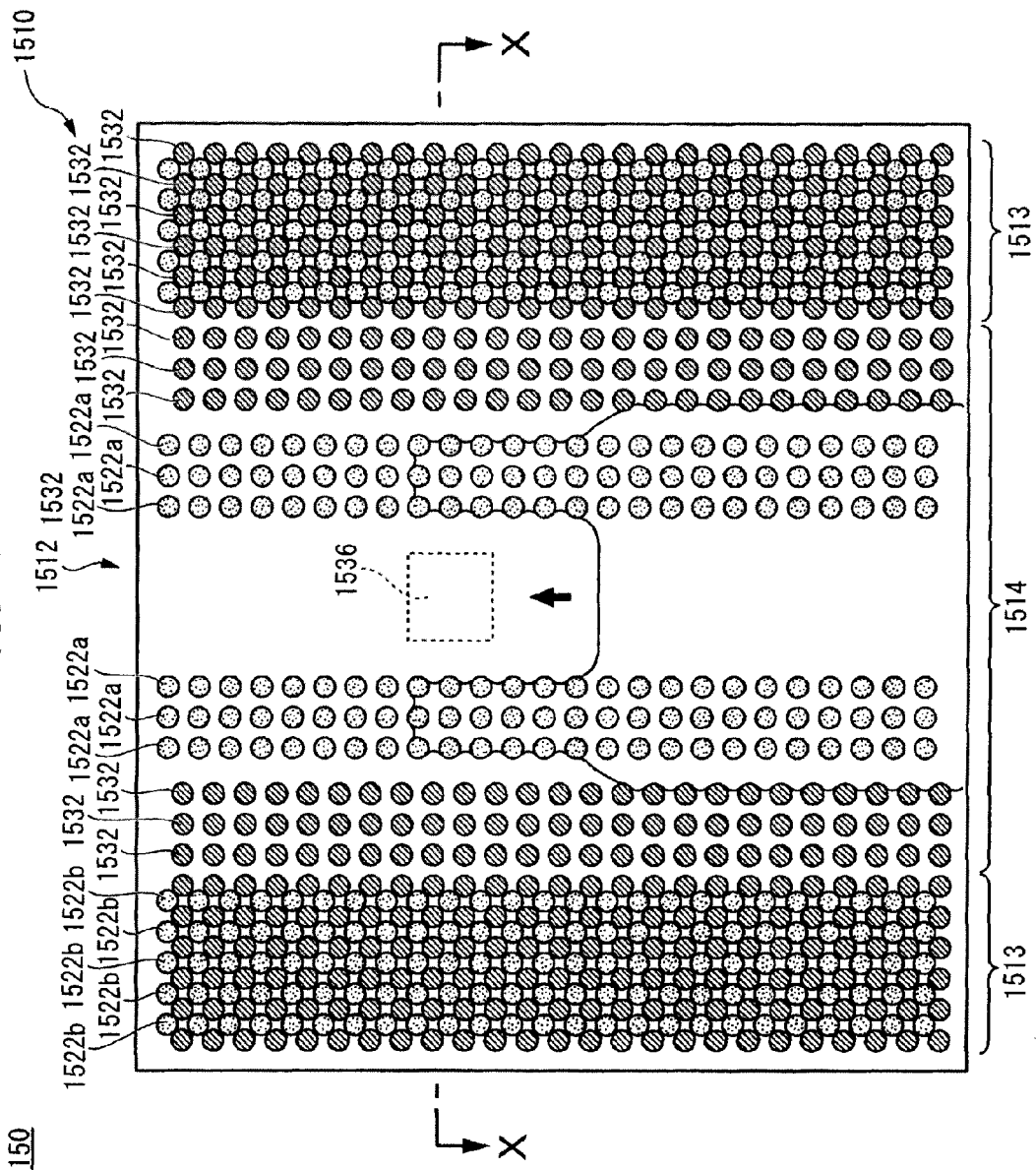
FIG. 65 is a view for explaining the section of the flow cell according to the 14th embodiment of the present invention.
Figure 66:
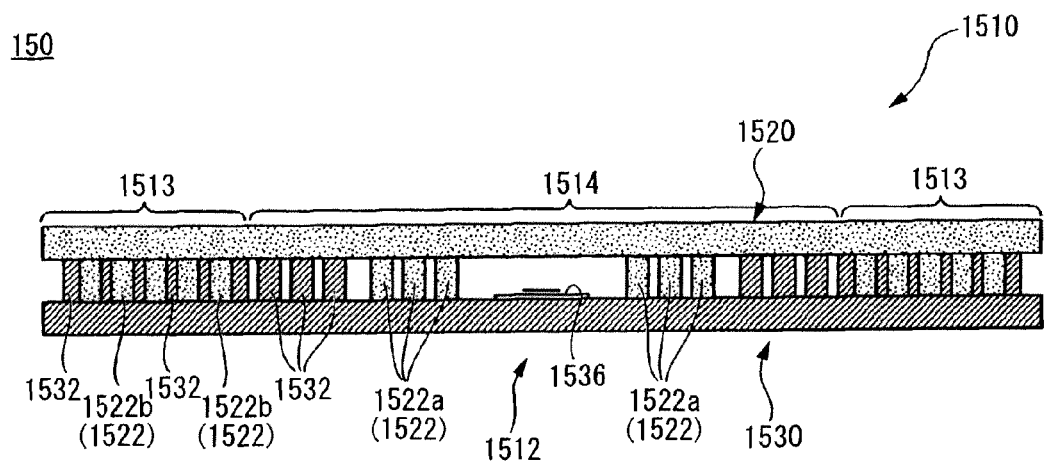
FIG. 66 is a sectional view taken along the line X-X in FIG. 65.

As shown in FIG. 65, lines of first pillars 1522*a* disposed in the non-junction region 1524 of the first substrate 1520 are interposed between lines of second pillars 1532 disposed in the non-junction regions 1534 of the second substrate 1530. As a result, a non-junction portion 1514 is formed, at which the first pillars 1522*a* and second pillars 1532 do not mesh with each other.

At the non-junction portion 1514, the fluidic channel 1512 is defined by the first pillars 1522*a* disposed in the non-junction region 1524 of the first substrate 1520 and the second pillars 1532 disposed in the non-junction region 1534 of the second substrate 1530. A passage 15 having neither the first pillar 1522 nor second pillar 1532 is formed at the center of the fluidic channel 1512. The detecting portion 1536 is disposed in the passage 15.

The flow of a liquid in the flow cell 150 having this structure will be explained. First, a liquid is introduced into the fluidic channel 1512. Since the surfaces of the first pillars 1522*a* disposed at the non-junction portion 1514 (non-junction region 1524) are hydrophilic and have good wettability with a liquid, the surface tension acts to suck in the introduced liquid. In contrast, the surfaces of the second pillars 1532 disposed at the non-junction portion 1514 (non-junction region 1534) are hydrophobic and have poor wettability with a liquid, so the surface tension acts to repel a liquid.

Thus, the liquid proceeds in a direction in which the first pillars 1522*a* with good wettability are disposed, and does not proceed in a direction in which the second pillars 1532 with poor wettability are disposed. The liquid selectively proceeds in the direction in which the first pillars 1522*a* are arrayed, and flows through the fluidic channel 1512.

An example of the use of the flow cell 150 according to the 14th embodiment will be explained.

The flow cell 150 in the 14th embodiment is used as a measurement chip for a surface plasmon resonance measurement apparatus 9201.

An antibody which reacts with an antigen is applied to the detecting portion 1536 of the second substrate 1530.

Figure 67:
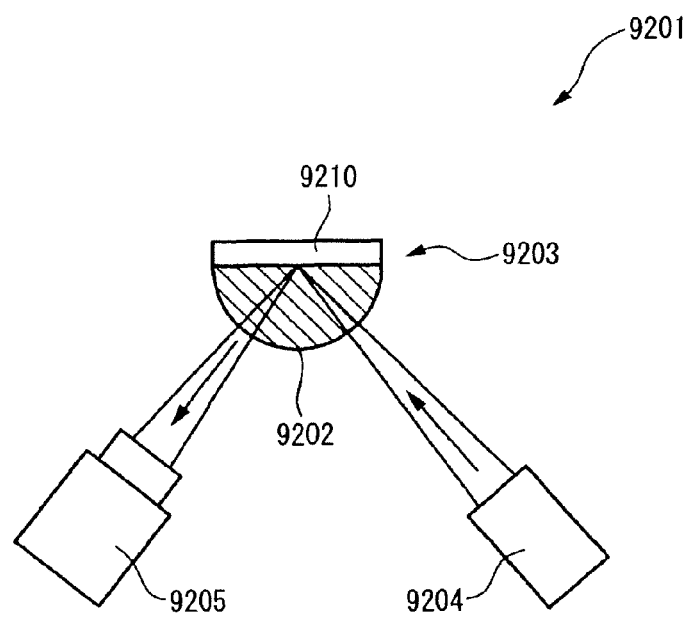
FIG. 67 is a schematic view showing the arrangement of a surface plasmon resonance measurement apparatus.

As shown in FIG. 67, the surface plasmon resonance measurement apparatus 9201 includes a semi-columnar prism 9202. Further, the surface plasmon resonance measurement apparatus 9201 includes a fixing portion 9203 at which the flow cell 150 in the 14th embodiment is fixed on the prism 9202, a laser emitting unit 9204 which emits a laser beam toward the detecting portion 1536 of the flow cell 150 via the prism 9202, and a laser detecting unit 9205 which detects the laser beam reflected by the detecting portion 1536.

The flow cell 150 in the 14th embodiment is fixed to the fixing portion 9203 so that the second substrate 1530 faces the prism 9202.

When a liquid is introduced into the fluidic channel 1512 of the flow cell 150, it flows along the array of the first pillars 1522*a* and passes on the detecting portion 1536.

If an antigen exists in the liquid, the antigen in the liquid flowing through the fluidic channel 1512 and the antibody applied to the detecting portion 1536 cause an antigen-antibody reaction, changing the refractive index of the surface of the detecting portion 1536. This change is detected as a change of the frequency at which the surface plasmon and evanescent wave resonate, thereby determining the presence/absence of the antigen.

In the flow cell 150 of the 14th embodiment having this structure, the first pillars 1522 stand on the opposite surface of the first substrate 1520. The second pillars 1532 stand on the opposite surface of the second substrate 1530. The flow cell 150 has the junction portions 1513 at which the first pillars 1522 and second pillars 1532 mesh with each other. The first substrate 1520 and second substrate 1530 can be jointed at the junction portions 1513, forming the flow cell 150.

Also, the flow cell 150 has the non-junction portion 1514 at which the first pillars 1522 and second pillars 1532 do not mesh with each other. At the non-junction portion 1514, the fluidic channel 1512 through which a liquid flows is formed. Therefore, a surface roughness very high to bring two rigid substrates into tight contact with each other is not required. Nor a process (e.g., joining under high pressure) for compensating for the difference in surface roughness is necessary. The flow cell 150 having the fluidic channel 1512 can be manufactured at low cost. Since the junction portions 1513 are arranged near the fluidic channel 1512, the first substrate 1520 and second substrate 1530 can be reliably joined to each other near the fluidic channel 1512, more reliably forming the fluidic channel 1512.

The first pillars 1522a are arrayed in the non-junction region 1524 (non-junction portion 1514) in the direction in which the fluidic channel 1512 extends. The second pillars 1532 are arrayed between lines of first pillars 1522a and the junction portions 1513. The surfaces of the first pillars 1522a are hydrophilic, and those of the second pillars 1532 are hydrophobic. The surfaces of the first pillars 1522a are good in wettability, and a liquid introduced into the fluidic channel 1512 selectively flows toward the first pillars 1522a. As a result, the fluidic channel 1512 is formed along the array of the first pillars 1522a. The surfaces of the second pillars 1532 disposed between lines of first pillars 1522a and the junction portions 1513 are hydrophobic, poor in wettability, and repel a liquid to prevent it from proceeding toward the second pillars 1532. The 14th embodiment can provide the flow cell 150 which prevents leakage of a liquid without bringing the first substrate 1520 and second substrate 1530 into completely tight contact with each other.

A pair of three-line groups of first pillars 1522a arrayed in the direction in which the fluidic channel 1512 extends is formed in the non-junction region 1524 (non-junction portion 1514). The passage 15 having neither the first pillar 1522 nor second pillar 1532 is formed between the paired lines of first pillars 1522a. The detecting portion 1536 is arranged in the passage 15. The detecting portion 1536 can perform measurement and detection without interference from the first pillars 1522 and second pillars 1532.

The entire surface of the first substrate 1520 is hydrophilic by a hydrophilic treatment, and that of the second substrate 1530 is hydrophobic. The flow cell 150 is formed by stacking the first substrate 1520 and second substrate 1530. The flow cell 150 of the 14th embodiment can be relatively easily manufactured without performing a hydrophilic treatment or hydrophobic treatment individually for the first pillars 1522 or second pillars 1532.

15th Embodiment

The 15th embodiment according to the present invention will be described with reference to FIGS. 68 to 70. The 15th embodiment is different from the 14th embodiment in the arrangements of first pillars 1622 and second pillars 1632, and the shape and arrangement of first pillars 1622a at a non-junction portion 1614.

Figure 68:
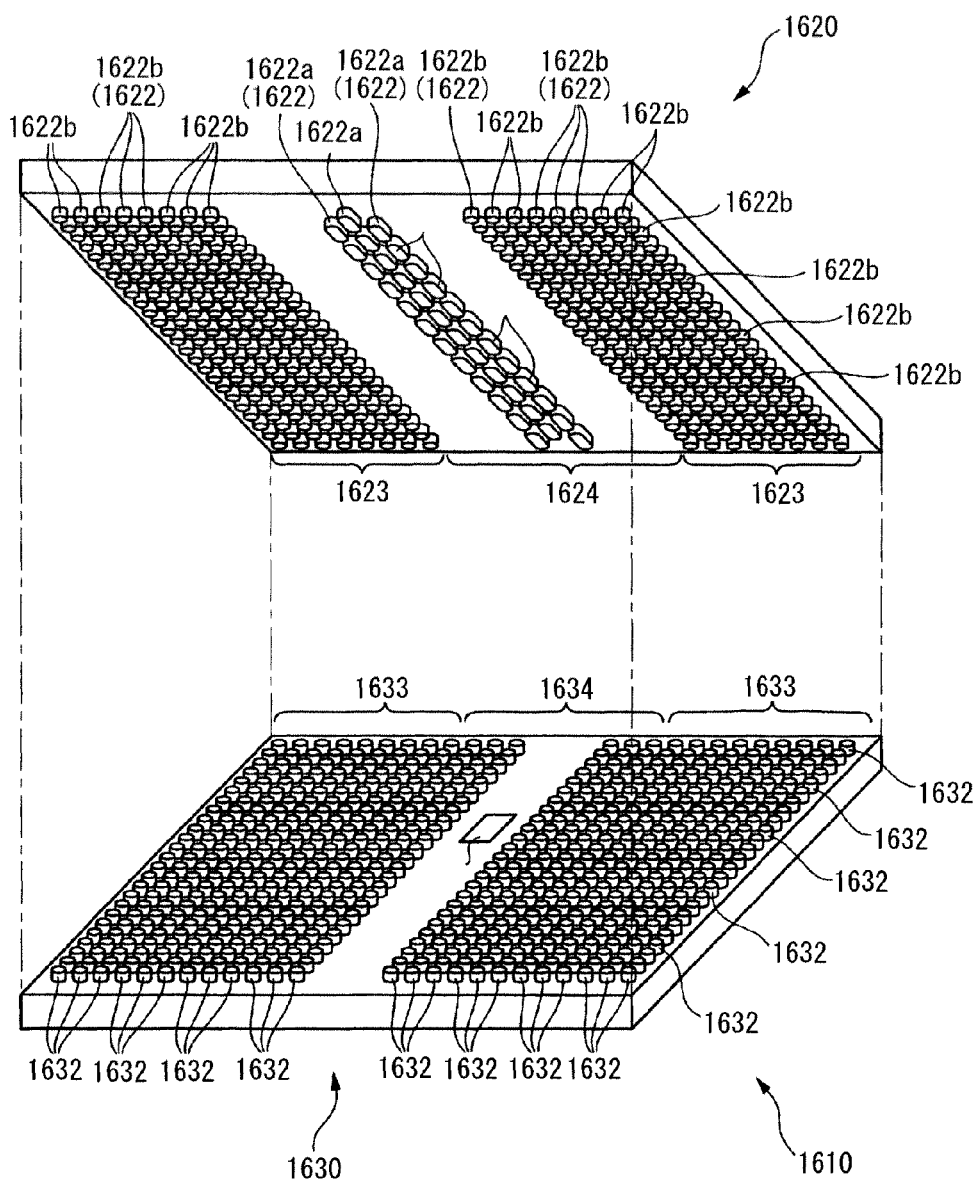
FIG. 68 is a perspective view of the first and second substrates which form a flow cell according to the 15th embodiment of the present invention.

As shown in FIG. 68, a first substrate 1620 is a rectangular flat plate. A plurality of first pillars 1622 stand on an opposite surface of the first substrate 1620 that is arranged to face a second substrate 1630. The first substrate 1620 is made of a synthetic resin such as a polymer resin. The entire surface of the first substrate 1620 is hydrophilic by a hydrophilic treatment, and the outer surfaces of the first pillars 1622 are also hydrophilic.

The first pillars 1622 are arrayed from one end (lower right side in FIG. 68) to the other end (upper left side in FIG. 68) of the first substrate 1620. Junction regions 1623 in each of which eight lines of columnar first pillars 1622b are arrayed are formed on sides (right and left sides in FIGS. 68 and 69) on the first substrate 1620. A non-junction region 1624 where three lines of first pillars 1622a are arrayed is formed between the junction regions 1623.

Figure 70:
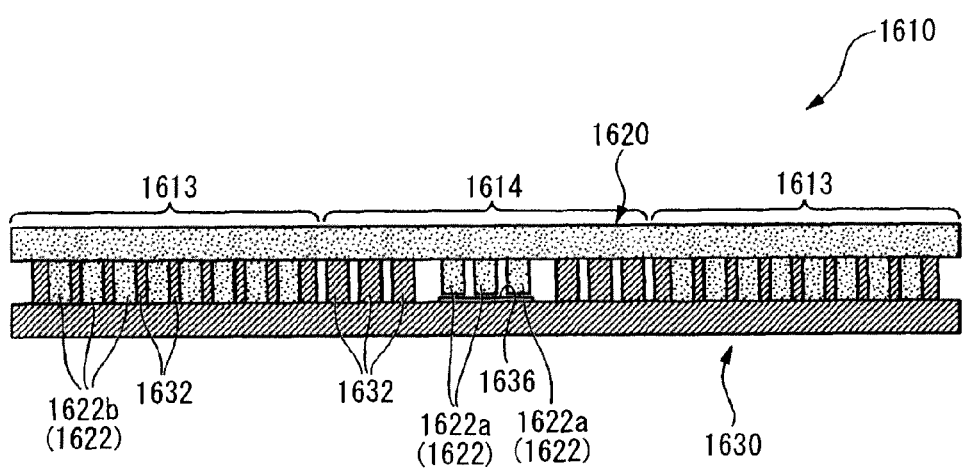
FIG. 70 is a sectional view taken along the line X-X in FIG. 69.

As shown in FIG. 70, the first pillars 1622a positioned in the non-junction region 1624 (non-junction portion 1614) are lower in projection height than the first pillars 1622b positioned in the junction regions 1623 (junction portions 1613).

The first pillars 1622a arrayed in the non-junction region 1624 have a shape and arrangement which continuously generate a surface tension in a direction in which a fluidic channel 1612 (to be described later) extends. More specifically, as shown in FIGS. 68 and 69, a section of the first pillar 1622a in the non-junction region 1624 that is perpendicular to a direction in which the first pillar 1622a projects has an almost oval shape. The ratio of dimensions in the longitudinal and widthwise directions, i.e., aspect ratio $\gamma 1$ is set to be higher than 1. The first pillars 1622a are arrayed so that the longitudinal direction of this section matches a direction in which the fluidic channel 1612 extends. The first pillars 1622a on the center line among the three lines of first pillars 1622a are arrayed at positions different from those of the first pillars 1622a on the right and left lines in the direction in which the fluidic channel 1612 extends. With this arrangement, at least one first pillar 1622a exists on a section perpendicular to the direction in which the fluidic channel 1612 extends.

As shown in FIG. 68, the second substrate 1630 is a rectangular flat plate. A plurality of second columnar pillars 1632 stand on an opposite surface of the second substrate 1630 that is arranged to face the first substrate 1620. The second substrate 1630 is made of a material which has relatively high rigidity and in which light is transmissive. In the 15th embodiment, the second substrate 1630 is made of a transparent polymer resin. The entire surface of the second substrate 1630 is hydrophobic, and the outer surfaces of the second pillars 1632 are also hydrophobic.

The second pillars 1632 are arrayed from one end (upper right side in FIG. 68) to the other end (lower left side in FIG. 68) of the second substrate 1630. Junction regions 1633 in each of which nine lines of second pillars 1632 are arrayed are formed on sides (right and left sides in FIGS. 68 and 69) on the second substrate 1630. A non-junction region 1634 where three lines of second pillars 1632 are disposed on each side is formed between the junction regions 1633.

A detecting portion 1636 supporting an antibody that reacts with a substance to be detected is arranged near the center of the opposite surface of the second substrate 1630, i.e., the center of the non-junction region 1634. In the 15th embodiment, the detecting portion 1636 includes a metal film which is formed on the opposite surface and is 100 nm or less in thickness, and an antibody film applied on the metal film.

The second pillars 1632 arrayed between lines of first pillars 1622a in the non-junction region 1624 and the junction regions 1623 have a shape and arrangement which discretely generate a surface tension. More specifically, as shown in FIGS. 68 and 69, a section of the second pillar 1632 that is perpendicular to a direction in which the second pillar 1632 projects has a circular shape. The ratio of dimensions in the longitudinal and widthwise directions, i.e., aspect ratio $\gamma 2$ is set to be 1. That is, the aspect ratio $\gamma 1$ of the section of the first pillar 1622a arranged in the non-junction region 1624 is set to be higher (γ1>γ2) than the aspect ratio γ2 of the section of the second pillar 1632.

The first substrate 1620 and second substrate 1630 are stacked while their opposite surfaces face each other. In the junction regions 1623 and 1633, as shown in FIG. 69, the first pillars 1622b and second pillars 1632 mesh with each other so that the second pillars 1632 of the second substrate 1630 enter the intervals between the first pillars 1622b of the first substrate 1620, thereby forming the junction portions 1613. By forming the junction portions 1613 in this fashion, the first substrate 1620 and second substrate 1630 are joined to each other, forming a flow cell 160 according to the 15th embodiment.

Figure 69:
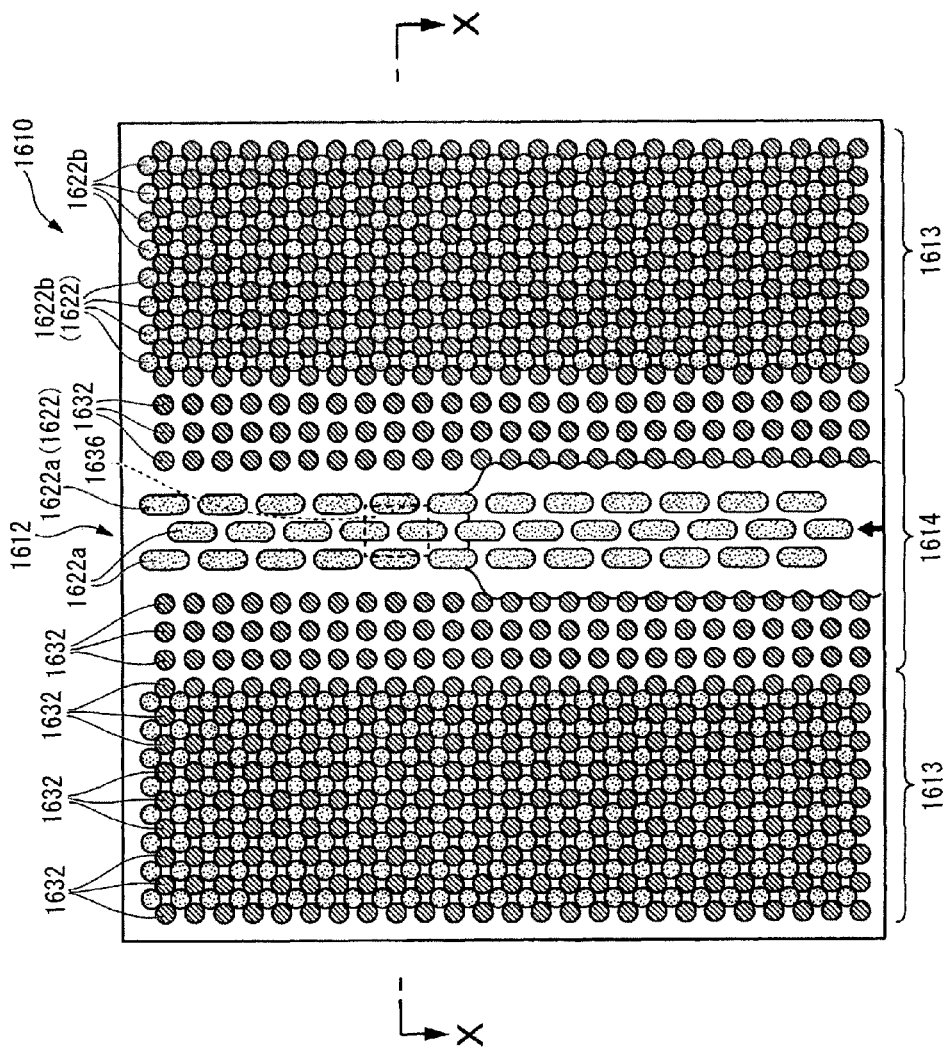
FIG. 69 is a view for explaining the section of the flow cell according to the 15th embodiment.

As shown in FIG. 69, lines of first pillars 1622a disposed in the non-junction region 1624 of the first substrate 1620 are interposed between lines of second pillars 1632 disposed in the non-junction region 1634 of the second substrate 1630, forming the non-junction portion 1614 at which the first pillars 1622a and second pillars 1632 do not mesh with each other.

At the non-junction portion 1614, the fluidic channel 1612 is defined by the first pillars 1622a disposed in the non-junction region 1624 of the first substrate 1620 and the second pillars 1632 disposed in the non-junction region 1634 of the second substrate 1630. The first pillars 1622a arrayed in the non-junction region 1624 are lower in projection height than the first pillars 1622b arrayed in the junction regions 1623. As shown in FIG. 70, the tips of the first pillars 1622a are arranged at positions spaced apart from the second substrate 1630, forming a gap. At this gap, the detecting portion 1636 is arranged.

In the flow cell 160 of the 15th embodiment having this structure, the surface tension acts continuously in the longitudinal direction of the section of the first pillar 1622a disposed at the non-junction portion 1614 (non-junction region 1624). The surface tension acts discretely in the widthwise direction of the first pillar 1622a and at the portion at which the second pillars 1632 are disposed. A liquid introduced into the fluidic channel 1612 selectively proceeds in the longitudinal direction of the first pillars 1622a in which the surface tension acts continuously. The liquid does not proceed toward the second pillars 1632 on which the surface tension acts discretely. Since the surfaces of the first pillars 1622a are hydrophilic and those of the second pillars 1632 are hydrophobic, the liquid flows along the array of the first pillars 1622a.

In the 15th embodiment, at least one first pillar 1622a is arranged on a section perpendicular to the direction in which the fluidic channel 1612 extends. The surface tension acts continuously in the direction in which the fluidic channel 1612 extends. The surface tension can reliably transfer a liquid in the direction in which the fluidic channel 1612 extends.

As shown in FIG. 70, the tips of the first pillars 1622a are arranged at positions spaced apart from the second substrate 1630, forming a gap. At this gap, the detecting portion 1636 is arranged. The detecting portion 1636 can measure and detect a liquid without interfering the first pillars 1622 and second pillars 1632.

16th Embodiment

The 16th embodiment according to the present invention will be described with reference to FIGS. 71 and 72.

A first substrate 1720 is a rectangular flat plate. A plurality of first pillars 1722 stand on an opposite surface of the first substrate 1720 that is arranged to face a second substrate 1730. The first substrate 1720 is made of a material which has relatively high rigidity and in which light is transmissive. The entire surface of the first substrate 1720 is hydrophilic by a hydrophilic treatment, and the outer surfaces of the first pillars 1722 are also hydrophilic.

The first pillars 1722 are arrayed from one end to the other end of the first substrate 1720. Junction regions in each of which five lines of first pillars 1722 are arrayed are formed on sides on the first substrate 1720. A non-junction region where three lines of first pillars 1722 are arrayed on each side is formed between the junction regions.

A pair of guide ribs 1725 which extend along the array of the first pillars 1722 is interposed between the three-line groups of first pillars 1722 in the non-junction region. A detecting portion 1726 supporting an antibody that reacts with a substance to be detected is interposed between the paired guide ribs 1725. As shown in FIG. 72, the guide rib 1725 is lower in projection height than the first pillar 1722.

The second substrate 1730 is a rectangular flat plate. A plurality of second columnar pillars 1732 stand on an opposite surface of the second substrate 1730 that is arranged to face the first substrate 1720. The second substrate 1730 is made of a material which has relatively high rigidity and in which light is transmissive. In the 16th embodiment, the second substrate 1730 is made of a transparent polymer resin. The entire surface of the second substrate 1730 is hydrophobic, and the outer surfaces of the second pillars 1732 are also hydrophobic.

The second pillars 1732 are arrayed from one end to the other end of the second substrate 1730. Junction regions in each of which six lines of second pillars 1732 are arrayed are formed on sides on the second substrate 1730. A non-junction region where three lines of second pillars 1732 are disposed on each side is formed between the junction regions.

The first substrate 1720 and second substrate 1730 are stacked while their opposite surfaces face each other. In the junction regions, as shown in FIG. 71, first pillars 1722b and the second pillars 1732 mesh with each other so that the second pillars 1732 of the second substrate 1730 enter the intervals between the first pillars 1722b of the first substrate 1720, thereby forming junction portions 1713. By forming the junction portions 1713 in this way, the first substrate 1720 and second substrate 1730 are joined to each other, forming a flow cell 170 according to the 16th embodiment.

Figure 71:
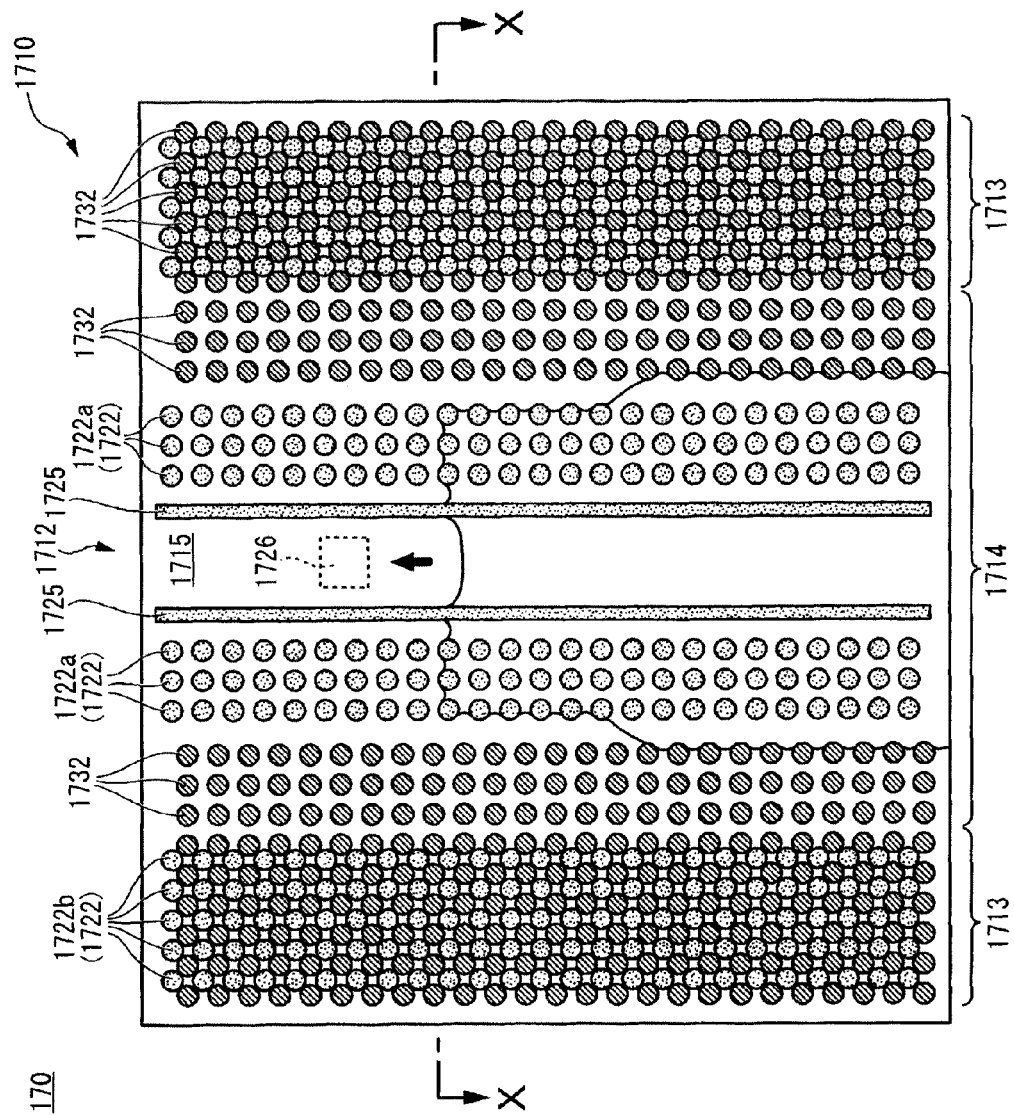
FIG. 71 is a view for explaining the section of a flow cell according to the 16th embodiment of the present invention.
Figure 72:
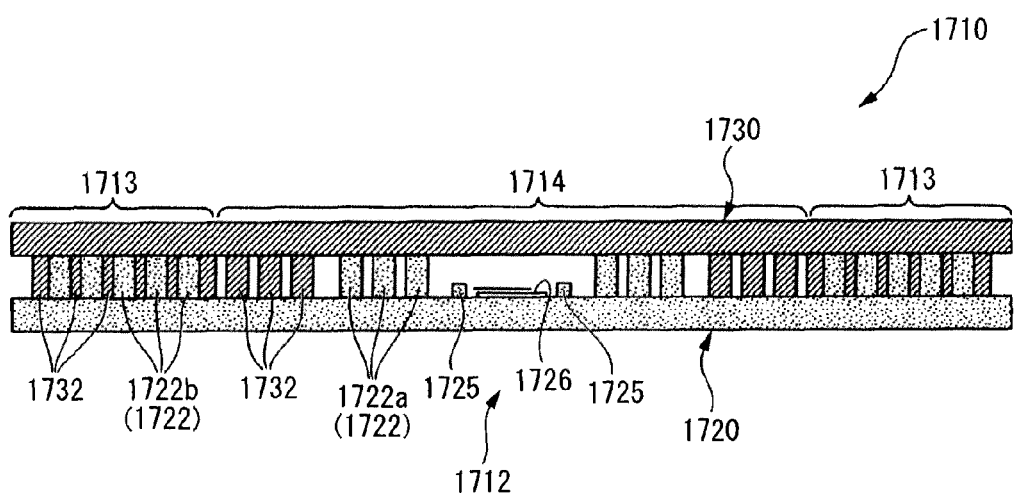
FIG. 72 is a sectional view taken along the line X-X in FIG. 71.

As shown in FIG. 71, first pillars 1722a disposed in the non-junction region of the first substrate 1720 are interposed between lines of second pillars 1732 disposed in the non-junction regions of the second substrate 1730, forming a non-junction portion 1714 at which the first pillars 1722a and second pillars 1732 do not mesh with each other.

At the non-junction portion 1714, a fluidic channel 1712 is formed by the first pillars 1722a disposed in the non-junction region of the first substrate 1720 and the second pillars 1732 disposed in the non-junction region of the second substrate 1730. A passage 1715 having neither the first pillar 1722a nor second pillar 1732 is formed at the center of the fluidic channel 1712. The detecting portion 1726 is disposed at a portion in the passage 1715. The guide ribs 1725 are disposed in the passage 1715.

In the flow cell 170 of the 16th embodiment having this structure, a liquid is sucked by lines of first pillars 1722a disposed on the two sides of the passage 1715. By the suction force, the liquid flows through the passage 1715. Since the guide ribs 1725 which extend in the direction in which the fluidic channel 1712 extends are formed in the passage 1715, they make the surface tension act continuously. This further promotes the flow of a liquid through the fluidic channel 1712.

The flow cells 150 to 170 according to the embodiments of the present invention have been described. However, the technical scope of the present invention is not limited to them, and various changes and modifications can be made without departing from the technical concept of the invention.

For example, in the above description, the first and second substrates are made of a synthetic resin such as a polymer resin. However, the first and second substrates are not limited to them and may be made of another synthetic resin, glass, metal, ceramic, or the like.

In the 15th embodiment, the section of the first pillar 1622a arranged in the non-junction region 1624 has an almost oval shape. However, the first pillar 1622a is not limited to this, and suffices to have a shape and arrangement which generates a surface tension continuously in the direction in which the fluidic channel 1612 extends. For example, the first pillar 1622a may project in the direction in which the fluidic channel 1612 extends. Even in this case, the first projecting pillars 1622a generate a surface tension continuously in the direction in which the fluidic channel extends, thereby forming the fluidic channel 1612.

The first and second pillars have been explained by illustrating their sectional shapes which are constant in the direction in which the first and second pillars project. However, the first and second pillars are not limited to them, and their sectional shapes or sizes may change in the direction in which the first and second pillars project, like a truncated cone. When the shape of the first and second pillars is a truncated cone whose diameter gradually decreases in a direction in which the truncated cone projects, this facilitates positioning when staking the first and second substrates.

The first and second pillars are disposed at a portion at which the fluidic channel is formed. However, the present invention is not limited to this, and a defined space may be used as the fluidic channel without disposing the first and second pillars.

A flow cell used in the surface plasmon resonance method has been described. However, the flow cell is not limited to this and may be used in another analysis or the like.

The invention claimed is:

1. A flow cell comprising: a first substrate in which light is transmissive; a second substrate which is disposed on said first substrate; an opening which is formed in said second substrate; a fluidic channel which is formed between said first substrate and said second substrate and has one end connected to the opening; and a pump which is formed between said first substrate and said second substrate, is connected to the other end of the fluidic channel, and sucks, by a surface tension generated by said first substrate and said second substrate, a liquid that has reached the fluidic channel from the opening, wherein said pump includes a recess formed in at least one of said first substrate and said second substrate, and a plurality of pillars which stand upright in the recess, and the pillars do not contact either of said first substrate and said second substrate.

2. A flow cell according to claim 1, further comprising a third substrate which is interposed between said first substrate and said second substrate, wherein the recess is formed in said second substrate, the fluidic channel is formed in said third substrate, said pump sucks the liquid by a surface tension generated by said second substrate and said third substrate, and the pillars stand upright from said second substrate and do not contact said third substrate.

3. A flow cell comprising: a first substrate in which light is transmissive; a second substrate which is disposed on said first substrate; a third substrate which is disposed on said second substrate; an opening which is formed in said second substrate and said third substrate; a fluidic channel which is formed between said first substrate and said second substrate and has one end connected to the opening; and a pump which is formed between said first substrate and said second substrate and between said second substrate and said third substrate, is connected to the other end of the fluidic channel, and sucks, by surface tensions generated by said first substrate and said second substrate and by said second substrate and said third substrate, a liquid that has reached the fluidic channel from the opening.

4. A flow cell according to claim 3, wherein said second substrate further comprises a connection hole which vertically passes through said second substrate, said pump includes a first pump which is formed between said first substrate and said second substrate, and a second pump which is formed between said second substrate and said third substrate, and said first pump and said second pump are connected to each other via the connection hole.

5. A flow cell according to claim 3, wherein said second substrate and said third substrate further comprise vents which vertically pass through said second substrate and said third substrate.

6. A flow cell according to claim 3, wherein at least a pair of said second substrate and said third substrate is disposed on said third substrate.

7. A flow cell according to claim 4, further comprising a fourth substrate which is interposed between said first substrate and said second substrate, wherein the fluidic channel is formed in said fourth substrate, and said first pump is formed between said second substrate and said fourth substrate, and sucks the liquid by a surface tension generated by said second substrate and said fourth substrate.

8. A flow cell according to claim 3, wherein said pump includes a recess formed in at least either of an upper surface and lower surface of said second substrate, and a plurality of pillars which stand upright in the recess, and the pillars have open ends.

* * * * *